(12) United States Patent
Bell et al.

(10) Patent No.: US 11,786,528 B2
(45) Date of Patent: Oct. 17, 2023

(54) PYRAZOLOPYRIMIDINE COMPOUNDS AS ADENOSINE RECEPTOR ANTAGONISTS

(71) Applicants: EXSCIENTIA LTD., Dundee (GB); EVOTEC INTERNATIONAL GMBH, Hamburg (DE)

(72) Inventors: Andrew Simon Bell, Dundee (GB); Adrian Michael Schreyer, Dundee (GB); Stephanie Versluys, Toulouse (FR)

(73) Assignees: EXSCIENTIA LTD., Dundee (GB); EVOTEC INTERNATIONAL GMBH, Hamburg (DE)

( * ) Notice: Subject to any disclaimer, the term of this patent is extended or adjusted under 35 U.S.C. 154(b) by 257 days.

(21) Appl. No.: 15/734,074

(22) PCT Filed: Jun. 4, 2019

(86) PCT No.: PCT/EP2019/064450
§ 371 (c)(1),
(2) Date: Dec. 1, 2020

(87) PCT Pub. No.: WO2019/233994
PCT Pub. Date: Dec. 12, 2019

(65) Prior Publication Data
US 2021/0251995 A1    Aug. 19, 2021

(30) Foreign Application Priority Data
Jun. 4, 2018    (EP) .................................... 18290061

(51) Int. Cl.
| | | |
|---|---|---|
| *C07D 487/04* | (2006.01) | |
| *A61P 35/00* | (2006.01) | |
| *A61K 31/519* | (2006.01) | |
| *G01N 33/566* | (2006.01) | |

(52) U.S. Cl.
CPC ............ *A61K 31/519* (2013.01); *A61P 35/00* (2018.01); *C07D 487/04* (2013.01); *G01N 33/566* (2013.01)

(58) Field of Classification Search
CPC ..... A61K 31/519; A61P 35/00; C07D 487/04; G01N 33/566
See application file for complete search history.

(56) References Cited

U.S. PATENT DOCUMENTS

| | | |
|---|---|---|
| 8,283,476 B2 | 10/2012 | Halland |
| 9,353,116 B2 | 5/2016 | Garske |
| 9,365,574 B2 | 6/2016 | Raghavan |
| 9,580,416 B2 | 2/2017 | Chen |
| 10,519,160 B2 | 12/2019 | Van De Bittner |
| 2003/0114467 A1 | 6/2003 | Shakespeare |
| 2007/0004761 A1 | 1/2007 | Basarab |
| 2010/0273776 A1 | 10/2010 | Lindquist |
| 2010/0331297 A1 | 12/2010 | Bulawa |
| 2015/0315198 A1 | 11/2015 | Li et al. |
| 2020/0299285 A1 | 9/2020 | Fletcher |
| 2022/0168315 A1 | 6/2022 | Bajji |

FOREIGN PATENT DOCUMENTS

| | | |
|---|---|---|
| CN | 112608318 A | 4/2021 |
| EP | 1 949 903 B1 | 4/2012 |
| IT | 2007RM0480 | 7/2007 |
| WO | WO 97/46560 | 12/1997 |
| WO | WO2005049616 A1 | 6/2005 |
| WO | WO 2008/141385 A1 | 11/2008 |
| WO | WO 2011/121418 A1 | 10/2011 |
| WO | WO 2011/050245 A1 | 11/2011 |
| WO | WO 2011/153588 A1 | 12/2011 |
| WO | WO 2013/106254 A1 | 7/2013 |
| WO | WO 2014/126580 A1 | 8/2014 |
| WO | WO 2017/025918 A1 | 2/2017 |
| WO | WO 2017/112917 | 6/2017 |
| WO | WO 2021/121397 A1 | 6/2021 |
| WO | WO 2022/125377 A1 | 6/2022 |
| WO | WO 2022/268209 A1 | 12/2022 |

OTHER PUBLICATIONS 2061415-13-0 entered in STN on Jan. 31, 2017 (Year: 2017).*
2061415-07-2 entered in STN on Jan. 31, 2017 (Year: 2017).*
2062036-96-6 entered in STN on Jan. 31, 2017 (Year: 2017).*
Indian Office Action dated Jun. 6, 2022 in counterpart Indian Application No. 202047052525.
International Search Report issued in International Application No. PCT/EP2019/064450, dated Nov. 19, 2019.
Written Opinion of the International Searching Authority issued in International Application No. PCT/EP2019/064450, dated Nov. 19, 2019.
Database Registry, [Online], Chemical Abstracts Service, Columbus, Ohio, US; Jan. 30, 2017 (Jan. 30, 2017), XP002784453, Database accession No. 2061415-13-0, Chemical Library, Supplier: Aurora Fine, Chemicals; RNs 2061415-07-2 and 206141-13-0.

(Continued)

*Primary Examiner* — Erich A Leeser
(74) *Attorney, Agent, or Firm* — Charles C. Achkar; Ostrolenk Faber LLP

(57) ABSTRACT

The invention provides a compound of formula (I), or pharmaceutically acceptable ester, amide, carbamate, solvate or salt thereof, including a salt of such an ester, amide or carbamate,

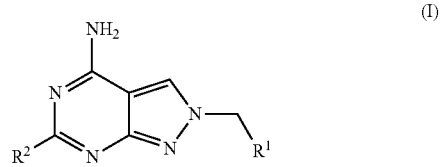

(I)

wherein $R^1$ is an optionally substituted phenyl, or an optionally substituted 5- or 6-membered aromatic heterocycle; and $R^2$ is an optionally substituted 5- or 6-membered aromatic heterocycle. Also provided are pharmaceutical compositions comprising a compound of formula (I).

28 Claims, 1 Drawing Sheet

(56) References Cited

OTHER PUBLICATIONS

Database Registry [Online], Chemical Abstracts Service, Columbus, Ohio, US; Jan. 31, 2017 (Jan. 31, 2017), XP002784454, Database accession No. 2062036-96-6 Chemical Library, Supplier: Aurora Fine, Chemicals; RN 2062036-96-6.
Squarcialupi Lucia et al: "Exploring the 2- and 5-positions of the pyrazolo[4,3-d]pyrimidin-7-amino scaffold to target human Aland A2Aadenosine receptors", Bioorganic & Medicinal Chemistry Pergamon, GB, vol. 24, No. 12, Apr. 23, 2016(Apr. 23, 2016), pp. 2794-2808 XP029556496, ISSN: 0968-0896, DOI: 10.1016/J.BMC. 2016.04.048 cited in the application table 1; compounds 22-31.
Sabrina Taliani et al: "Novel N 2-Substituted Pyrazolo[3,4-d]pyrimidine Adenosine A 3 Receptor Antagonists: Inhibition of A 3-Mediated Human Glioblastoma Cell Proliferation +", Journal of Medicinal Chemistry, vol. 53, No. 10, May 27, 2010 (May 27, 2010), pp. 3954-3963, XP055054412, ISSN: 0022-2623, DOI: 10.1021/jm901785w cited in the application table 1; compounds 6-8.
Congreve et al., J. Med. Chem., 2012, 55, 1898-1903.
Supplementary information for Congreve et al., J. Med. Chem., 2012, 55, 1898-1903.
Jazeyri et al., Chem. Rev., 2017, 117, 1, 21-37.
Jenner, "An Overview of Adenosine A2A Receptor Antagonists in Parkinson's Disease", Int. Rev. Neurobiol., 2014, 119, chapter 3, 71-86.
Mediavilla-Varela, M et al Neoplasia 2017 19 530.
Squarcialupi et al., Biorganic and Medicinal Chemistry, 2016, 24, 2794-2808.
Squarcialupi et al., Eur. J. Med. Chem., 2014, 84, 614-627.
Stagg and Smyth, Oncogene, 2010, 29(39), 5346-5358.
Young et al., Cancer Discovery, 2014, 4, 879-888.
Taliani et al., J. Med. Chem., 2010, 53, 3954-3963.
Russian Office Action dated Dec. 8, 2022 in counterpart Russian Application No. 2020140644/04 (075638) with machine English language translation.
Catalogue compounds located by FTO search.
STN Registry No. 2062318-40-3, Entry date: Jan. 31, 2017.
STN Registry No. 2062315-34-6, Entry date: Jan. 31, 2017.
STN Registry No. 2062189-55-1, Entry date: Jan. 31, 2017.
STN Registry No. 2062188-58-1, Entry date: Jan. 31, 2017.
STN Registry No. 2062187-98-6, Entry date: Jan. 31, 2017.
STN Registry No. 2062036-51-3, Entry date: Jan. 31, 2017.
STN Registry No. 2062035-90-7, Entry date: Jan. 31, 2017.
STN Registry No. 2062035-52-1, Entry date: Jan. 31, 2017.
STN Registry No. 2062034-99-3, Entry date: Jan. 31, 2017.
STN Registry No. 2061419-51-8, Entry date: Jan. 30, 2017.
STN Registry No. 2061419-50-7, Entry date: Jan. 30, 2017.
STN Registry No. 2061153-17-9, Entry date: Jan. 29, 2017.
STN Registry No. 2061152-90-5, Entry date: Jan. 29, 2017.
STN Registry No. 2061152-78-9, Entry date: Jan. 29, 2017.
STN Registry No. 2061152-40-5, Entry date: Jan. 29, 2017.
STN Registry No. 2060788-14-7, Entry date: Jan. 29, 2017.
STN Registry No. 2060527-91-3, Entry date: Jan. 27, 2017.
STN Registry No. 2060527-83-3, Entry date: Jan. 27, 2017.
STN Registry No. 2060527-77-5, Entry date: Jan. 27, 2017.
STN Registry No. 2060527-47-9, Entry date: Jan. 27, 2017.
STN Registry No. 2060525-12-2, Entry date: Jan. 27, 2017.
STN Registry No. 2059790-31-5, Entry date: Jan. 26, 2017.
STN Registry No. 2059787-88-9, Entry date: Jan. 26, 2017.
STN Registry No. 2059787-87-8, Entry date: Jan. 26, 2017.
STN Registry No. 2059177-25-0, Entry date: Jan. 25, 2017.
STN Registry No. 2058942-99-5, Entry date: Jan. 25, 2017.
STN Registry No. 2058942-98-4, Entry date: Jan. 25, 2017.
STN Registry No. 2058934-50-0, Entry date: Jan. 25, 2017.
STN Registry No. 2058934-49-7, Entry date: Jan. 25, 2017.
STN Registry No. 1025885-32-8, Entry date: Jun. 5, 2008.
Office Action issued in counterpart Japanese Application No. 2020-567151, dated Apr. 26, 2023 with English language translation thereof.
Da Settimo, F., et al., Journal of Medicinal Chemistry, 2005, vol. 48, No. 16, pp. 5162-5174.

\* cited by examiner

PYRAZOLOPYRIMIDINE COMPOUNDS AS ADENOSINE RECEPTOR ANTAGONISTS

CROSS REFERENCE TO RELATED APPLICATIONS

The present application is a § 371 National Phase application based on PCT/EP2019/064450 filed Jun. 4, 2019, which claims the benefit of European application No. 18290061.3 filed Jun. 4, 2018, the subject matter of each of which is incorporated by reference in their entirety.

FIELD OF INVENTION

The present invention relates to compounds of formula (I), and pharmaceutically acceptable esters, amides, carbamates, solvates or salts thereof, including salts of such esters, amides or carbamates, which have activity as adenosine 2a receptor antagonists. The invention also relates to pharmaceutical compositions comprising such compounds, and to the use of such compounds as medicaments, in particular in the treatment of cancer.

BACKGROUND TO THE INVENTION

Levels of adenosine triphosphate (ATP) and adenosine are raised in tumour microenvironments, hence both are implicated in tumour growth (Stagg, J and Smyth, M J Oncogene 2010 29 5436; Young A, Mittal, D, Stagg, J and Smyth M J Cancer Discovery 2014 879). The dominant pathway that leads to elevation of extracellular adenosine levels involves the hydrolysis of ATP by ectonucleosidases (CD39 and CD73), whereas the downstream effects of adenosine are mediated through adenosine receptors. There are four adenosine receptor sub-types (adenosine 1 (A1), adenosine 2a (A2a), adenosine 2b (A2b) and adenosine 3 (A3)), each of them being reported to be upregulated in different tumour tissues. The effects of the receptors are opposing to some extent since A1 and A3 receptors act to inhibit cAMP release while the A2 subtypes stimulate signalling via cAMP. Consequently, antagonism of the A2a and/or A2b receptors are of interest as anti-tumour therapies.

Antagonism of the A2a receptor has been a longstanding approach for treating neurological disorders such as Parkinson's disease (Jenner P, International Review of Neurobiology 2014 119 71) using clinical candidates istradefylline, preladenant, vipadenant, tozadenant and SCH 58261 (see Jazeyri A, Andrews S P, and Marshall F H Chem. Rev. 2017, 117, 21-37. Subsequent research lead to molecules such as CPI-444 (previously VER-6623) and AZD4635 (previously HTL-1071), which were designed as treatments for Parkinson's disease but are undergoing clinical trials against various cancers. The use of CPI-444 to treat cancer is disclosed in WO 2017/112917 (Corvus Pharmaceuticals). Mediavilla-Varela, M et al Neoplasia 2017 19 530 reports that the adenosine A2a receptor antagonist PBF-509 is an immunotherapeutic in non-small cell lung cancer.

Taliani, S et al J. Med Chem 2010 53 3954 describes various compounds reported to be selective A3 receptor antagonists, including compounds having a pyrazolo[3,4-d]pyrimidine core. Squarcialupi, L et al Eur. J. Med Chem 2014 84 614 and Squarcialupi, L et al Biorganic and Medicinal Chemistry 2016 24 2794-2808 also teach various compounds having a pyrazolo[4,3-d]pyrimidine core structure, and reports those compounds to be A1 receptor antagonist and/or A2a receptor antagonists.

SUMMARY OF THE INVENTION

The invention provides a compound of formula (I), or pharmaceutically acceptable ester, amide, carbamate, solvate or salt thereof, including a salt of such an ester, amide or carbamate,

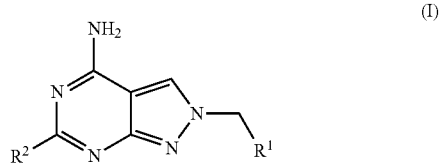

wherein $R^1$ is an optionally substituted phenyl, or an optionally substituted 5- or 6-membered aromatic heterocycle comprising 1, 2 or 3 heteroatoms independently selected from the group consisting of N, S and O, wherein said phenyl is optionally substituted with 1, 2 or 3 substituents, each substituent being independently selected from the group consisting of halogen, OH, $C_{1-8}$-alkyl, $C_{1-8}$-alkyl substituted with 1, 2 or 3 halogens or OH groups, $OC_{1-8}$-alkyl, and $OC_{1-8}$-alkyl substituted with 1, 2 or 3 halogens or OH groups, and wherein said 5- or 6-membered aromatic heterocycle is optionally substituted with 1, 2 or 3 substituents, each substituent being independently selected from the group consisting of halogen, OH, $C_{1-8}$-alkyl, $C_{1-8}$-alkyl substituted with 1, 2 or 3 halogens or OH groups, $OC_{1-8}$-alkyl, and $OC_{1-8}$-alkyl substituted with 1, 2 or 3 halogens or OH groups; and $R^2$ is an optionally substituted 5- or 6-membered aromatic heterocycle comprising 2 or 3 heteroatoms independently selected from the group consisting of N, S and O, wherein said 5- or 6-membered aromatic heterocycle is optionally substituted with 1, 2 or 3 substituents, each substituent being independently selected from the group consisting of $C_{1-3}$alkyl and $C_{1-3}$ alkyl substituted with 1, 2 or 3 halogens.

For example, the compound of the invention is a compound of formula (I), or a pharmaceutically acceptable salt, ester, amide or carbamate thereof, or a salt of such an ester, amide or carbamate, with the proviso that the compounds is not selected from the group consisting of

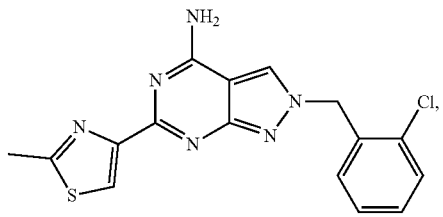

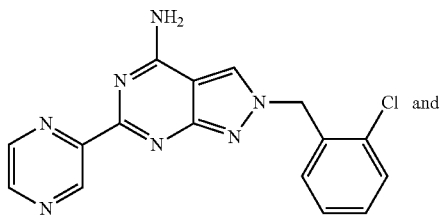

Cl and

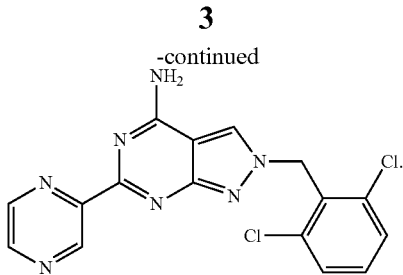

Compounds of the invention have surprisingly been found to be antagonists of the A2a receptor, and in particular selective antagonists of the A2a receptor. Accordingly, the compounds have use in the treatment or prophylaxis of diseases and disorders associated with the A2a receptor.

Thus, the present invention further provides a pharmaceutical composition which comprises a compound of formula (I), together with a pharmaceutically suitable carrier.

The present invention further provides a compound of formula (I) or a composition comprising a compound of formula (I), for use as a medicament, and in particular for use in the treatment or prophylaxis of a disease or disorder associated with the A2a receptor.

The present invention further provides the use of a compound of formula (I) or a composition comprising a compound of formula (I), for the manufacture of a medicament for the treatment or prophylaxis of a disease or disorder associated with the A2a receptor. The present invention further provides a method for the treatment or prophylaxis of a disease or disorder associated with the A2a receptor in a mammal, which comprises administering to the mammal a therapeutically effective amount of a compound of formula (I) or a composition comprising a compound of formula (I).

The present invention also provides the use of a compound of formula (I) in labelled form as a diagnostic agent for the diagnosis of a disease or disorder associated with the A2a receptor. The present invention also provides the use of a compound of formula (I) or a labelled form of such a compound as a reference compound in a method of identifying ligands for the A2a receptor.

DETAILED DESCRIPTION OF THE INVENTION

Figure 1:
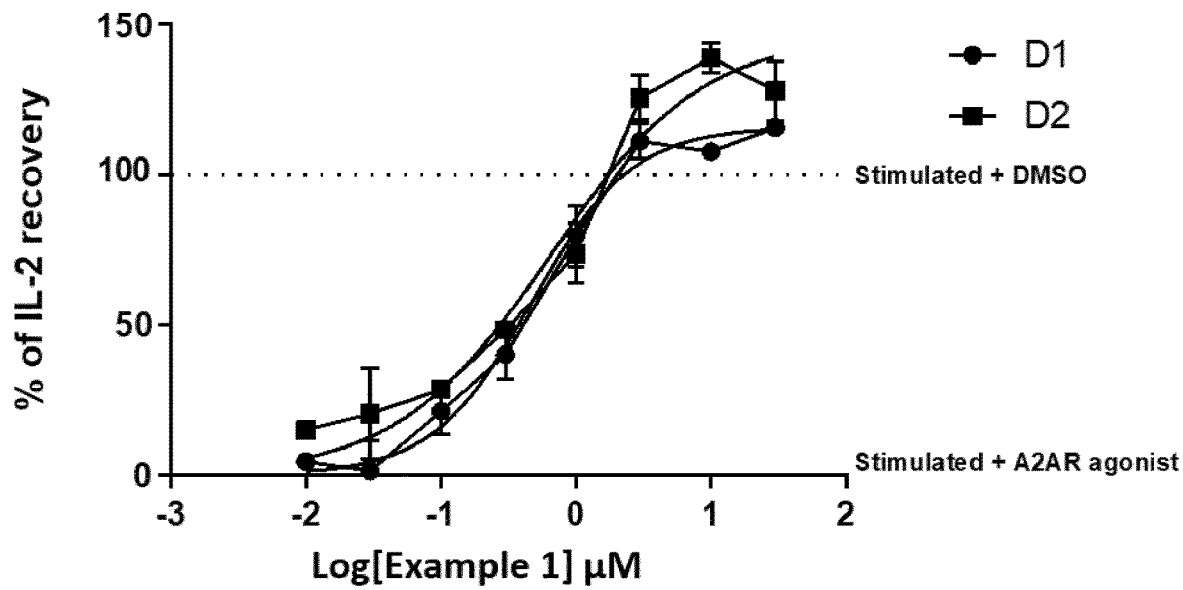
FIG. 1 shows a graph of dose effect of Example 1 on recovery of 2-chloroadenosine (CADO) mediated inhibition of IL-2 production in human primary CD3+ T-cells. D1 indicates T-cells obtained from donor 1; D2 indicates T-cells obtained from donor 2.

The invention provides a compound of formula (I) as defined above. The compounds of the present invention have a pyrazolo[3,4-d]pyrimidine core structure, and more particularly a 4-amino-2H-pyrazolo[3,4-d]pyrimidine core structure which is unsubstituted at the 3-position of the pyrazolo[3,4-d]pyrimidine ring. As well having this specific core arrangement, the compounds of the present invention have a 5- or 6-membered aromatic heterocycle comprising 2 or 3 heteroatoms independently selected from the group consisting of N, S and O at the 6-position of the pyrazolo[3,4-d]pyrimidine ring. The compounds also have an optionally substituted phenyl, or an optionally substituted 5- or 6-membered aromatic heterocycle comprising 1, 2 or 3 heteroatoms attached to the 2-position of the pyrazolo[3,4-d]pyrimidine ring via a CH$_2$ linker. The present inventors have surprisingly found that this arrangement, and in particular the pyrazolo[3,4-d]pyrimidine core and having 2 or 3 heteroatoms in a monocyclic ring at the 6-position, leads to especially selective antagonists of the A2a receptor. The compounds are selective for the A2a receptor over at least one of (and preferably all of) the A1, A2b and A3 receptors. In particular, the compounds of the invention are especially selective for the A2a receptor over the A1 receptor, and are more selective for the A2a receptor over the A1 receptor than the compounds of the prior art (see, for example, Table 3 below which shows the relative selectivity of various compounds of the invention and the selectivity of Comparative Example 1, which is compound 25 disclosed in Squarcialupi, L et al Biorganic and Medicinal Chemistry 2016 24 2794-2808). Selectivity for the A2a receptor over the A1 receptor is an important advantage of the compounds of the present invention, as antagonism of the A1 receptor can lead to adverse side effects, and in particularly adverse effects on the heart such as irregular heart rate or rapid heart rate.

As well as being selective, the compounds also have good affinity for the A2a receptor, and have good functional activity as A2a receptor antagonists (for example, as shown in the functional in vitro assay described in the examples section below). They also have favourable pharmacokinetic properties making them particularly suitable compounds for use as medicaments.

Furthermore, the compounds have acceptable aqueous solubility for pharmaceutical use. Aqueous solubility is a very important parameter for compounds that have utility as medicaments. An acceptable level of solubility is required to achieve a desired concentration of drug in systemic circulation for the desired pharmacological response. Low aqueous solubility is a major problem encountered with formulation development of new chemical entities for use as medicaments, in particular medicaments that may be administered orally. The aqueous solubility of the compounds of the invention makes the compounds especially suitable for use as medicaments, and in particular medicaments suitable for oral administration.

In the compounds of formula (I), R$^1$ may be an optionally substituted phenyl, or an optionally substituted 5- or 6-membered aromatic heterocycle comprising 1, 2 or 3 heteroatoms independently selected from the group consisting of N, S and O.

When R$^1$ is an optionally substituted phenyl, the phenyl may be substituted, or it may be unsubstituted. In embodiments where R$^1$ is an optionally substituted phenyl, said phenyl may be optionally substituted with 1 substituent, and the substituent may be at the ortho, meta or para position of the phenyl ring. In certain preferred embodiments, it is at the at the meta position. In other preferred embodiments, it is at the at the ortho or para position. In embodiments where R$^1$ is optionally substituted phenyl, said phenyl may be substituted with 2 substituents, and the substituents may be, for example, at the 2 and 3 positions, the 2 and 4 positions, the 2 and 6 positions, the 3 and 4 positions, or the 3 and 5 positions. In certain preferred embodiments, the substituents may be at the 2 and 3 positions. In other preferred embodiments, the substituents may be at the 2 and 3 positions or the 2 and 5 positions.

In one preferred embodiment, $R^1$ is an optionally substituted phenyl, or an optionally substituted 5- or 6-membered aromatic heterocycle comprising 1 or 2 heteroatoms independently selected from the group consisting of N and S. More preferably, $R^1$ is an optionally substituted phenyl, or an optionally substituted 5- or 6-membered aromatic heterocycle selected from the group consisting of pyridinyl (for example pyridin-2-yl, pyridin-3-yl or pyridin-4-yl), pyrimidinyl, pyrazinyl, thiazolyl (for example 1,3-thiazol-2-yl, 1,3-thiazol-4-yl, or 1,3-thiazol-5-yl) and isothiazolyl (i.e. 1,2-thiazolyl, for example isothiazol-3-yl (i.e. 1,2-thiazol-3-yl), isothiazol-4-yl (i.e. 1,2-thiazol-4-yl), or isothiazol-5-yl (i.e. 1,2-thiazol-5-yl)). Even more preferably, $R^1$ is an optionally substituted phenyl, and most preferably $R^1$ is a substituted phenyl.

In one preferred embodiments, $R^1$ is an optionally substituted phenyl, or an optionally substituted 5- or 6-membered aromatic heterocycle comprising 1, 2 or 3 heteroatoms independently selected from the group consisting of N, S and O, wherein said phenyl is optionally substituted with 1, 2 or 3 substituents, each substituent being independently selected from the group consisting of fluorine, meta-chlorine (meta-Cl), para-chorine (para-Cl), OH, $C_{1-8}$-alkyl, $C_{1-8}$-alkyl substituted with 1, 2 or 3 halogens or OH groups, $OC_{1-8}$-alkyl, and $OC_{1-8}$-alkyl substituted with 1, 2 or 3 halogens or OH groups, and wherein said 5- or 6-membered aromatic heterocycle is optionally substituted with 1, 2 or 3 substituents, each substituent being independently selected from the group consisting of halogen, OH, $C_{1-8}$alkyl, $C_{1-8}$alkyl substituted with 1, 2 or 3 halogens or OH groups, $OC_{1-8}$-alkyl, and $OC_{1-8}$-alkyl substituted with 1, 2 or 3 halogens or OH groups.

In another preferred embodiments, $R^1$ is an optionally substituted phenyl, or an optionally substituted 5- or 6-membered aromatic heterocycle comprising 1, 2 or 3 heteroatoms independently selected from the group consisting of N, S and O, wherein said phenyl is optionally substituted with 1, 2 or 3 substituents, each substituent being independently selected from the group consisting of fluorine, OH, $C_{1-8}$-alkyl, $C_{1-8}$-alkyl substituted with 1, 2 or 3 halogens or OH groups, $OC_{1-8}$-alkyl, and $OC_{1-8}$-alkyl substituted with 1, 2 or 3 halogens or OH groups, and wherein said 5- or 6-membered aromatic heterocycle is optionally substituted with 1, 2 or 3 substituents, each substituent being independently selected from the group consisting of halogen, OH, $C_{1-8}$-alkyl, $C_{1-8}$-alkyl substituted with 1, 2 or 3 halogens or OH groups, $OC_{1-8}$-alkyl, and $OC_{1-8}$-alkyl substituted with 1, 2 or 3 halogens or OH groups.

In embodiments where $R^1$ is an optionally substituted phenyl, said phenyl may be substituted with 1, 2 or 3 substituents, each substituent being independently selected from the group consisting of halogen, OH, $C_{1-8}$-alkyl, $C_{1-8}$-alkyl substituted with 1, 2 or 3 halogens or OH groups, $OC_{1-8}$-alkyl, and $OC_{1-8}$-alkyl substituted with 1, 2 or 3 halogens or OH groups. In certain embodiments where $R^1$ is an optionally substituted phenyl, said phenyl may be substituted with 1, 2 or 3 substituents, each substituent being independently selected from the group consisting of halogen, OH, $C_{1-8}$-alkyl, $C_{1-8}$alkyl substituted with 1, 2 or 3 halogens, $OC_{1-8}$alkyl, and $OC_{1-8}$alkyl substituted with 1, 2 or 3 halogens.

Preferably, when $R^1$ is an optionally substituted phenyl, it may be substituted with 1, 2 or 3 substituents, each substituent being independently selected from the group consisting of halogen (preferably F or Cl), $C_{1-8}$-alkyl, $C_{1-8}$-alkyl substituted with 1, 2 or 3 halogens (preferably F) or OH groups, $OC_{1-8}$-alkyl, and $OC_{1-8}$-alkyl substituted with 1, 2 or 3 halogens (preferably F) or OH groups. More preferably, when $R^1$ is an optionally substituted phenyl, it may be substituted with 1 or 2 substituents, each substituent being independently selected from the group consisting of $C_{1-4}$alkyl (e.g. methyl), $C_{1-4}$alkyl substituted with 1, 2 or 3 halogens (preferably F, e.g. $CF_3$) or OH groups (preferably 1 OH group, e.g $CH_2H$), $OC_{1-4}$alkyl (e.g. methoxy), and $OC_{1-4}$alkyl substituted with 1, 2 or 3 halogens (preferably F, e.g. $OCF_3$) or OH groups.

In another preferred embodiment, when $R^1$ is an optionally substituted phenyl, it may be substituted with 1, 2 or 3 substituents, each substituent being independently selected from the group consisting of F, meta-Cl, para-Cl, $C_{1-8}$-alkyl, $C_{1-8}$alkyl substituted with 1, 2 or 3 halogens (preferably F) or OH groups, $OC_{1-8}$-alkyl, and $OC_{1-8}$-alkyl substituted with 1, 2 or 3 halogens (preferably F) or OH groups. More preferably, when $R^1$ is an optionally substituted phenyl, it may be substituted with 1 or 2 substituents, each substituent being independently selected from the group consisting of $C_{1-4}$alkyl (e.g. methyl), $C_{1-4}$alkyl substituted with 1, 2 or 3 halogens (preferably F, e.g. $CF_3$) or OH groups (preferably 1 OH group, e.g $CH_2OH$), $OC_{1-4}$ alkyl (e.g. methoxy), and $OC_{1-4}$-alkyl substituted with 1, 2 or 3 halogens (preferably F, e.g. $OCF_3$) or OH groups.

In another embodiment, when $R^1$ is an optionally substituted phenyl, it may be substituted with 1, 2 or 3 substituents, each substituent being independently selected from the group consisting of halogen (preferably F or Cl), $C_{1-8}$-alkyl, $C_{1-8}$-alkyl substituted with 1, 2 or 3 halogens (preferably F), $OC_{1-8}$-alkyl, and $OC_{1-8}$-alkyl substituted with 1, 2 or 3 halogens (preferably F). More preferably, when $R^1$ is an optionally substituted phenyl, it may be substituted with 1 or 2 substituents, each substituent being independently selected from the group consisting of $C_{1-4}$alkyl (e.g. methyl), $C_{1-4}$alkyl substituted with 1, 2 or 3 halogens (preferably F, e.g. $CF_3$), $OC_{1-4}$alkyl (e.g. methoxy), and $OC_{1-4}$-alkyl substituted with 1, 2 or 3 halogens (preferably F, e.g. $OCF_3$).

In another preferred embodiment, when $R^1$ is an optionally substituted phenyl, it may be substituted with 1 or 2 substituents, each substituent being independently selected from the group consisting of halogen (e.g. F or Cl), $C_{1-4}$alkyl (e.g. methyl), $C_{1-4}$alkyl substituted with 1, 2 or 3 halogens (preferably F, e.g. $CF_3$) or OH groups (preferably 1 OH group, e.g. $CH_2OH$), and $OC_{1-4}$alkyl (e.g. methoxy). Even more preferably each substituent is independently selected from the group consisting of halogen (e.g. F or Cl), $C_{1-4}$alkyl, $C_{1-4}$alkyl substituted with 1 OH group, and $OC_{1-4}$alkyl (for example F, C, methyl, $CH_2OH$, or methoxy).

In another preferred embodiment, when $R^1$ is an optionally substituted phenyl, it may be substituted with 1 or 2 substituents, each substituent being independently selected from the group consisting of F, meta-Cl, para-Cl, $C_{1-4}$alkyl (e.g. methyl), $C_{1-4}$alkyl substituted with 1, 2 or 3 halogens (preferably F, e.g. $CF_3$) or OH groups (preferably 1 OH group, e.g. $CH_2H$), and $OC_{1-4}$alkyl (e.g. methoxy). For example, each substituent is independently selected from the group consisting of F, $C_{1-4}$alkyl (e.g. methyl), $C_{1-4}$alkyl substituted with 1, 2 or 3 halogens (preferably F, e.g. $CF_3$) or OH groups (preferably 1 OH group, e.g. $CH_2H$), and $OC_{1-4}$alkyl (e.g. methoxy). Even more preferably each substituent is independently selected from the group consisting of F, meta-Cl, para-Cl, $C_{1-4}$alkyl, $C_{1-4}$alkyl substituted with 1 OH group, and $OC_{1-4}$-alkyl (for example F, C, methyl, $CH_2H$, or methoxy). For example, each substituent is independently selected from the group consisting of F, $C_{1-4}$alkyl, $C_{1-4}$alkyl substituted with 1 OH group, and $OC_{1-4}$alkyl (for example F, Cl, methyl, $CH_2OH$, or methoxy).

In another preferred embodiment, when $R^1$ is an optionally substituted phenyl, it may be substituted with 1 or 2 substituents, each substituent being independently selected from the group consisting of halogen (e.g. F or Cl), $C_{1-4}$alkyl (e.g. methyl), $C_{1-4}$alkyl substituted with 1, 2 or 3 halogens (preferably F, e.g. $CF_3$), and $OC_{1-4}$alkyl (e.g. methoxy). Even more preferably each substituent is independently selected from the group consisting of halogen (e.g. F or Cl), $C_{2-4}$alkyl, and $OC_{1-4}$alkyl (for example F, C, methyl or methoxy).

In another preferred embodiment, when $R^1$ is an optionally substituted phenyl, it may be substituted with 1 or 2 substituents, each substituent being independently selected from the group consisting of halogen (e.g. F or C, preferably F), $C_{1-4}$alkyl (e.g. methyl), $C_{1-4}$alkyl substituted with 1, 2 or 3 halogens (preferably F, e.g. $CF_3$) or OH groups (preferably 1 OH group, e.g $CH_2OH$), and $OC_{1-4}$-alkyl (e.g. methoxy). Even more preferably each substituent is independently selected from the group consisting of F, C, $C_{1-4}$alkyl, $C_{1-4}$alkyl substituted with 1, 2 or 3 fluorines (e.g. $CF_3$) or OH groups (preferably 1 OH group, e.g $CH_2H$), and $OC_{1-4}$alkyl (for example Cl, methyl, $CF_3$, $CH_2OH$ or methoxy).

In another preferred embodiment, when $R^1$ is an optionally substituted phenyl, it may be substituted with 1 or 2 substituents, each substituent being independently selected from the group consisting of halogen (e.g. F or C, preferably F), $C_{1-4}$alkyl (e.g. methyl), C-alkyl substituted with 1, 2 or 3 halogens (preferably F, e.g. $CF_3$), and $OC_{1-4}$alkyl (e.g. methoxy). Even more preferably each substituent is independently selected from the group consisting of F, Cl, $C_{1-4}$alkyl, $C_{1-4}$alkyl substituted with 1, 2 or 3 fluorines (e.g. $CF_3$), and $OC_{1-4}$alkyl (for example Cl, methyl, $CF_3$ or methoxy).

In another preferred embodiment, when $R^1$ is an optionally substituted phenyl, it may be substituted with 1 or 2 substituents, each substituent being independently selected from the group consisting of halogen (e.g. F or Cl), $C_{1-4}$alkyl (e.g. methyl), $C_{1-4}$alkyl (e.g. methyl) substituted with 1, 2 or 3 OH groups (preferably 1 OH group, e.g $CH_2H$), $OC_{1-4}$alkyl (e.g. methoxy) and $OC_{1-4}$-alkyl substituted with 1, 2 or 3 halogens (preferably F, e.g. $OCF_3$) or OH groups (preferably 1 OH group). Even more preferably each substituent is independently selected from the group consisting of C, $C_{1-4}$alkyl, $C_{1-4}$alkyl substituted with 1 OH group, $OC_{1-4}$ alkyl, and $OC_{1-4}$-alkyl substituted with 1, 2 or 3 fluorines (e.g. $OCF_3$) (for example C, methyl, $CH_2H$, $OCF_3$ or methoxy). Even more preferably each substituent is independently selected from the group consisting of $C_{1-4}$alkyl, $C_{1-4}$alkyl substituted with 1 OH group, $OC_{1-4}$alkyl, and $OC_{1-4}$alkyl substituted with 1, 2 or 3 fluorines (e.g. $OCF_3$) (for example methyl, $CH_2OH$, $OCF_3$ or methoxy).

In another preferred embodiment, when $R^1$ is an optionally substituted phenyl, it may be substituted with 1 or 2 substituents, each substituent being independently selected from the group consisting of halogen (e.g. F or Cl), $C_{1-4}$alkyl (e.g. methyl), $OC_{1-4}$alkyl (e.g. methoxy) and $OC_{1-4}$alkyl substituted with 1, 2 or 3 halogens (preferably F, e.g. $OCF_3$). Even more preferably each substituent is independently selected from the group consisting of Cl, $C_{1-4}$ alkyl, $OC_{1-4}$-alkyl, and $OC_{1-4}$alkyl substituted with 1, 2 or 3 fluorines (e.g. $OCF_3$) (for example C, methyl, $OCF_3$ or methoxy).

In embodiments where $R^1$ is an optionally substituted phenyl, it is preferred that the phenyl is substituted, i.e. it is preferred that $R^1$ is a substituted phenyl, said phenyl substituted with the substituents listed in said embodiment.

In certain preferred embodiments, when $R^1$ is an optionally substituted phenyl, it may be substituted with 1 substituent selected from the group consisting of $C_{1-8}$alkyl (preferably $C_{1-4}$ alkyl, e.g. methyl), $C_{1-8}$alkyl substituted with 1, 2 or 3 halogens or OH groups (preferably $C_{1-4}$alkyl substituted with 1, 2 or 3 halogens, e.g. $CF_3$, or 1, 2 or 3 OH groups, e.g. $CH_2OH$), $OC_{1-8}$alkyl (preferably $OC_{1-4}$alkyl, e.g. methoxy), $OC_{1-8}$alkyl substituted with 1, 2 or 3 halogens or OH groups (preferably $OC_{1-4}$alkyl substituted with 1, 2 or 3 halogens, e.g. $OCF_3$), and halogen (e.g. F or Cl).

In certain very preferred embodiments, when $R^1$ is an optionally substituted phenyl, it may be substituted with 1 substituent selected from the group consisting of ortho, meta or para $C_{1-8}$alkyl (preferably $C_{1-4}$alkyl, e.g. methyl), meta $C_{1-8}$alkyl substituted with 1, 2 or 3 halogens or OH groups (preferably $C_{1-4}$alkyl substituted with 1, 2 or 3 halogens, e.g. $CF_3$, or 1, 2 or 3 OH groups, e.g. $CH_2OH$), ortho or meta $OC_{1-8}$alkyl (preferably $OC_{1-4}$alkyl, e.g. methoxy), meta $OC_{1-8}$alkyl substituted with 1, 2 or 3 halogens (preferably $OC_{1-4}$alkyl substituted with 1, 2 or 3 halogens, e.g. $OCF_3$), and meta halogen (e.g. F or Cl).

In certain preferred embodiments, when $R^1$ is an optionally substituted phenyl, it may be substituted with 1 substituent selected from the group consisting of $C_{1-8}$alkyl (preferably $C_{1-4}$alkyl, e.g. methyl), $C_{1-8}$alkyl substituted with 1, 2 or 3 halogens or OH groups (preferably $C_{1-4}$alkyl substituted with 1, 2 or 3 halogens, e.g. $CF_3$, or 1, 2 or 3 OH groups, e.g. $CH_2OH$), $OC_{1-8}$alkyl (preferably $OC_{1-4}$alkyl, e.g. methoxy), $OC_{1-8}$alkyl substituted with 1, 2 or 3 halogens or OH groups (preferably $OC_{1-4}$alkyl substituted with 1, 2 or 3 halogens, e.g. $OCF_3$), and F.

In certain preferred embodiments, when $R^1$ is an optionally substituted phenyl, it may be substituted with 1 substituent selected from the group consisting of $C_{1-8}$alkyl (preferably $C_{1-4}$alkyl, e.g. methyl), $C_{1-8}$alkyl substituted with 1, 2 or 3 halogens ($C_1$-preferably $C_{1-4}$alkyl substituted with 1, 2 or 3 halogens, e.g. $CF_3$), $OC_{1-8}$alkyl (preferably $OC_{1-4}$alkyl, e.g. methoxy), $OC_{1-8}$alkyl substituted with 1, 2 or 3 halogens (preferably $OC_{1-4}$alkyl substituted with 1, 2 or 3 halogens, e.g. $OCF_3$), and halogen (e.g. F or Cl); and more preferably ortho, meta or para $C_{1-8}$alkyl (preferably $C_{1-4}$alkyl, e.g. methyl), meta $C_{1-8}$alkyl substituted with 1, 2 or 3 halogens (preferably $C_{1-4}$alkyl substituted with 1, 2 or 3 halogens, e.g. $CF_3$), ortho or meta $OC_{1-8}$alkyl (preferably $OC_{1-4}$alkyl, e.g. methoxy), meta $OC_{1-8}$alkyl substituted with 1, 2 or 3 halogens (preferably $OC_{1-4}$alkyl substituted with 1, 2 or 3 halogens, e.g. $OCF_3$), and meta halogen (e.g. F or Cl).

In certain other preferred embodiments, when $R^1$ is an optionally substituted phenyl, it may be substituted with 1 substituent selected from the group consisting of $C_{1-8}$alkyl (preferably $C_{1-4}$alkyl, e.g. methyl), $C_{1-8}$alkyl substituted with 1, 2 or 3 halogens or OH groups (preferably $C_{1-4}$alkyl substituted with 1, 2 or 3 halogens, e.g. $CF_3$, or 1, 2 or 3 OH groups, e.g. $CH_2OH$) and $OC_{1-8}$alkyl substituted with 1, 2 or 3 halogens or OH groups (preferably $OC_{1-4}$alkyl substituted with 1, 2 or 3 halogens, e.g. $OCF_3$). In certain other preferred embodiments, when $R^1$ is an optionally substituted phenyl, it may be substituted with 1 substituent selected from the group consisting of $C_{1-8}$alkyl (preferably $C_{1-4}$alkyl, e.g. methyl), $C_{1-8}$alkyl substituted with 1, 2 or 3 OH groups (preferably $C_{1-4}$alkyl substituted with 1 OH group, e.g. $CH_2OH$), and $OC_{1-8}$alkyl (preferably $OC_{1-4}$alkyl, e.g. methoxy).

In certain other preferred embodiments, when $R^1$ is an optionally substituted phenyl, it may be substituted with 1 substituent selected from the group consisting of $C_{1-8}$alkyl (preferably $C_{1-4}$alkyl, e.g. methyl), $C_{1-8}$alkyl substituted with 1, 2 or 3 halogens (preferably $C_{1-4}$alkyl substituted with 1, 2 or 3 halogens, e.g. $CF_3$) and $OC_{1-8}$alkyl substituted with 1, 2 or 3 halogens (preferably $OC_{1-4}$alkyl substituted with 1, 2 or 3 halogens, e.g. $OCF_3$). In certain other preferred embodiments, when $R^1$ is an optionally substituted phenyl, it may be substituted with 1 substituent selected from the group consisting of $C_{1-8}$alkyl (preferably $C_{1-4}$ alkyl, e.g. methyl) and $OC_{1-8}$alkyl (preferably $OC_{1-4}$alkyl, e.g. methoxy).

In certain preferred embodiments, when $R^1$ is an optionally substituted phenyl, it may be substituted with 2 substituents selected from the group consisting of halogen, $C_{1-8}$alkyl (preferably F and $C_{1-4}$alkyl, e.g. F and methyl) and $C_{1-8}$alkyl substituted with 1, 2 or 3 OH groups (preferably 1 OH group, e.g. $CH_2OH$); $C_{1-8}$alkyl and $C_{1-8}$alkyl (preferably $C_{1-4}$alkyl and $C_{1-4}$alkyl, e.g. methyl and methyl); or $C_{1-8}$alkyl and $C_{1-8}$alkyl substituted with 1, 2 or 3 OH groups (preferably 1 OH group, e.g. $CH_2OH$) (preferably $C_{1-4}$alkyl and $C_{1-4}$alkyl substituted with 1, 2 or 3 OH groups (preferably 1 OH group), e.g. methyl and $CH_2OH$). In another preferred embodiment, when $R^1$ is an optionally substituted phenyl, it may be substituted with 2 substituents selected from the group consisting of: halogen and halogen (e.g. C and Cl); $C_{1-8}$alkyl and $C_{1-8}$alkyl (preferably $C_{1-4}$alkyl and $C_{1-4}$alkyl, e.g. methyl and methyl); and $C_{1-8}$alkyl and $C_{1-8}$alkyl substituted with 1, 2 or 3 halogens or OH groups (preferably $C_{1-4}$alkyl and $C_{1-4}$alkyl substituted with 1, 2 or 3 halogens or OH groups, e.g. methyl and $CF_3$, or methyl and $CH_2H$). In another preferred embodiment, when $R^1$ is an optionally substituted phenyl, it may be substituted with 2 substituents selected from the group consisting of: $C_{1-8}$alkyl and $C_{1-8}$alkyl (preferably $C_{1-4}$alkyl and $C_{1-4}$alkyl, e.g. methyl and methyl); and $C_{1-8}$alkyl and $C_{1-8}$alkyl substituted with 1, 2 or 3 halogens or OH groups (preferably $C_{1-4}$alkyl and $C_{1-4}$alkyl substituted with 1, 2 or 3 halogens or OH groups, e.g. methyl and $CF_3$, or methyl and $CH_2OH$).

In another preferred embodiments, when $R^1$ is an optionally substituted phenyl, it may be substituted with 2 substituents selected from the group consisting of F, $C_{1-4}$alkyl (preferably F and $C_{1-4}$alkyl, e.g. F and methyl) and $C_{1-8}$alkyl substituted with 1, 2 or 3 OH groups (preferably 1 OH group, e.g. $CH_2OH$); $C_{1-8}$-alkyl and C-alkyl (preferably $C_{1-4}$alkyl and $C_{1-4}$alkyl, e.g. methyl and methyl); or $C_{1-8}$alkyl and $C_{1-8}$alkyl substituted with 1, 2 or 3 OH groups (preferably 1 OH group, e.g. $CH_2OH$) (preferably $C_{1-4}$alkyl and $C_{1-4}$alkyl substituted with 1, 2 or 3 OH groups (preferably 1 OH group), e.g. methyl and $CH_2OH$). In another preferred embodiment, when $R^1$ is an optionally substituted phenyl, it may be substituted with 2 substituents selected from the group consisting of: F and F; $C_{1-8}$-alkyl and $C_{1-8}$-alkyl (preferably $C_{1-4}$alkyl and $C_{1-4}$alkyl, e.g. methyl and methyl); and $C_{1-8}$alkyl and $C_{1-8}$alkyl substituted with 1, 2 or 3 halogens or OH groups (preferably $C_{1-4}$alkyl and $C_{1-4}$alkyl substituted with 1, 2 or 3 halogens or OH groups, e.g. methyl and $CF_3$, or methyl and $CH_2OH$). In another preferred embodiment, when $R^1$ is an optionally substituted phenyl, it may be substituted with 2 substituents selected from the group consisting of: $C_{1-8}$alkyl and $C_{1-8}$alkyl (preferably $C_{1-4}$alkyl and $C_{1-4}$alkyl, e.g. methyl and methyl); and $C_{1-8}$alkyl and $C_{1-8}$alkyl substituted with 1, 2 or 3 halogens or OH groups (preferably $C_{1-4}$alkyl and $C_{1-4}$alkyl substituted with 1, 2 or 3 halogens or OH groups, e.g. methyl and $CF_3$, or methyl and $CH_2OH$).

In certain preferred embodiments, when $R^1$ is an optionally substituted phenyl, it may be substituted with 2 substituents selected from the group consisting of halogen and $C_{1-8}$alkyl (preferably F and $C_{1-4}$-alkyl, e.g. F and methyl); and $C_{1-8}$-alkyl and $C_{1-8}$-alkyl (preferably $C_{1-4}$alkyl and $C_{1-4}$alkyl, e.g. methyl and methyl). In another preferred embodiment, when $R^1$ is an optionally substituted phenyl, it may be substituted with 2 substituents selected from the group consisting of: halogen and halogen (e.g. C and Cl); $C_{1-8}$alkyl and $C_{1-8}$alkyl (preferably $C_{1-4}$alkyl and $C_{1-4}$alkyl, e.g. methyl and methyl); and $C_{1-8}$alkyl and $C_{1-8}$alkyl substituted with 1, 2 or 3 halogens (preferably $C_{1-4}$alkyl and $C_{1-4}$alkyl substituted with 1, 2 or 3 halogens, e.g. methyl and $CF_3$). In another preferred embodiment, when $R^1$ is an optionally substituted phenyl, it may be substituted with 2 substituents selected from the group consisting of: $C_{1-8}$alkyl and $C_{1-8}$-alkyl (preferably $C_{1-4}$alkyl and $C_{1-4}$alkyl, e.g. methyl and methyl); and $C_{1-8}$alkyl and $C_{1-8}$-alkyl substituted with 1, 2 or 3 halogens (preferably $C_{1-4}$alkyl and $C_{1-4}$alkyl substituted with 1, 2 or 3 halogens, e.g. methyl and $CF_3$).

In another embodiment, when $R^1$ is an optionally substituted phenyl, it may be substituted with 2 substituents that are and $C_{1-8}$alkyl and $C_{1-8}$alkyl substituted with 1, 2 or 3 halogens or OH groups (preferably $C_{1-4}$alkyl and C-alkyl substituted with 1, 2 or 3 halogens or OH groups, e.g. methyl and $CF_3$, or methyl and $CH_2OH$). In another embodiment, when $R^1$ is an optionally substituted phenyl, it may be substituted with 2 substituents that are and $C_{1-8}$alkyl substituted with 1, 2 or 3 OH groups and $C_{1-8}$-alkyl substituted with 1, 2 or 3 OH groups (preferably $C_{1-4}$alkyl substituted with 1, 2 or 3 OH groups (preferably 1 OH group) and $C_{1-4}$ alkyl substituted with 1, 2 or 3 OH groups (preferably 1 OH group), e.g. $CH_2OH$ and $CH_2OH$).

In another embodiment, when $R^1$ is an optionally substituted phenyl, it may be substituted with 2 substituents that are and $C_{1-8}$alkyl and $C_{1-8}$alkyl substituted with 1, 2 or 3 halogens (preferably $C_{1-4}$alkyl and $C_{1-4}$alkyl substituted with 1, 2 or 3 halogens, e.g. methyl and $CF_3$).

When $R^1$ is an optionally substituted 5- or 6-membered aromatic heterocycle, the heterocycle may be unsubstituted. Alternatively, it may be substituted. When it is substituted, it may be substituted with 1, 2 or 3 substituents, each substituent being independently selected from the group consisting of halogen, OH, $C_{1-8}$-alkyl, $C_{1-8}$-alkyl substituted with 1, 2 or 3 halogens or OH groups, $OC_{1-8}$-alkyl, and $OC_{1-8}$alkyl substituted with 1, 2 or 3 halogens or OH groups. Preferably, each substituent may be independently selected from the group consisting of halogen (preferably F or Cl), $C_{1-8}$-alkyl, $C_{1-8}$-alkyl substituted with 1, 2 or 3 halogens (preferably F) or OH groups (preferably 1 OH group, e.g $CH_2H$), $OC_{1-8}$-alkyl, and $OC_{1-8}$-alkyl substituted with 1, 2 or 3 halogens (preferably F) or OH groups (preferably 1 OH group, e.g $CH_2OH$). More preferably, it may be substituted with 1 or 2 substituents, each substituent being independently selected from the group consisting of $C_{1-4}$alkyl, $C_{1-4}$alkyl substituted with 1, 2 or 3 halogens (preferably F) or OH groups (preferably 1 OH group, e.g $CH_2OH$), $OC_{1-4}$alkyl, and $OC_{1-4}$alkyl substituted with 1, 2 or 3 halogens (preferably F) or OH groups (preferably 1 OH group, e.g $CH_2OH$).

When $R^1$ is an optionally substituted 5- or 6-membered aromatic heterocycle, the heterocycle may be unsubstituted. Alternatively, it may be substituted. When it is substituted, it may be substituted with 1, 2 or 3 substituents, each substituent being independently selected from the group consisting of halogen, OH, $C_{1-8}$-alkyl, $C_{1-8}$-alkyl substituted with 1, 2 or 3 halogens, $OC_{1-8}$alkyl, and $OC_{1-8}$alkyl substituted with 1, 2 or 3 halogens. Preferably, each substituent may be independently selected from the group consisting of halogen (preferably F or Cl), $C_{1-8}$alkyl, $C_{1-8}$alkyl substituted with 1, 2 or 3 halogens (preferably F), $OC_{1-8}$alkyl, and $OC_{1-8}$alkyl substituted with 1, 2 or 3 halogens (preferably F). More preferably, it may be substituted with 1 or 2 substituents, each substituent being independently selected from the group consisting of $C_{1-4}$alkyl, $C_{1-4}$alkyl substituted with 1, 2 or 3 halogens (preferably F), $OC_{1-4}$alkyl, and $OC_{1-4}$alkyl substituted with 1, 2 or 3 halogens (preferably F).

In another preferred embodiment, when $R^1$ is an optionally substituted 5- or 6-membered aromatic heterocycle, it may be substituted with 1 or 2 substituents, each substituent being independently selected from the group consisting of halogen (e.g. F or Cl), $C_{1-4}$alkyl, $C_{1-4}$alkyl substituted with 1, 2 or 3 halogens (preferably F) or OH groups (preferably 1 OH group, e.g $CH_2OH$), and $OC_{1-4}$alkyl. Even more preferably each substituent is independently selected from the group consisting of Cl, $C_{1-4}$alkyl, $C_{1-4}$alkyl substituted with 1, 2 or 3 OH groups (preferably 1 OH group, e.g $CH_2OH$), and $OC_{1-4}$alkyl. In another preferred embodiment, it may be substituted with 1 substituent selected from the group consisting of $C_{1-4}$alkyl, $C_{1-4}$ alkyl substituted with 1, 2 or 3 halogens (preferably F) or OH groups, $OC_{1-4}$-alkyl, and $OC_{1-4}$alkyl substituted with 1, 2 or 3 halogens (preferably F) or OH groups; and most preferably it may be substituted with 1 substituent that is $C_{1-4}$alkyl (preferably methyl) or $C_{1-4}$alkyl substituted with 1, 2 or 3 OH groups (preferably $CH_2OH$).

In another preferred embodiment, when $R^1$ is an optionally substituted 5- or 6-membered aromatic heterocycle, it may be substituted with 1 or 2 substituents, each substituent being independently selected from the group consisting of halogen (e.g. F or Cl), $C_{1-4}$alkyl, $C_{1-4}$alkyl substituted with 1, 2 or 3 halogens (preferably F), and $OC_{1-4}$alkyl. Even more preferably each substituent is independently selected from the group consisting of C, $C_{1-4}$alkyl, and $OC_{1-4}$ alkyl. In another preferred embodiment, it may be substituted with 1 substituent selected from the group consisting of $C_{1-4}$alkyl, $C_{1-4}$alkyl substituted with 1, 2 or 3 halogens (preferably F), $OC_{1-4}$alkyl, and $OC_{1-4}$alkyl substituted with 1, 2 or 3 halogens (preferably F); and most preferably it may be substituted with 1 substituent that is $C_{1-4}$alkyl (preferably methyl).

In certain very preferred embodiment, $R^1$ is selected from the group consisting of:

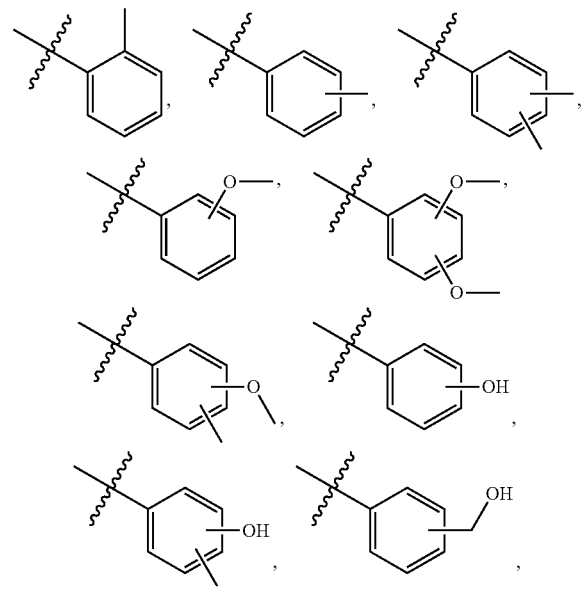

For example, $R^1$ is selected from the group consisting of:

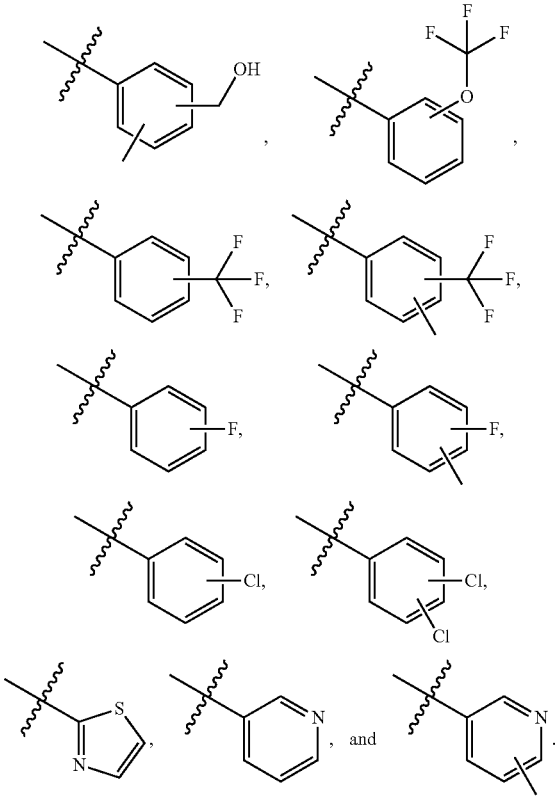

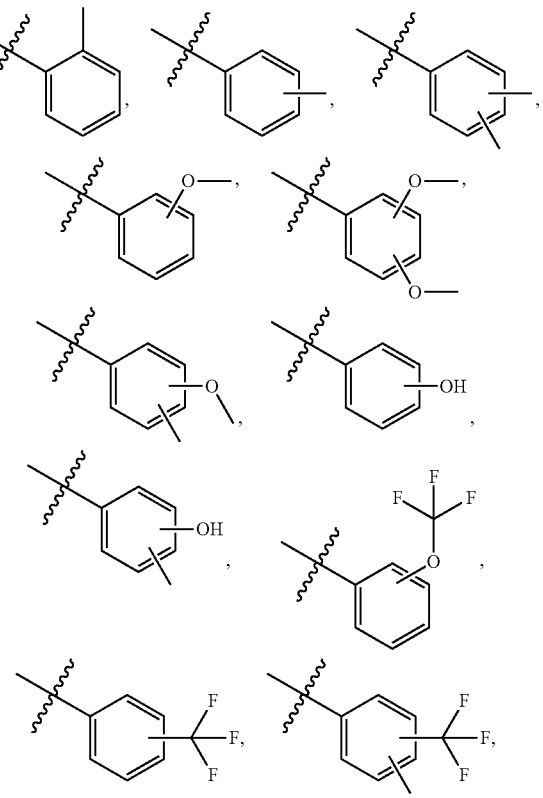

13
-continued
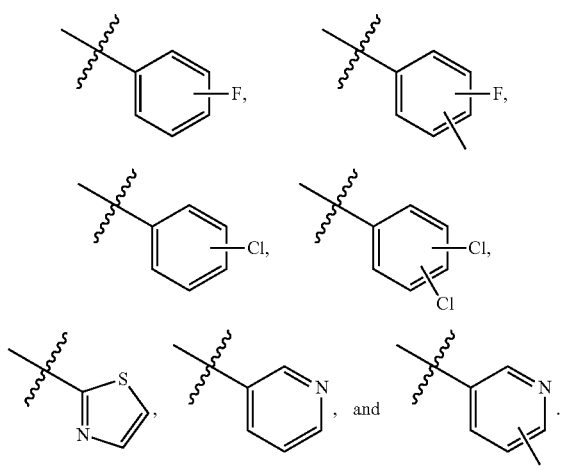
In certain very preferred embodiment, $R^1$ is selected from the group consisting of:
14
-continued
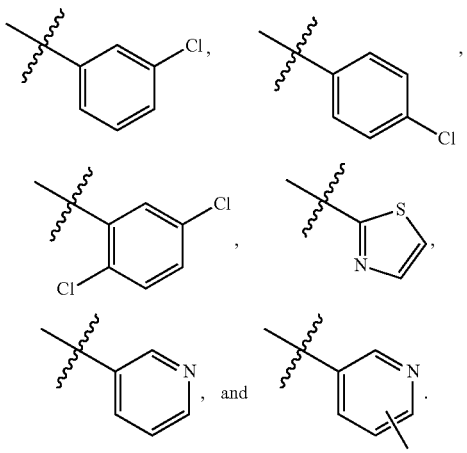
In certain very preferred embodiment, $R^1$ is selected from the group consisting of:
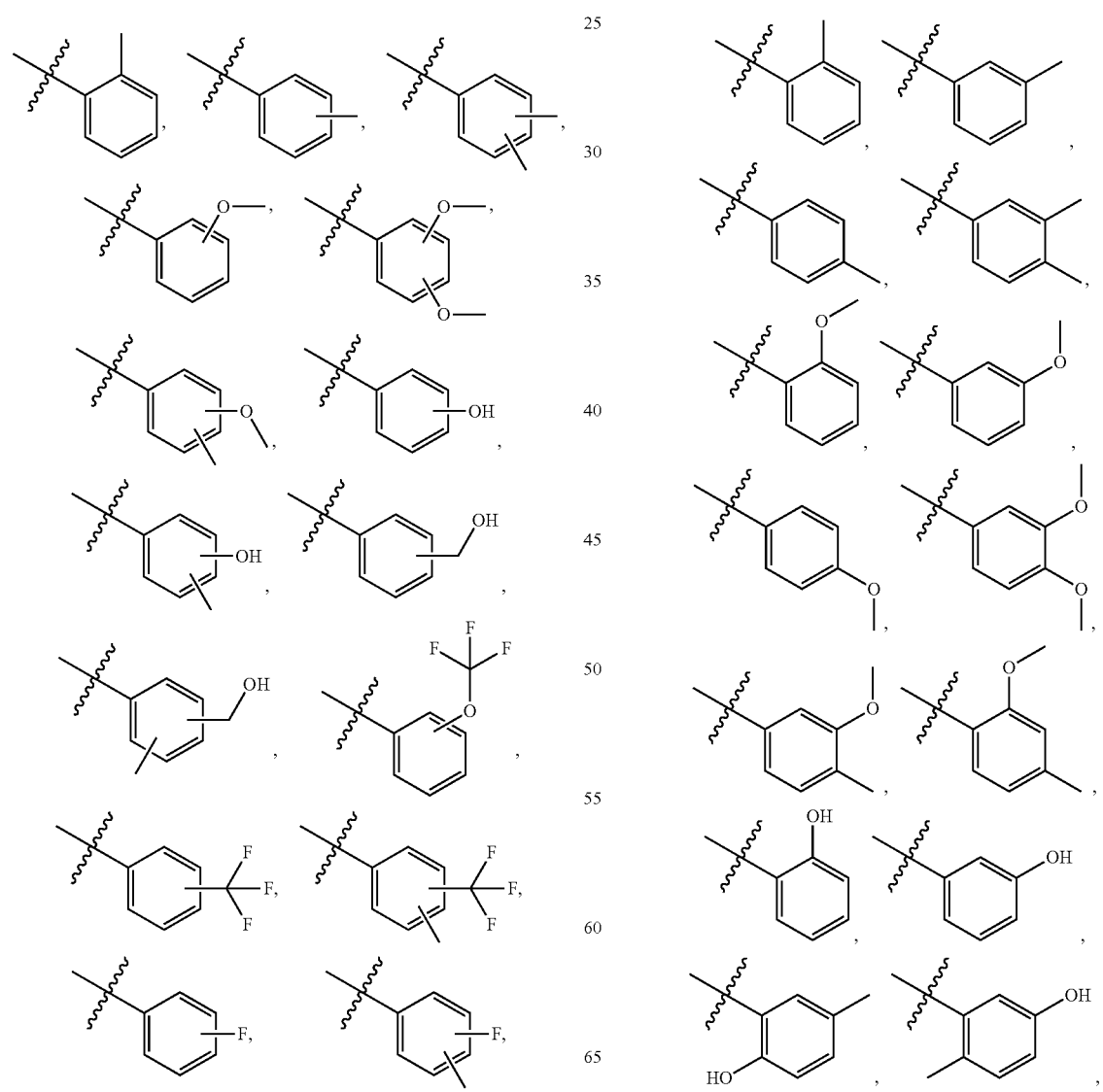

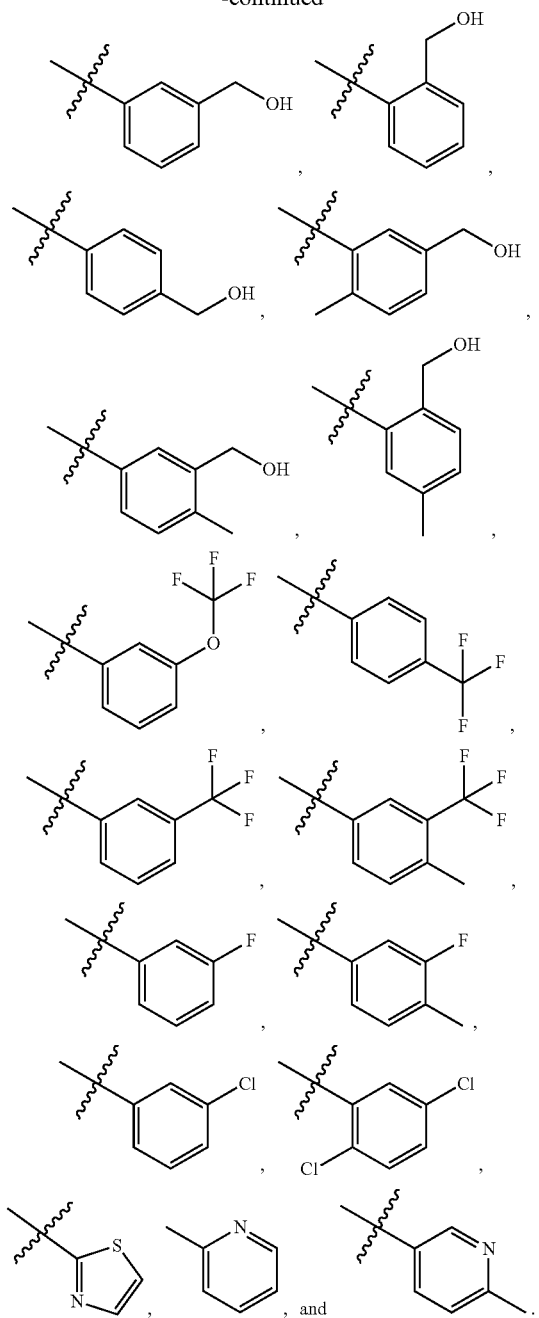
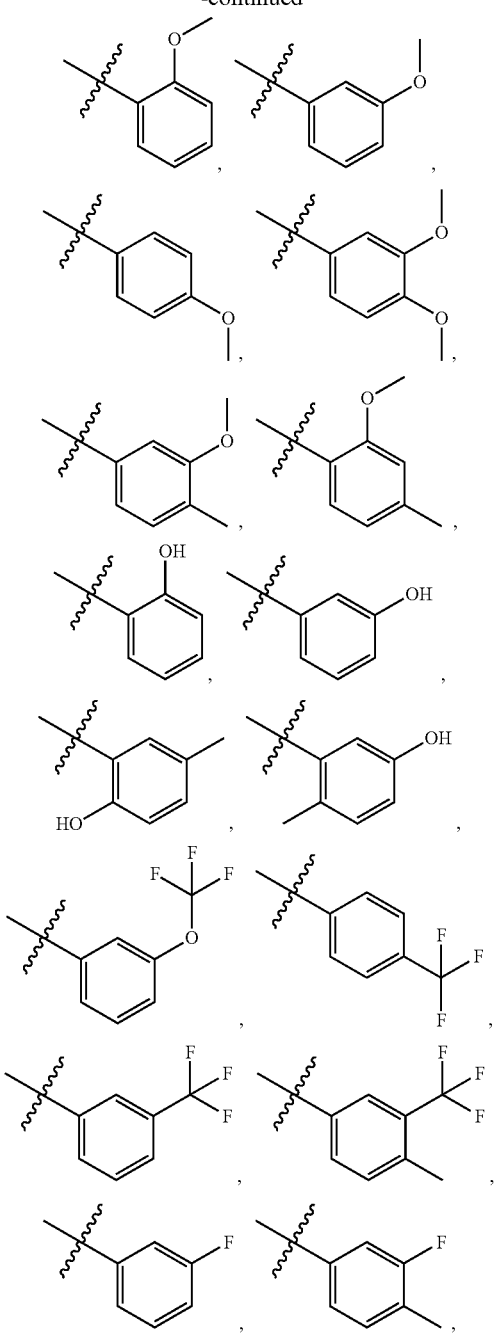
For example R¹ is selected from the group consisting of:
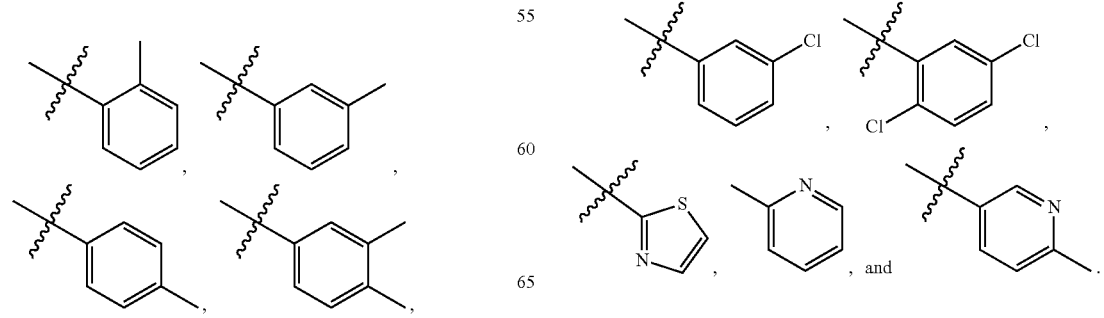

More preferably R¹ is selected from the group consisting of:
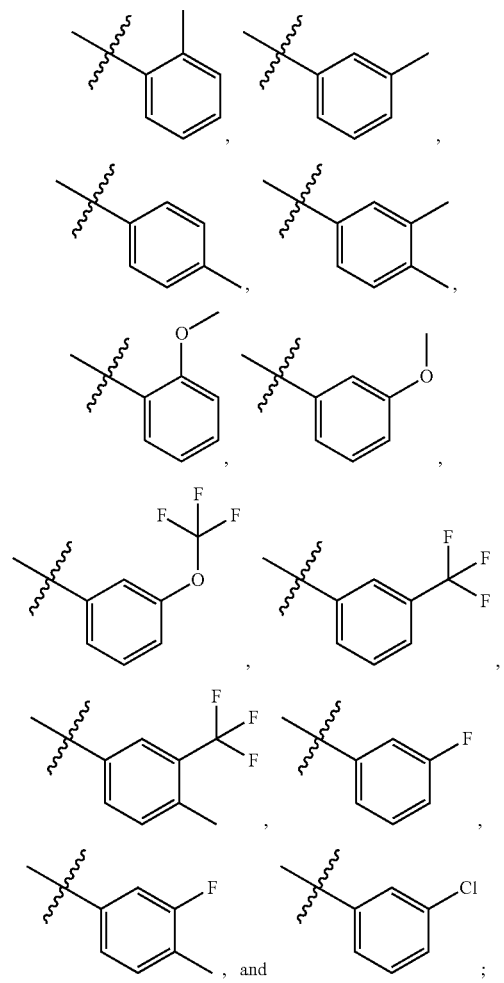
,
or selected from the group consisting of:
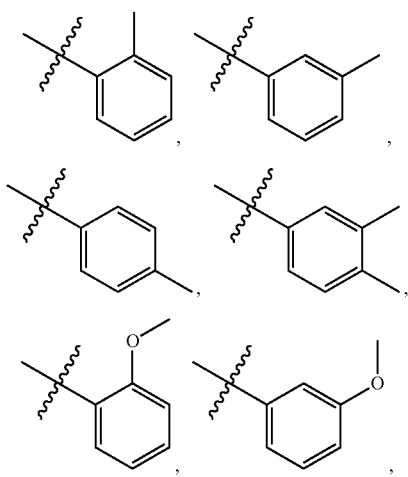
,
-continued
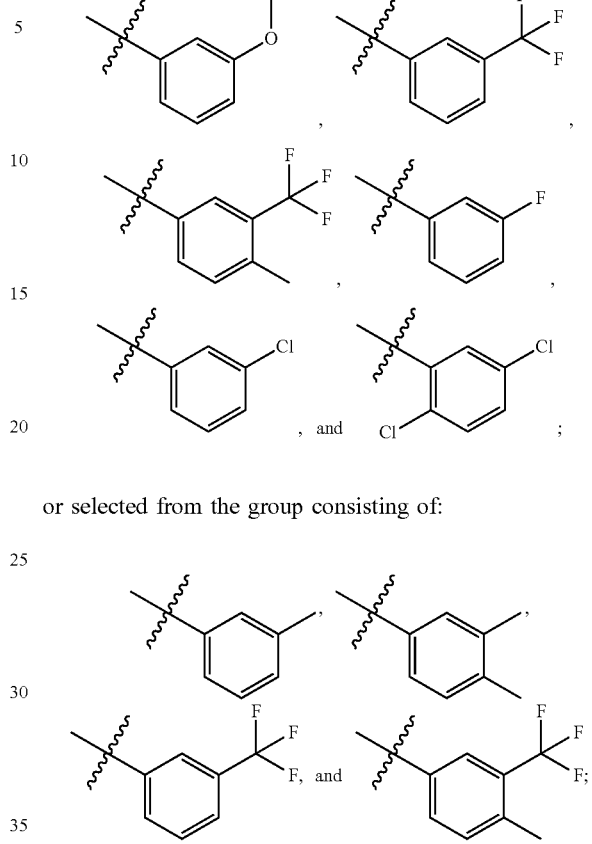
, and
;
or selected from the group consisting of:
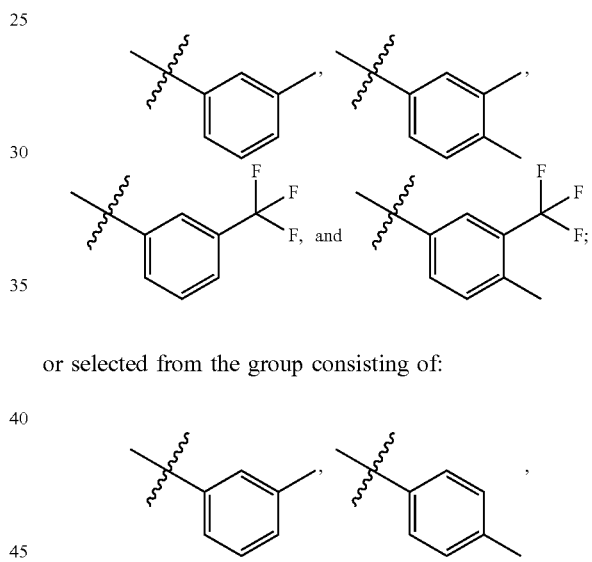
;
or selected from the group consisting of:
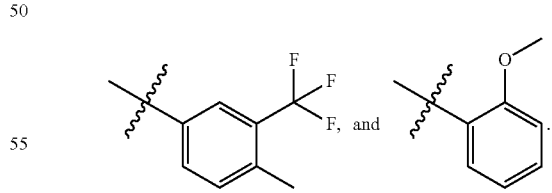
.
R¹ may also additionally be
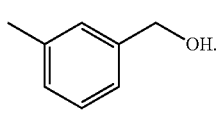

In another preferred embodiment, R¹ is

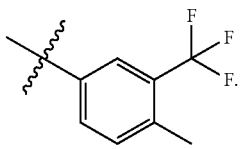 [SMILES: *c1ccc(C)c(C(F)(F)F)c1]

In another preferred embodiment, R¹ is

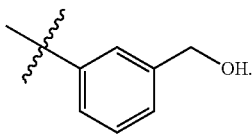 [SMILES: *c1cccc(CO)c1]

In another preferred embodiment, R¹ is

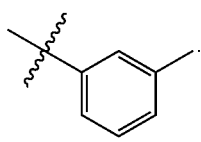 [SMILES: *c1cccc(C)c1]

In the compounds of formula (I), R² is an optionally substituted 5- or 6-membered aromatic heterocycle comprising 2 or 3 heteroatoms selected from the group consisting of N, S and O, wherein said 5- or 6-membered aromatic heterocycle is optionally substituted with 1, 2 or 3 substituents, each substituent being independently selected from the group consisting of $C_{1-3}$ alkyl and $C_{1-3}$ alkyl substituted with 1, 2 or 3 halogens.

In certain preferred embodiments R² is an optionally substituted 5- or 6-membered aromatic heterocycle comprising 2 or 3 heteroatoms independently selected from the group consisting of N, S and O, wherein at least one of the heteroatoms is N. For example, R² is an optionally substituted 5- or 6-membered aromatic heterocycle selected from the group consisting of imidazolyl (1,3-diazolyl), pyrazolyl (1,2-diazolyl), 1,3-oxazolyl, isoxazolyl (1,2-oxazolyl), thiazolyl (1,3-thiazolyl, preferably 1,3-thiazol-2-yl), isothiazolyl (1,2-thiazolyl), 1H-1,2,3-triazolyl, 2H-1,2,3-triazolyl, 1H-1,2,4-triazolyl, 4H-1,2,4-triazolyl, furazanyl (1,2,5-oxadiazolyl), 1,2,3-oxadiazolyl, 1,2,4-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), pyrazinyl (1,4-diazinyl), 1,2,3-triazinyl, 1,2,4-triazinyl, and 1,3,5-triazinyl.

In certain preferred embodiments R² is an optionally substituted 5- or 6-membered aromatic heterocycle comprising 2 or 3 heteroatoms independently selected from the group consisting of N, S and O, wherein at least one of the heteroatoms is N and at least one of the heteroatoms is S. In another preferred embodiment, R² is an optionally substituted 5- or 6-membered aromatic heterocycle comprising 2 or 3 heteroatoms independently selected from the group consisting of N, S and O, wherein at least two of the heteroatoms are N.

In one preferred embodiment, R² is an optionally substituted 5- or 6-membered aromatic heterocycle comprising 2 or 3 heteroatoms independently selected from the group consisting of N and S; and even more preferably at least one of the heteroatoms is N (for example, at least one of the heteroatoms is N and at least one of the heteroatoms is S). For example, R² is an optionally substituted 5- or 6-membered aromatic heterocycle selected from the group consisting of imidazolyl (1,3-diazolyl), pyrazolyl (1,2-diazolyl), thiazolyl (1,3-thiazolyl, preferably 1,3-thiazol-2-yl), isothiazolyl (1,2-thiazolyl), 1H-1,2,3-triazolyl, 2H-1,2,3-triazolyl, 1H-1,2,4-triazolyl, 4H-1,2,4-triazolyl, 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), pyrazinyl (1,4-diazinyl), 1,2,3-triazinyl, 1,2,4-triazinyl, and 1,3,5-triazinyl.

In certain preferred embodiments R² is an optionally substituted 5- or 6-membered aromatic heterocycle comprising 2 heteroatoms independently selected from the group consisting of N, S and O. Even more preferably, at least one of the heteroatoms is N. For example, R² is an optionally substituted 5- or 6-membered aromatic heterocycle selected from the group consisting of imidazolyl (1,3-diazolyl), pyrazolyl (1,2-diazolyl), 1,3-oxazolyl, isoxazolyl (1,2-oxazolyl), thiazolyl (1,3-thiazolyl, preferably 1,3-thiazol-2-yl), isothiazolyl (1,2-thiazolyl), pyridazinyl (1,2-diazinyl), pyrimidinyl (1,3-diazinyl), and pyrazinyl (1,4-diazinyl).

In another preferred embodiment, R² is an optionally substituted 5- or 6-membered aromatic heterocycle selected from the group consisting of 1,3-oxazolyl, isoxazolyl (1,2-oxazolyl), thiazolyl (1,3-thiazolyl, preferably 1,3-thiazol-2-yl), isothiazolyl (1,2-thiazolyl), 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), and pyrazinyl (1,4-diazinyl).

In another embodiment, R² is an optionally substituted 5- or 6-membered aromatic heterocycle selected from the group consisting of imidazolyl (1,3-diazolyl), pyrazol-3-yl (1,2-diazol-3-yl), pyrazol-5-yl (1,2-diazol-3-yl),), pyrazol-5-yl (1,2-diazol-3-yl), 1,3-oxazolyl (e.g. 1,3-oxazol-2-yl, 1,3-oxazol-4-yl, 1,3-oxazol-5-yl), isoxazolyl (1,2-oxazolyl), thiazolyl (1,3-thiazol-2-yl, e.g. thiazol-2-yl (1,3-thiazol-2-yl), thiazol-4-yl (1,3-thiazol-4-yl), or thiazol-5-yl (1,3-thiazol-5-yl)), isothiazolyl (1,2-thiazolyl, e.g. 1,2-thiazol-3-yl), 1H-1,2,3-triazolyl, 2H-1,2,3-triazolyl, 1H-1,2,4-triazolyl, 4H-1,2,4-triazolyl, furazanyl (1,2,5-oxadiazolyl), 1,2,3-oxadiazolyl, 1,2,4-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), pyrazinyl (1,4-diazinyl, e.g. pyrazin-2-yl), 1,2,3-triazinyl, 1,2,4-triazinyl, and 1,3,5-triazinyl (For example selected from the group consisting of imidazolyl (1,3-diazolyl), 1,3-oxazolyl, isoxazolyl (1,2-oxazolyl), isothiazolyl (1,2-thiazolyl), furazanyl (1,2,5-oxadiazolyl), 1,2,3-oxadiazolyl, 1,2,4-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), pyrazinyl (1,4-diazinyl), 1,2,3-triazinyl, 1,2,4-triazinyl, and 1,3,5-triazinyl).

Even more preferably, R² is an optionally substituted 5- or 6-membered aromatic heterocycle selected from the group consisting of 1,3-oxazolyl, isoxazolyl (1,2-oxazolyl), thiazolyl (1,3-thiazolyl, preferably 1,3-thiazol-2-yl), isothiazolyl (1,2-thiazolyl), 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), and pyrazinyl (1,4-diazinyl) (for example, selected from the group consisting of 1,3-oxazolyl, isoxazolyl (1,2-oxazolyl), thiazolyl (1,3-thiazolyl, preferably 1,3-thiazol-2-yl), isothiazolyl (1,2-thiazolyl), 1,2,3-thiadiazolyl, 1,2,4-thiadiazolyl, 1,2,5-thiadiazolyl, 1,3,4- thiadiazolyl, pyridazinyl (1,2-diazinyl), pyrimidinyl (1,3-diazinyl), and pyrazinyl (1,4-diazinyl)).

In another preferred embodiment, $R^2$ is an optionally substituted 5- or 6-membered aromatic heterocycle selected from the group consisting of pyrazinyl, isothiazolyl (1,2-thiazolyl), 1,3-oxazolyl, 1,2,3-thiadiazolyl (e.g. 4-methyl-1,2,3-thiadiazolyl), 1,3-thiazolyl (e.g. 4-methyl-1,3-thiazolyl, preferably 1,3-thiazol-2-yl, e.g. 4-methyl-1,3-thiazol-2-yl), and 1,2-oxazolyl (e.g. 3-methyl-1,2-oxazolyl); and preferably optionally substituted 5- or 6-membered aromatic heterocycle selected from the group consisting of pyrazin-2-yl, 1,2-thiazol-3-yl, 1,3-oxazol-5-yl, 1,3-oxazol-2-yl, 1,2,3-thiadiazol-5-yl (e.g. 4-methyl-1,2,3-thiadiazol-5-yl), 1,3-thiazolyl (e.g. 4-methyl-1,3-thiazolyl, preferably 1,3-thiazol-2-yl, e.g. 4-methyl-1,3-thiazol-2-yl), and 1,2-oxazolyl (e.g. 3-methyl-1,2-oxazolyl); and even more preferably $R^2$ is an optionally substituted 5- or 6-membered aromatic heterocycle selected from the group consisting of pyrazinyl, isothiazolyl (1,2-thiazolyl), 1,3-oxazolyl, and 1,2,3-thiadiazolyl (e.g. 4-methyl-1,2,3-thiadiazolyl). Most preferably $R^2$ is an optionally substituted 5- or 6-membered aromatic heterocycle selected from the group consisting of pyrazin-2-yl, 1,2-thiazol-3-yl, 1,3-oxazol-5-yl, 1,3-oxazol-2-yl, 4-methyl-1,2,3-thiadiazol-5-yl (e.g. 4-methyl-1,2,3-thiadiazolyl).

In another preferred embodiment, $R^2$ is an optionally substituted 5- or 6-membered aromatic heterocycle selected from the group consisting of pyrazinyl (e.g. pyrazin-2-yl), isothiazolyl (1,2-thiazolyl, e.g. 1,2-thiazol-3-yl) and 1,3-oxazolyl (e.g. 1,3-oxazol-5-yl).

In a further preferred embodiment, $R^2$ is an optionally substituted 5- or 6-membered aromatic heterocycle selected from the group consisting of pyrazinyl (e.g. pyrazin-2-yl), isothiazolyl (1,2-thiazolyl, e.g. 1,2-thiazol-3-yl), 1,3-oxazolyl (e.g. 1,3-oxazol-2-yl or 1,3-oxazol-5-yl), and thiazolyl (1,3-thiazol-2-yl, e.g. thiazol-2-yl).

In another preferred embodiment, $R^2$ is an unsubstituted 5- or 6-membered aromatic heterocycle. For example, an unsubstituted 5- or 6-membered aromatic heterocycle as described in the embodiments and preferred embodiments mentioned above. For example, $R^2$ is selected from the group consisting of unsubstituted 1,3-oxazolyl, unsubstituted isoxazolyl (1,2-oxazolyl), unsubstituted thiazolyl (1,3-thiazolyl, preferably 1,3-thiazol-2-yl), unsubstituted isothiazolyl (1,2-thiazolyl), and unsubstituted pyrazinyl (1,4-diazinyl); or selected from the group consisting of unsubstituted 1,3-oxazolyl, unsubstituted isoxazolyl (1,2-oxazolyl), unsubstituted isothiazolyl (1,2-thiazolyl), and unsubstituted pyrazinyl (1,4-diazinyl); or selected from the group consisting of unsubstituted isothiazolyl (1,2-thiazolyl) and unsubstituted pyrazinyl (1,4-diazinyl) (preferably unsubstituted isothiazol-3-yl (1,2-thiazol-3-yl) and unsubstituted pyrazin-2-yl (1,4-diazin-2-yl)).

In another preferred embodiment, $R^2$ is selected from the group consisting of unsubstituted pyrazinyl, unsubstituted isothiazolyl (1,2-thiazolyl), unsubstituted 1,3-oxazolyl, 1,2,3-thiadiazolyl optionally substituted with one $C_{1-4}$alkyl group (e.g. 4-methyl-1,2,3-thiadiazolyl), 1,3-thiazolyl optionally substituted with one $C_{1-4}$alkyl group (e.g. 4-methyl-1,3-thiazolyl, preferably 1,3-thiazol-2-yl optionally substituted with one $C_{1-4}$alkyl group, e.g. 4-methyl-1,3-thiazol-2-yl), and 1,2-oxazolyl optionally substituted with one $C_{1-4}$alkyl group (e.g. 3-methyl-1,2-oxazolyl); preferably optionally substituted 5- or 6-membered aromatic heterocycle selected from the group consisting of unsubstituted pyrazin-2-yl, unsubstituted 1,2-thiazol-3-yl, unsubstituted 1,3-oxazol-5-yl, unsubstituted 1,3-oxazol-2-yl, 1,2,3-thiadiazolyl substituted with one $C_{1-4}$alkyl group (e.g. 4-methyl-1,2,3-thiadiazolyl), 1,3-thiazolyl substituted with one $C_{1-4}$alkyl group (e.g. 4-methyl-1,3-thiazolyl, preferably 1,3-thiazol-2-yl substituted with one $C_{1-4}$alkyl group, e.g. 4-methyl-1,3-thiazol-2-yl), and 1,2-oxazolyl substituted with one $C_{1-4}$alkyl group (e.g. 3-methyl-1,2-oxazolyl); and more preferably $R^2$ is selected from the group consisting of unsubstituted pyrazinyl, unsubstituted isothiazolyl (1,2-thiazolyl), unsubstituted 1,3-oxazolyl, and 1,2,3-thiadiazolyl substituted with one $C_{1-4}$ alkyl group (e.g. 4-methyl-1,2,3-thiadiazolyl). Most preferably $R^2$ is 5- or 6-membered aromatic heterocycle selected from the group consisting of unsubstituted pyrazin-2-yl, unsubstituted 1,2-thiazol-3-yl, unsubstituted 1,3-oxazol-5-yl, unsubstituted 1,3-oxazol-2-yl, and 1,2,3-thiadiazol-5-yl substituted with one $C_{1-4}$alkyl group (e.g. 4-methyl-1,2,3-thiadiazolyl).

In the embodiments described above wherein $R^2$ is an optionally substituted 5- or 6-membered aromatic heterocycle, said 5- or 6-membered aromatic heterocycle is preferably optionally substituted with 1 or 2 substituents, each substituent being independently selected from the group consisting of $C_{1-3}$alkyl (e.g. methyl, ethyl, propyl or isopropyl) and $C_{1-3}$alkyl substituted with 1, 2 or 3 halogens, and preferably each substituent being $C_{1-3}$alkyl, for example methyl. More preferably, it is optionally substituted with 1 or 2 substituents independently selected from the group consisting of $C_{1-3}$alkyl (e.g. methyl, ethyl, propyl or isopropyl) and $C_{1-3}$alkyl substituted with 1, 2 or 3 fluorines (for example $CF_3$), and more preferably each substituent being $C_{1-3}$alkyl, for example methyl.

In another preferred embodiment, when $R^2$ is an optionally substituted 5- or 6-membered aromatic heterocycle, said 5- or 6-membered aromatic heterocycle is preferably optionally substituted with 1 substituent selected from the group consisting of $C_{1-3}$alkyl (e.g. methyl, ethyl, propyl or isopropyl) and $C_{1-3}$alkyl substituted with 1, 2 or 3 halogens; and preferably optionally substituted with 1 substituent that is $C_{1-3}$alkyl, for example methyl. For example, it may be preferably optionally substituted with 1 substituent that is selected from the group consisting of $C_{1-3}$alkyl and $C_{1-3}$alkyl substituted with 1, 2 or 3 fluorines (for example $CF_3$); preferably optionally substituted with 1 substituent that is selected from the group consisting of methyl and $CF_3$; and more preferably optionally substituted with 1 substituent that is methyl.

In certain especially preferred embodiments, $R^2$ is selected from the group consisting of:

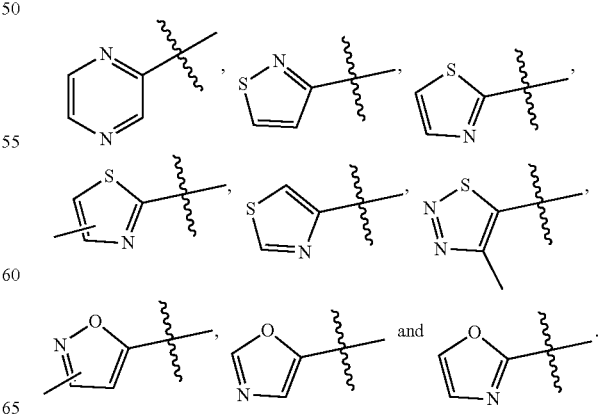

In certain especially preferred embodiments, R² is selected from the group consisting of:

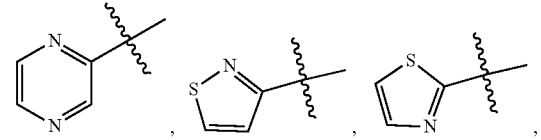

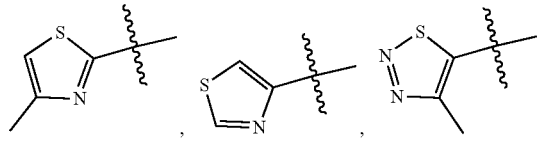

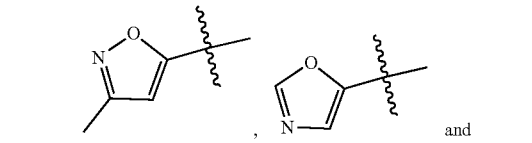

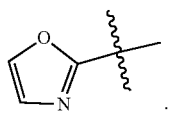

In another embodiment, R² is selected from the group consisting of:

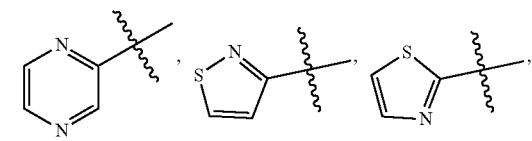

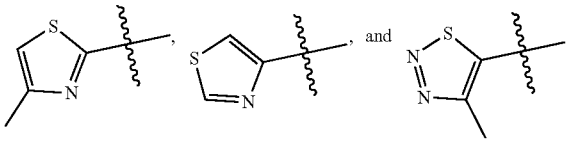

More preferably, R² is selected from the group consisting of:

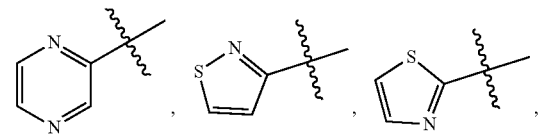

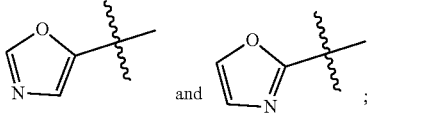

or selected from the group consisting of:

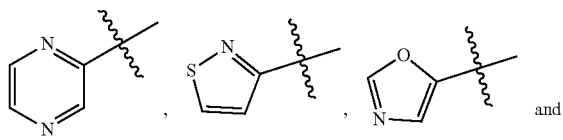

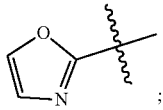

or selected from the group consisting of:

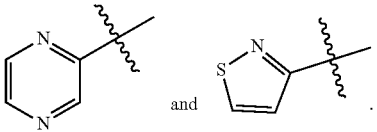 [SMILES: *c1cnccn1 ; *c1ccsn1]

In another preferred embodiment, R² is selected from the group consisting of:

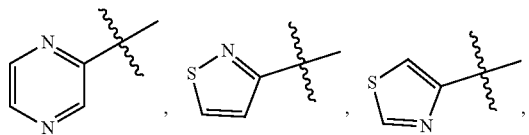

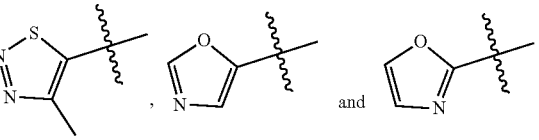

or selected from the group consisting of:

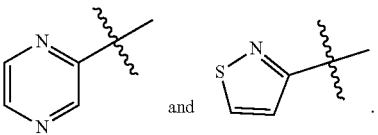 [SMILES: *c1cnccn1 ; *c1ccsn1]

In another especially preferred embodiments, R² is selected from the group consisting of:

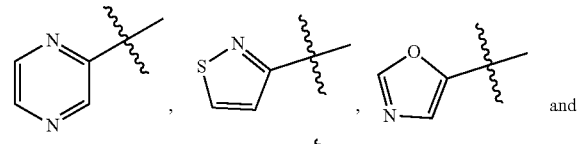

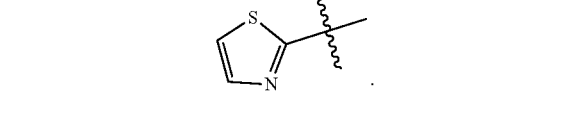

In another especially preferred embodiments, R² is selected from the group consisting of:

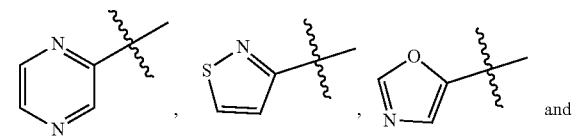

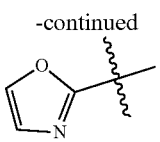

In a further especially preferred embodiments, $R^2$ selected from the group consisting of:

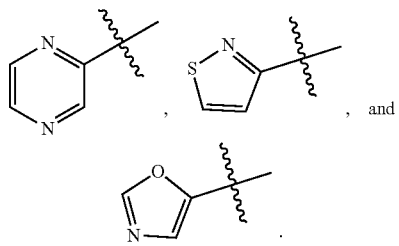

In an especially preferred embodiment $R^1$ is an optionally substituted phenyl, or an optionally substituted 5- or 6-membered aromatic heterocycle selected from the group consisting of pyridinyl (for example pyridin-2-yl, pyridin-3-yl or pyridin-4-yl), pyrimidinyl, pyrazinyl, thiazolyl (for example 1,3-thiazol-2-yl, 1,3-thiazol-4-yl, or 1,3-thiazol-5-yl) and isothiazolyl (1,2-thiazolyl, for example 1,2-thiazol-3-yl); and $R^2$ is an optionally substituted 5- or 6-membered aromatic heterocycle comprising 2 heteroatoms independently selected from the group consisting of N, S and O, wherein at least one of the heteroatoms is N. In such embodiments, preferably $R^1$ is an optionally substituted phenyl.

In another especially preferred embodiment $R^1$ is an optionally substituted phenyl, wherein said phenyl is optionally substituted with 1, 2 or 3 substituents, each substituent being independently selected from the group consisting of halogen (preferably F or Cl), $C_{1-8}$alkyl, $C_{1-8}$alkyl substituted with 1, 2 or 3 halogens (preferably F) or OH groups (preferably 1 OH group, e.g CH$_2$OH), OC$_{1-8}$alkyl, and OC$_{1-8}$alkyl substituted with 1, 2 or 3 halogens (preferably F) (more preferably, each substituent is independently selected from the group consisting of $C_{1-4}$alkyl (e.g. methyl), $C_{1-4}$alkyl substituted with 1, 2 or 3 halogens (preferably F, e.g. CF$_3$) or OH groups (preferably 1 OH group, e.g CH$_2$H), OC$_{1-4}$alkyl (e.g. methoxy), and OC$_{1-4}$alkyl substituted with 1, 2 or 3 halogens (preferably F, e.g. OCF$_3$); and $R^2$ is an optionally substituted 5- or 6-membered aromatic heterocycle selected from the group consisting of imidazolyl (1,3-diazolyl), pyrazolyl (1,2-diazolyl), 1,3-oxazolyl, isoxazolyl (1,2-oxazolyl), thiazolyl (1,3-thiazolyl, preferably 1,3-thiazol-2-yl), isothiazolyl (1,2-thiazolyl), 1H-1,2,3-triazolyl, 2H-1,2,3-triazolyl, 1H-1,2,4-triazolyl, 4H-1,2,4-triazolyl, furazanyl (1,2,5-oxadiazolyl), 1,2,3-oxadiazolyl, 1,2,4-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), pyrazinyl (1,4-diazinyl), 1,2,3-triazinyl, 1,2,4-triazinyl, and 1,3,5-triazinyl (for example selected from the group consisting of 1,3-oxazolyl, isoxazolyl (1,2-oxazolyl), thiazolyl (1,3-thiazolyl, preferably 1,3-thiazol-2-yl), isothiazolyl (1,2-thiazolyl), 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), and pyrazinyl (1,4-diazinyl)).

In another especially preferred embodiment $R^1$ is an optionally substituted phenyl, wherein said phenyl is optionally substituted with 1, 2 or 3 substituents, each substituent being independently selected from the group consisting of F, meta-Cl, para-Cl, C-alkyl, C-alkyl substituted with 1, 2 or 3 halogens (preferably F) or OH groups (preferably 1 OH group, e.g CH$_2$OH), OC$_{1-8}$alkyl, and OC$_{1-8}$alkyl substituted with 1, 2 or 3 halogens (preferably F) (more preferably, each substituent is independently selected from the group consisting of $C_{1-4}$alkyl (e.g. methyl), $C_{1-4}$alkyl substituted with 1, 2 or 3 halogens (preferably F, e.g. CF$_3$) or OH groups (preferably 1 OH group, e.g CH$_2$OH), OC$_{1-4}$alkyl (e.g. methoxy), and OC$_{1-4}$alkyl substituted with 1, 2 or 3 halogens (preferably F, e.g. OCF$_3$); or F, meta-Cl, para-Cl, $C_{1-8}$alkyl, $C_{1-8}$alkyl substituted with 1, 2 or 3 halogens (preferably F) or OH groups (preferably 1 OH group, e.g CH$_2$OH), OC$_{1-4}$alkyl, and OC$_{1-4}$alkyl substituted with 1, 2 or 3 halogens (preferably F); or each substituent is independently selected from the group consisting of $C_{1-4}$alkyl (e.g. methyl), $C_{1-4}$alkyl substituted with 1, 2 or 3 halogens (preferably F, e.g. CF$_3$) or OH groups (preferably 1 OH group, e.g CH$_2$OH), OC$_{1-4}$alkyl (e.g. methoxy), and OC$_{1-4}$alkyl substituted with 1, 2 or 3 halogens (preferably F, e.g. OCF$_3$)); and $R^2$ is an optionally substituted 5- or 6-membered aromatic heterocycle selected from the group consisting of imidazolyl (1,3-diazolyl), pyrazolyl (1,2-diazolyl), 1,3-oxazolyl, isoxazolyl (1,2-oxazolyl), thiazolyl (1,3-thiazolyl, preferably 1,3-thiazol-2-yl), isothiazolyl (1,2-thiazolyl), 1H-1,2,3-triazolyl, 2H-1,2,3-triazolyl, 1H-1,2,4-triazolyl, 4H-1,2,4-triazolyl, furazanyl (1,2,5-oxadiazolyl), 1,2,3-oxadiazolyl, 1,2,4-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), pyrazinyl (1,4-diazinyl), 1,2,3-triazinyl, 1,2,4-triazinyl, and 1,3,5-triazinyl (for example selected from the group consisting of 1,3-oxazolyl, isoxazolyl (1,2-oxazolyl), thiazolyl (1,3-thiazolyl, preferably 1,3-thiazol-2-yl), isothiazolyl (1,2-thiazolyl), 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), and pyrazinyl (1,4-diazinyl)).

In another especially preferred embodiment $R^1$ is an optionally substituted phenyl, wherein said phenyl is optionally substituted with 1, 2 or 3 substituents, each substituent being independently selected from the group consisting of halogen (preferably F or Cl), $C_{1-8}$alkyl, $C_{1-8}$alkyl substituted with 1, 2 or 3 halogens (preferably F) or OH groups (preferably 1 OH group, e.g CH$_2$OH), OC$_{1-4}$alkyl, and OC$_{1-4}$alkyl substituted with 1, 2 or 3 halogens (preferably F) (more preferably, each substituent is independently selected from the group consisting of $C_{1-4}$alkyl (e.g. methyl), $C_{1-4}$alkyl substituted with 1, 2 or 3 halogens (preferably F, e.g. CF$_3$) or OH groups (preferably 1 OH group, e.g CH$_2$OH), OC$_{1-4}$alkyl (e.g. methoxy), and OC$_{1-4}$alkyl substituted with 1, 2 or 3 halogens (preferably F, e.g. OCF$_3$); and $R^2$ is an optionally substituted 5- or 6-membered aromatic heterocycle selected from the group consisting of imidazolyl (1,3-diazolyl), pyrazolyl (1,2-diazolyl), 1,3-oxazolyl, isoxazolyl (1,2-oxazolyl), thiazol-2-yl (1,3-thiazol-2-yl), isothiazolyl (1,2-thiazolyl), 1H-1,2,3-triazolyl, 2H-1,2,3-triazolyl, 1H-1,2,4-triazolyl, 4H-1,2,4-triazolyl, furazanyl (1,2,5-oxadiazolyl), 1,2,3-oxadiazolyl, 1,2,4-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), pyrazinyl (1,4-diazinyl), 1,2,3-triazinyl, 1,2,4-triazinyl, and 1,3,5-triazinyl (for example selected from the group consisting of 1,3-oxazolyl, isoxazolyl (1,2-oxazolyl), thiazol-2-yl (1,3-thiazol-2-yl), isothiazolyl (1,2-thiazolyl), 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), and pyrazinyl (1,4-diazinyl)).

In another especially preferred embodiment $R^1$ is an optionally substituted phenyl, wherein said phenyl is optionally substituted with 1, 2 or 3 substituents, each substituent being independently selected from the group consisting of halogen (preferably F or Cl), $C_{1-8}$alkyl, $C_{1-4}$alkyl substituted with 1, 2 or 3 halogens (preferably F), $OC_{1-8}$-alkyl, and $OC_{1-8}$-alkyl substituted with 1, 2 or 3 halogens (preferably F) (more preferably, each substituent is independently selected from the group consisting of $C_{1-4}$alkyl (e.g. methyl), $C_{1-4}$alkyl substituted with 1, 2 or 3 halogens (preferably F, e.g. $CF_3$), $OC_{1-4}$alkyl (e.g. methoxy), and $OC_{1-4}$alkyl substituted with 1, 2 or 3 halogens (preferably F, e.g. $OCF_3$); and $R^2$ is an optionally substituted 5- or 6-membered aromatic heterocycle selected from the group consisting of imidazolyl (1,3-diazolyl), pyrazolyl (1,2-diazolyl), 1,3-oxazolyl, isoxazolyl (1,2-oxazolyl), thiazolyl (1,3-thiazolyl, preferably 1,3-thiazol-2-yl), isothiazolyl (1,2-thiazolyl), 1H-1,2,3-triazolyl, 2H-1,2,3-triazolyl, 1H-1,2,4-triazolyl, 4H-1,2,4-triazolyl, furazanyl(1,2,5-oxadiazolyl), 1,2,3-oxadiazolyl, 1,2,4-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), pyrazinyl (1,4-diazinyl), 1,2,3-triazinyl, 1,2,4-triazinyl, and 1,3,5-triazinyl (for example selected from the group consisting of 1,3-oxazolyl, isoxazolyl (1,2-oxazolyl), thiazolyl (1,3-thiazolyl, preferably 1,3-thiazol-2-yl), isothiazolyl (1,2-thiazolyl), 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), and pyrazinyl (1,4-diazinyl)).

In another especially preferred embodiment, $R^1$ is a substituted phenyl, and said phenyl is substituted with 1 or 2 substituents, each substituent being independently selected from the group consisting of halogen (e.g. F or Cl), $C_{1-4}$alkyl (e.g. methyl), $C_{1-4}$alkyl substituted with 1, 2 or 3 halogens (preferably F, e.g. $CF_3$) or OH groups (preferably 1 OH group, e.g. $CH_2OH$), and $OC_{1-4}$alkyl (e.g. methoxy) (and even more preferably each substituent is independently selected from the group consisting of halogen (e.g. F or Cl), $C_{1-4}$alkyl, $C_{1-4}$alkyl substituted with 1, 2, or 3 OH groups (preferably 1 OH group), and $OC_{1-4}$alkyl (for example F, methyl, $CH_2OH$ or methoxy; or C, methyl, $CH_2OH$ or methoxy); or each substituent is independently selected from the group consisting of F, $C_{1-4}$alkyl, $C_{1-4}$alkyl substituted with 1, 2, or 3 OH groups (preferably 1 OH group), and $OC_{1-4}$alkyl (for example F, methyl, $CH_2OH$ or methoxy); and $R^2$ is an optionally substituted 5- or 6-membered aromatic heterocycle selected from the group consisting of pyrazinyl, 1,2-thiazolyl, 1,3-oxazolyl, 1,2,3-thiadiazolyl (e.g. 4-methyl-1,2,3-thiadiazolyl), 1,3-thiazolyl (e.g. 4-methyl-1,3-thiazolyl, preferably 1,3-thiazol-2-yl, e.g. 4-methyl-1,3-thiazol-2-yl), and 1,2-oxazolyl (e.g. 3-methyl-1,2-oxazolyl) (preferably selected from the group consisting of pyrazin-2-yl, 1,2-thiazol-3-yl, 1,3-oxazol-5-yl, 1,3-oxazol-2-yl, 1,2,3-thiadiazol-5-yl, 1,3-thiazol-2-yl, and 1,2-oxazol-5-yl), even more preferably selected from the group consisting of unsubstituted pyrazinyl, unsubstituted 1,2-thiazolyl, unsubstituted 1,3-oxazolyl, and 1,2,3-thiadiazolyl substituted with one $C_{1-4}$alkyl group (e.g. 4-methyl-1,2,3-thiadiazolyl), and most preferably selected from the group consisting of unsubstituted pyrazin-2-yl, unsubstituted 1,2-thiazol-3-yl, unsubstituted 1,3-oxazol-5-yl, unsubstituted 1,3-oxazol-2-yl, and 1,2,3-thiadiazol-5-yl substituted with one $C_{1-4}$alkyl group (e.g. 4-methyl-1,2,3-thiadiazol-5-yl)).

In another especially preferred embodiment, $R^1$ is a substituted phenyl, and said phenyl is substituted with 1 or 2 substituents, each substituent being independently selected from the group consisting of halogen (e.g. F or Cl), $C_{1-4}$alkyl (e.g. methyl), $C_{1-4}$alkyl substituted with 1, 2 or 3 halogens (preferably F, e.g. $CF_3$), and $OC_{1-4}$-alkyl (e.g. methoxy) (and even more preferably each substituent is independently selected from the group consisting of halogen (e.g. F or Cl), $C_{1-4}$alkyl, and $OC_{1-4}$alkyl (for example F, methyl or methoxy; or Cl, methyl or methoxy); or each substituent is independently selected from the group consisting of F, $C_{1-4}$ alkyl, and $OC_{1-4}$alkyl (for example F, methyl or methoxy); and $R^2$ is an optionally substituted 5- or 6-membered aromatic heterocycle selected from the group consisting of pyrazinyl, 1,2-thiazolyl, 1,3-oxazolyl, 1,2,3-thiadiazolyl (e.g. 4-methyl-1,2,3-thiadiazolyl), 1,3-thiazolyl (e.g. 4-methyl-1,3-thiazolyl, preferably 1,3-thiazol-2-yl, e.g. 4-methyl-1,3-thiazol-2-yl), and 1,2-oxazolyl (e.g. 3-methyl-1,2-oxazolyl) (preferably selected from the group consisting of pyrazin-2-yl, 1,2-thiazol-3-yl, 1,3-oxazol-5-yl, 1,3-oxazol-2-yl, 1,2,3-thiadiazol-5-yl, 1,3-thiazol-2-yl, and 1,2-oxazol-5-yl), even more preferably selected from the group consisting of unsubstituted pyrazinyl, unsubstituted 1,2-thiazolyl, unsubstituted 1,3-oxazolyl, and 1,2,3-thiadiazolyl substituted with one $C_{1-4}$alkyl group (e.g. 4-methyl-1,2,3-thiadiazolyl), and most preferably selected from the group consisting of unsubstituted pyrazin-2-yl, unsubstituted 1,2-thiazol-3-yl, unsubstituted 1,3-oxazol-5-yl, unsubstituted 1,3-oxazol-2-yl, and 1,2,3-thiadiazol-5-yl substituted with one $C_{1-4}$alkyl group (e.g. 4-methyl-1,2,3-thiadiazol-5-yl)).

In the especially preferred embodiments mentioned above, preferably $R^2$ is substituted with 1 substituent selected from the group consisting of halogen, $C_{1-8}$alkyl, and $C_{1-8}$alkyl substituted with 1, 2 or 3 halogens or OH groups; and more preferably selected from the group consisting of halogen, $C_{1-4}$alkyl, and $C_{1-4}$alkyl substituted with 1, 2 or 3 halogens or OH groups; and even more preferably selected from the group consisting of F, C, $C_{1-4}$alkyl (e.g. methyl, ethyl, propyl or isopropyl) and $C_{1-4}$alkyl substituted with 1, 2 or 3 F (e.g. $CF_3$) or 1 OH group (e.g. $CH_2OH$). For example, $R^2$ is substituted with 1 substituent selected from the group consisting of F, Cl, $C_{1-4}$alkyl (e.g. methyl, ethyl, propyl or isopropyl) and $C_{1-4}$alkyl substituted with 1 OH (e.g. $CH_2OH$), and more preferably the substituent is $C_{1-4}$alkyl (e.g. methyl, ethyl, propyl or isopropyl; and preferably methyl) or $C_{1-4}$alkyl substituted with 1 OH (e.g. $CH_2OH$).

In the especially preferred embodiments mentioned above, preferably $R^2$ is substituted with 1 substituent selected from the group consisting of halogen, $C_{1-8}$alkyl, and $C_{1-8}$alkyl substituted with 1, 2 or 3 halogens; and more preferably selected from the group consisting of halogen, $C_{1-4}$alkyl, and $C_{1-4}$alkyl substituted with 1, 2 or 3 halogens; and even more preferably selected from the group consisting of F, C, $C_{1-4}$alkyl (e.g. methyl, ethyl, propyl or isopropyl) and $C_{1-4}$alkyl substituted with 1, 2 or 3 F (e.g. $CF_3$). For example, $R^2$ is substituted with 1 substituent selected from the group consisting of F, C and $C_{1-4}$alkyl (e.g. methyl, ethyl, propyl or isopropyl), and more preferably the substituent is $C_{1-4}$alkyl (e.g. methyl, ethyl, propyl or isopropyl; and preferably methyl).

In another very especially preferred embodiment, $R^1$ is a substituted phenyl, and said phenyl is substituted with 1 or 2 substituents, each substituent being independently selected from the group consisting of halogen (e.g. F or Cl), $C_{1-4}$alkyl (e.g. methyl), $C_{1-4}$alkyl substituted with 1, 2 or 3 halogens (preferably F, e.g. $CF_3$) or OH groups (preferably 1 OH group, e.g. $CH_2OH$), and $OC_{1-4}$alkyl (e.g. methoxy) (preferably substituted with 1 or 2 substituents, each substituent being independently selected from the group consisting of $C_{1-4}$alkyl (e.g. methyl), $C_{1-4}$alkyl substituted with 1, 2 or 3 halogens (preferably F, e.g. $CF_3$) or OH groups (preferably 1 OH group, e.g. $CH_2OH$), and $OC_{1-4}$-alkyl (e.g. methoxy)); and $R^2$ is a 5- or 6-membered aromatic heterocycle selected from the group consisting of unsubstituted pyrazin-2-yl, unsubstituted 1,2-thiazol-3-yl, unsubstituted 1,3-oxazol-5-yl, unsubstituted 1,3-oxazol-2-yl, and 4-methyl-1,2,3-thiadiazol-5-yl (and preferably unsubstituted pyrazin-2-yl, and unsubstituted 1,2-thiazol-3-yl).

In another very especially preferred embodiment, $R^1$ is a substituted phenyl, and said phenyl is substituted with 1 or 2 substituents, each substituent being independently selected from the group consisting of halogen (e.g. F or Cl), $C_{1-4}$alkyl (e.g. methyl), $C_{1-4}$alkyl substituted with 1, 2 or 3 halogens (preferably F, e.g. $CF_3$), and $OC_{1-4}$alkyl (e.g. methoxy) (preferably substituted with 1 or 2 substituents, each substituent being independently selected from the group consisting of $C_{1-4}$alkyl (e.g. methyl), $C_{1-4}$alkyl substituted with 1, 2 or 3 halogens (preferably F, e.g. $CF_3$), and $OC_{1-4}$-alkyl (e.g. methoxy)); and $R^2$ is a 5- or 6-membered aromatic heterocycle selected from the group consisting of unsubstituted pyrazin-2-yl, unsubstituted 1,2-thiazol-3-yl, unsubstituted 1,3-oxazol-5-yl, unsubstituted 1,3-oxazol-2-yl, and 4-methyl-1,2,3-thiadiazol-5-yl (and preferably unsubstituted pyrazin-2-yl, and unsubstituted 1,2-thiazol-3-yl).

In all embodiments of the invention described herein, preferably the compound of the invention is a compound of formula (I), with the proviso that the compounds is not selected from the group consisting of

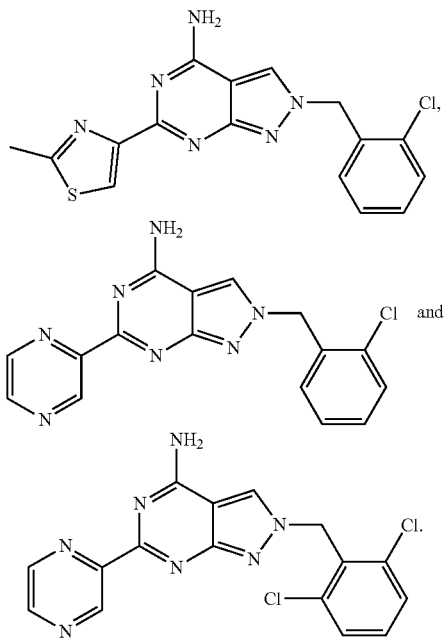

In certain preferred embodiments, the compound of formula (I) is a compound of formula (I) described in the Examples section below, or a pharmaceutically acceptable ester, amide, carbamate, solvate or salt thereof, including a salt of such an ester, amide or carbamate. In particular, the compound of formula (I) may be a compound selected from the group consisting of:

Example 1

2-[(3-methylphenyl)methyl]-6-(1,2-thiazol-3-yl)-2H-pyrazolo[3,4-d]pyrimidin-4-amine;

Example 2

2-[(3-methoxyphenyl)methyl]-6-(pyrazin-2-yl)-2H-pyrazolo[3,4-d]pyrimidin-4-amine;

Example 3

3-{[4-amino-6-(pyrazin-2-yl)-2H-pyrazolo[3,4-d]pyrimidin-2-yl]methyl}phenol;

Example 4

2-[(3-methoxyphenyl)methyl]-6-(1,3-oxazol-2-yl)-2H-pyrazolo[3,4-d]pyrimidin-4-amine;

Example 5

2-[(3-methoxyphenyl)methyl]-6-(4-methyl-1,3-thiazol-2-yl)-2H-pyrazolo[3,4-d]pyrimidin-4-amine;

Example 6

2-[(3-methoxyphenyl)methyl]-6-(3-methyl-1,2-oxazol-5-yl)-2H-pyrazolo[3,4-d]pyrimidin-4-amine;

Example 7

2-[(3-methoxyphenyl)methyl]-6-(4-methyl-1,2,3-thiadiazol-5-yl)-2H-pyrazolo[3,4-d]pyrimidin-4-amine;

Example 8

2-[(3-methoxyphenyl)methyl]-6-(1,3-thiazol-2-yl)-2H-pyrazolo[3,4-d]pyrimidin-4-amine;

Example 9

2-[(3-methoxyphenyl)methyl]-6-(1,3-thiazol-4-yl)-2H-pyrazolo[3,4-d]pyrimidin-4-amine;

Example 10

2-[(3-methoxyphenyl)methyl]-6-(1,2-thiazol-3-yl)-2H-pyrazolo[3,4-d]pyrimidin-4-amine;

Example 11

2-[(3-methoxyphenyl)methyl]-6-(1,3-oxazol-5-yl)-2H-pyrazolo[3,4-d]pyrimidin-4-amine;

Example 12

2-[(4-methylphenyl)methyl]-6-(pyrazin-2-yl)-2H-pyrazolo[3,4-d]pyrimidin-4-amine;

Example 13

2-[(4-methylphenyl)methyl]-6-(1,2-thiazol-3-yl)-2H-pyrazolo[3,4-d]pyrimidin-4-amine;

Example 14

2-[(4-methylphenyl)methyl]-6-(1,3-thiazol-2-yl)-2H-pyrazolo[3,4-d]pyrimidin-4-amine;

Example 15

2-[(4-methoxyphenyl)methyl]-6-(pyrazin-2-yl)-2H-pyrazolo[3,4-d]pyrimidin-4-amine;

Example 16

6-(1,2-thiazol-3-yl)-2-{[3-(trifluoromethoxy)phenyl]methyl}-2H-pyrazolo[3,4-d]pyrimidin-4-amine;

Example 17

6-(1,2-thiazol-3-yl)-2-{[4-(trifluoromethyl)phenyl]methyl}-2H-pyrazolo[3,4-d]pyrimidin-4-amine;

Example 18

2-[(3-methoxy-4-methylphenyl)methyl]-6-(1,2-thiazol-3-yl)-2H-pyrazolo[3,4-d]pyrimidin-4-amine;

Example 19

2-[(3-fluoro-4-methylphenyl)methyl]-6-(1,2-thiazol-3-yl)-2H-pyrazolo[3,4-d]pyrimidin-4-amine;

Example 20

2-[(2,5-dichlorophenyl)methyl]-6-(1,2-thiazol-3-yl)-2H-pyrazolo[3,4-d]pyrimidin-4-amine;

Example 21

2-[(3,4-dimethylphenyl)methyl]-6-(1,2-thiazol-3-yl)-2H-pyrazolo[3,4-d]pyrimidin-4-amine;

Example 22

2-[(pyridin-2-yl)methyl]-6-(1,2-thiazol-3-yl)-2H-pyrazolo[3,4-d]pyrimidin-4-amine;

Example 23

2-[(6-methylpyridin-3-yl)methyl]-6-(1,2-thiazol-3-yl)-2H-pyrazolo[3,4-d]pyrimidin-4-amine;

Example 24

2-{[4-methyl-3-(trifluoromethyl)phenyl]methyl}-6-(1,2-thiazol-3-yl)-2H-pyrazolo[3,4-d]pyrimidin-4-amine;

Example 25

2-[(2-methoxy-4-methylphenyl)methyl]-6-(1,2-thiazol-3-yl)-2H-pyrazolo[3,4-d]pyrimidin-4-amine;

Example 26

2-[(3-methylphenyl)methyl]-6-(1,3-oxazol-2-yl)-2H-pyrazolo[3,4-d]pyrimidin-4-amine;

Example 27

2-[(3-methylphenyl)methyl]-6-(pyrazin-2-yl)-2H-pyrazolo[3,4-d]pyrimidin-4-amine;

Example 28

6-(pyrazin-2-yl)-2-{[3-(trifluoromethyl)phenyl]methyl}-2H-pyrazolo[3,4-d]pyrimidin-4-amine;

Example 29

2-[(3-fluorophenyl)methyl]-6-(1,2-thiazol-3-yl)-2H-pyrazolo[3,4-d]pyrimidin-4-amine;

Example 30

2-[(3-fluorophenyl)methyl]-6-(pyrazin-2-yl)-2H-pyrazolo[3,4-d]pyrimidin-4-amine;

Example 31

2-[(2-methylphenyl)methyl]-6-(pyrazin-2-yl)-2H-pyrazolo[3,4-d]pyrimidin-4-amine;

Example 32

2-[(2-methylphenyl)methyl]-6-(1,2-thiazol-3-yl)-2H-pyrazolo[3,4-d]pyrimidin-4-amine;

Example 33

6-(1,3-thiazol-2-yl)-2-[(1,3-thiazol-2-yl)methyl]-2H-pyrazolo[3,4-d]pyrimidin-4-amine;

Example 34

2-[(1,3-thiazol-2-yl)methyl]-6-(1,2-thiazol-3-yl)-2H-pyrazolo[3,4-d]pyrimidin-4-amine;

Example 35

2-[(3-chlorophenyl)methyl]-6-(1,2-thiazol-3-yl)-2H-pyrazolo[3,4-d]pyrimidin-4-amine;

Example 36

2-[(3-chlorophenyl)methyl]-6-(pyrazin-2-yl)-2H-pyrazolo[3,4-d]pyrimidin-4-amine;

Example 37

2-[(2-methoxyphenyl)methyl]-6-(pyrazin-2-yl)-2H-pyrazolo[3,4-d]pyrimidin-4-amine;

Example 38

2-[(2-methoxyphenyl)methyl]-6-(1,2-thiazol-3-yl)-2H-pyrazolo[3,4-d]pyrimidin-4-amine;

Example 39

2-[(2-methoxyphenyl)methyl]-6-(1,3-oxazol-2-yl)-2H-pyrazolo[3,4-d]pyrimidin-4-amine;

Example 40

2-[(2-methoxyphenyl)methyl]-6-(1,3-oxazol-5-yl)-2H-pyrazolo[3,4-d]pyrimidin-4-amine;

Example 41

2-[(3,4-dimethoxyphenyl)methyl]-6-(pyrazin-2-yl)-2H-pyrazolo[3,4-d]pyrimidin-4-amine;

Example 42

3-{[4-amino-6-(1,2-thiazol-3-yl)-2H-pyrazolo[3,4-d]pyrimidin-2-yl]methyl}phenol;

Example 43

2-{[4-amino-6-(1,2-thiazol-3-yl)-2H-pyrazolo[3,4-d]pyrimidin-2-yl]methyl}-5-methylphenol;

Example 44

2-{[4-amino-6-(1,2-thiazol-3-yl)-2H-pyrazolo[3,4-d]pyrimidin-2-yl]methyl}phenol;

Example 45

5-{[4-amino-6-(1,2-thiazol-3-yl)-2H-pyrazolo[3,4-d]pyrimidin-2-yl]methyl}-2-methylphenol; and

Example 46

[3-[(4-amino-6-(1,2-thiazol-3-yl)-pyrazolo[3,4-d]pyrimidin-2-yl)methyl]phenyl]methanol;
or a pharmaceutically acceptable ester, amide, carbamate, solvate or salt thereof, including a salt of such an ester, amide or carbamate.

Depending upon the substituents present in the compounds of formula (I), the compounds may exist as stereoisomers and/or geometric isomers. All individual stereoisomers and geometric isomers, as well as mixtures thereof, are included within the scope of the invention. Isotopic forms, for example where a hydrogen atom is replaced with deuterium, are also included within the invention. Certain isotopic forms may have beneficial biological properties, for example improved metabolic stability or enhanced therapeutic activity over other isotopic forms; or a specific isotopic form may be useful for biological imaging purposes, for example carbon-11, nitrogen-13, oxygen-15 or fluorine-18 isotopic variants may be used for positron emission tomography.

Depending upon the substituents present in the compounds of the formula (I), the compounds may form esters, amides, carbamates and/or salts. Salts of compounds of formula (I) which are suitable for use in medicine are those wherein a counterion is pharmaceutically acceptable. Such pharmaceutically acceptable salts are described in standard texts on salt formation, see for example: P. Stahl, et al., Handbook of Pharmaceutical Salts: Properties, Selection and Use (VCHA/Wiley-VCH, 2002), or S. M. Berge, et al., "Pharmaceutical Salts" (1977) *Journal of Pharmaceutical Sciences*, 66, 1-19. However, salts having non-pharmaceutically acceptable counterions are within the scope of the present invention, for example, for use as intermediates in the preparation of the compounds of formula (I) and their pharmaceutically acceptable salts, and physiologically functional derivatives. By the term "physiologically functional derivative" is meant a chemical derivative of a compound of formula (I) having the same physiological function as the free compound of formula (I), for example, by being convertible in the body thereto. Esters, amides and carbamates are examples of physiologically functional derivatives.

Suitable salts according to the invention include those formed with organic or inorganic acids. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Other acids such as oxalic, while not in themselves pharmaceutically acceptable, may be useful as intermediates in obtaining the compounds of the invention and their pharmaceutical acceptable acid addition salts.

Compounds of formula (I) may have an appropriate group converted to an ester, an amide or a carbamate. Typical ester and amide and carbamate groups formed from an —OH or —NHR$^G$ group in the compound of the formula (I) include OC(O)R$^G$, NR$^G$C(O)R$^G$, NR$^G$CO$_2$R$^G$, OSO$_2$R$^G$, and —NR$^G$SO$_2$R$^G$, where R$^G$ is selected from the group consisting of C$_{1-8}$alkyl, C$_{2-8}$alkenyl, C$_{2-8}$alkynyl, C$_{3-8}$cycloalkyl and C$_{3-8}$cycloalkylC$_{1-8}$alkyl, haloC$_{1-8}$alkyl, dihaloC$_{1-8}$alkyl, trihaloC$_{1-8}$alkyl, phenyl and phenylC$_{1-4}$alkyl; more preferably R$^G$ is selected from the group consisting of C$_{1-8}$alkyl, C$_{2-6}$alkenyl, C$_2$alkynyl, C$_{3-8}$cycloalkyl and C$_{3-8}$cycloalkylC$_{1-8}$alkyl.

Those skilled in the art of organic chemistry will appreciate that many organic compounds can form complexes with solvents in which they are reacted, or from which they are precipitated or crystallized. These complexes are known as "solvates". A "Pharmaceutically acceptable solvate" means a molecular complex comprising the compound of the invention and one or more pharmaceutically acceptable solvent molecules, for example, water or ethanol. For example, a complex with water is known as a "hydrate". Solvates, such as hydrates, exist when the drug substance incorporates solvent, such as water, in the crystal lattice in either stoichiometric or non-stoichiometric amounts. Drug substances are routinely screened for the existence of hydrates since these may be encountered at any stage of the drug manufacturing process or upon storage of the drug substance or dosage form. Solvates are described in S. Byrn et al, Pharmaceutical Research 12(7), 1995, 954-954, and Water-Insoluble Drug Formulation, 2$^{nd}$ ed. R. Liu, CRC Press, page 553, which are incorporated herein by reference. Accordingly, it will be understood by the skilled person that the compounds of formula (I), as well as esters, amides, carbamates and/or salts thereof may therefore be present in the form of solvates, and these are also included within the scope of the present invention. Solvates of compounds of formula (I) which are suitable for use in medicine are those wherein the associated solvent is pharmaceutically acceptable. For example, as mentioned above, a hydrate is an example of a pharmaceutically acceptable solvate. However, solvates having non-pharmaceutically acceptable associated solvents may find use as intermediates in the preparation of the compounds of formula (I) and their pharmaceutically acceptable esters, amides, carbamates and/or salts thereof.

A compound which, upon administration to the recipient, is capable of being converted into a compound of formula (I) as described above, or an active metabolite or residue thereof, is known as a "prodrug". A prodrug may, for example, be converted within the body, e.g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference.

The following definitions apply to the terms as used throughout this specification, unless otherwise limited in specific instances.

As used herein, the term "$C_{1-x}$alkyl" means both straight and branched chain saturated hydrocarbon groups having 1 to X carbon atoms in the hydrocarbon chain. X may be, for example 8, 7, 6, 5, 4, 3, or 2. Preferably X is 8, 4 or 3. Examples of alkyl groups include methyl, ethyl, propyl, iso-propyl, butyl, tert-butyl, iso-butyl, sec-butyl, pentyl and hexyl groups. Among unbranched alkyl groups, there are preferred methyl, ethyl, propyl, iso-propyl, butyl groups. Among branched alkyl groups, there may be mentioned tert-butyl, iso-butyl, 1-ethylpropyl and 1-ethylbutyl groups.

As used herein, the term "$OC_{1-x}$alkyl" means an alkoxy group, where "$C_{1-x}$alkyl" is used as described above. Examples of $OC_{1-x}$alkyl groups include O-methyl ($OC_1$alkyl, methoxy) and O-ethyl ($OC_2$alkyl, ethoxy) groups. Other examples include O-propyl ($OC_3$alkyl, propoxy) and O-butyl ($OC_4$alkyl, butoxy).

As used herein, the term "halogen" means fluorine, chlorine, bromine or iodine. Fluorine, chlorine and bromine are particularly preferred, and fluorine and chlorine are especially preferred.

As used herein, the term "$C_{1-x}$alkyl substituted with 1, 2 or 3 halogens or OH groups" means an alkyl group having 1, 2 or 3 halogen or OH group substituents, the terms "$C_{1-x}$alkyl" and "halogen" being understood to have the meanings outlined above. Thus, a "$C_{1-x}$alkyl substituted with 1, 2 or 3 halogens or OH groups" may have 1, 2 or 3 halogen substituents; 1, 2, or 3 OH group substituents; 1 or 2 halogen substituents and 1 OH group substituent; or 1 or 2 OH group substituents and 1 halogen substituent. Examples of $C_{1-8}$-alkyl substituted with 1 halogen include fluoromethyl, chloromethyl, bromomethyl, fluoroethyl, fluoropropyl and fluorobutyl groups; examples of $C_{1-8}$-alkyl substituted with 2 halogens include difluoromethyl and difluoroethyl groups; examples of $C_{1-8}$alkyl substituted with 3 halogens include trifluoromethyl and trifluoroethyl groups. Examples of $C_{1-8}$-alkyl substituted with 1 OH group include $CH_2H$, $(CH_2)_2OH$, $(CH_2)_3OH$, $(CH_2)_4OH$, $(CH_2)_5OH$, $(CH_2)_6OH$, $CH(CH_3)CH_2H$, $CH_2CH(CH_3)CH_2OH$ and $C(CH_3)_2CH_2OH$ groups; examples of $C_{1-8}$-alkyl substituted with 2 OH groups include $CH(OH)_2$, $CH(OH)CH_2H$, $C(OH)_2CH_3$, and $CH_2CH(OH)_2$ groups; examples of $C_{1-8}$-alkyl substituted with 3 OH groups include $C(OH)_3$, $CH(OH)CH(OH)_2$, $C(OH)_2CH_2OH$ and $CH_2C(OH)_3$ groups.

As used herein, the term "$OC_{1-x}$alkyl substituted with 1, 2 or 3 halogens or OH groups" means an alkoxy group having 1, 2 or 3 halogen or OH substituents, the terms "alkyl" and "halogen" being understood to have the meanings outlined above. Thus, a "$OC_{1-x}$alkyl substituted with 1, 2 or 3 halogens or OH groups" may have 1, 2 or 3 halogen substituents; 1, 2, or 3 OH group substituents; 1 or 2 halogen substituents and 1 OH group substituent; or 1 or 2 OH group substituents and 1 halogen substituent. Examples of $OC_{1-8}$-alkyl substituted with 1 halogen include fluoromethoxy, chloromethoxy, bromomethoxy, fluoroethoxy, fluoropropoxy and fluorobutoxy groups; examples of $OC_{1-8}$-alkyl substituted with 2 halogens include difluoromethoxy and difluoroethoxy groups; examples of $OC_{1-8}$alkyl substituted with 3 halogens include trifluoromethoxy and trifluoroethoxy groups.

As used herein, the term "aromatic heterocycle" means an aromatic cyclic group of carbon atoms wherein from 1 to 3 of the carbon atoms is/are replaced by one or more heteroatoms independently selected from nitrogen (N), oxygen (O) or sulfur (S). A 5- or 6-membered aromatic heterocycle is monocyclic. A heteroatom may be S, O or N and is preferably S or N. Heterocyclyl groups containing a suitable nitrogen atom include the corresponding N-oxides.

Examples of 5- or 6-membered aromatic heterocycle groups comprising 1, 2 or 3 heteroatoms include furanyl, pyrrolyl, thiophenyl, pyridinyl, imidazolyl (1,3-diazolyl), pyrazolyl (1,2-diazolyl), 1,3-oxazolyl, isoxazolyl (1,2-oxazolyl), thiazolyl (1,3-thiazolyl), isothiazolyl (1,2-thiazolyl), 1H-1,2,3-triazolyl, 2H-1,2,3-triazolyl, 1H-1,2,4-triazolyl, 4H-1,2,4-triazolyl, furazanyl (1,2,5-oxadiazolyl), 1,2,3-oxadiazolyl, 1,2,4-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), pyrazinyl (1,4-diazinyl), 1,2,3-triazinyl, 1,2,4-triazinyl, and 1,3,5-triazinyl.

Examples of 5- or 6-membered aromatic heterocycle groups comprising 2 or 3 heteroatoms include imidazolyl (1,3-diazolyl), pyrazolyl (1,2-diazolyl), 1,3-oxazolyl, isoxazolyl (1,2-oxazolyl), thiazolyl (1,3-thiazolyl), isothiazolyl (1,2-thiazolyl), 1H-1,2,3-triazolyl, 2H-1,2,3-triazolyl, 1H-1,2,4-triazolyl, 4H-1,2,4-triazolyl, furazanyl (1,2,5-oxadiazolyl), 1,2,3-oxadiazolyl, 1,2,4-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), pyrazinyl (1,4-diazinyl), 1,2,3-triazinyl, 1,2,4-triazinyl, and 1,3,5-triazinyl.

As mentioned above, the compounds of the invention have activity as A2a receptor ligands. The compounds of the invention have activity as A2a receptor modulators, and more specifically are antagonists of the A2a receptor. Preferred compounds of the invention are selective antagonists of the A2a receptor. "Selective", in this context, means any compound of the invention that binds to an A2a receptor in preference to one or more of the other adenosine receptor sub-types (adenosine 1 (A1) receptor, adenosine 2b (A2b) receptor and adenosine 3 (A3) receptor). It is especially preferred that the compounds of the invention bind to an A2a receptor in preference to at least the A1 receptor and/or the A3 receptor. It is very especially preferred that the compounds of the invention bind to an A2a receptor in preference to at least the A1 receptor.

Preferably, the compounds of the invention are selective antagonists of the A2a receptor over the A2b receptor; and/or selective antagonists of the A2a receptor over the A1 receptor; and/or selective antagonists of the A2a receptor over the A3 receptor (for example selective as assessed using $IC_{50}$ levels (e.g. SPR $IC_{50}$ values), as mentioned below). For example, the compounds of the invention are selective antagonists of the A2a receptor over the A1 receptor (for example selective as assessed using $IC_{50}$ levels (e.g. SPR $IC_{50}$ values), as mentioned below). More preferably, the compounds of the invention are selective antagonists of the A2a receptor over at least two of: the A2b receptor; the A1 receptor; and the A3 receptor (for example selective as assessed using $IC_{50}$ levels (e.g. SPR $IC_{50}$ values), as mentioned below). For example, the compounds of the invention are selective antagonists of the A2a receptor over the A1 receptor and the A3 receptor (for example selective as assessed using $IC_{50}$ levels, as mentioned below). Most preferably, the compounds of the invention are selective antagonists of the A2a receptor over the A2b receptor, the A1 receptor, and the A3 receptor (for example selective as assessed using $IC_{50}$ levels (e.g. SPR $IC_{50}$ values), as mentioned below).

For example, as assessed by $IC_{50}$ values (e.g. SPR $IC_{50}$ values), the selectivity for the A2a receptor is at least 2 times that for one or more of the other adenosine receptor sub-types, preferably at least 5 times, more preferably at least 10 times, more preferably at least 20 times, more preferably at least 50 times, more preferably at least 60 times, more preferably at least 70 times and even more preferably at least 100 times, for example at least 150 times, at least 200 times, at least 300 times, at least 500 times, at least 1000 times, at least 2000 times, at least 3000 times, at least 4000 times, at least 5000 times, at least 6000 times, at least 7000 times, at least 8000 times, at least 9000 times, at least 10,000 times, or at least 20,000 times.

In one preferred embodiment, as assessed by $IC_{50}$ values (e.g. SPR $IC_{50}$ values), the selectivity for the A2a receptor is at least 60 times that for one or more of the other adenosine receptor sub-types. In another preferred embodiment the selectivity for the A2a receptor is at least 70 times that for one or more of the other adenosine receptor sub-types. In a further preferred embodiment the selectivity for the A2a receptor is at least 100 times that for one or more of the other adenosine receptor sub-types. In another preferred embodiment the selectivity for the A2a receptor is at least 1000 times that for one or more of the other adenosine receptor sub-types. In another preferred embodiment, the selectivity for the A2a receptor is at least 10,000 times that for one or more of the other adenosine receptor sub-types.

In certain very preferred embodiments, as assessed by $IC_{50}$ values (e.g. SPR $IC_{50}$ values), the selectivity for the A2a receptor is at least 2 times that for the A1 receptor sub-type, preferably at least 5 times, more preferably at least 10 times, more preferably at least 20 times, more preferably at least 50 times, more preferably at least 60 times, more preferably at least 70 times and even more preferably at least 100 times, for example at least 150 times, at least 200 times, at least 300 times, or at least 500 times. In one preferred embodiment, as assessed by $IC_{50}$ values (e.g. SPR $IC_{50}$ values), the selectivity for the A2a receptor is at least 60 times that for the A1 receptor sub-type. In another preferred embodiment, the selectivity for the A2a receptor is at least 70 times that for the A1 receptor sub-type. In another preferred embodiment, the selectivity for the A2a receptor is at least 100 times that for the A1 receptor sub-type. In another preferred embodiment, the selectivity for the A2a receptor is at least 500 times that for the A1 receptor sub-type.

In certain preferred embodiments, as assessed by $IC_{50}$ values (e.g. SPR $IC_{50}$ values), the selectivity for the A2a receptor is at least 2 times that for the A3 receptor sub-type, preferably at least 5 times, more preferably at least 10 times, more preferably at least 20 times, more preferably at least 50 times and even more preferably at least 100 times, for example at least 150 times, at least 200 times, at least 300 times, at least 500 times, at least 1000 times, at least 2000 times, at least 3000 times, at least 4000 times, at least 5000 times, at least 6000 times, at least 7000 times, at least 8000 times, at least 9000 times, at least 10,000 times, or at least 20,000 times. In another preferred embodiment, as assessed by $IC_{50}$ values (e.g. SPR $IC_{50}$ values), the selectivity for the A2a receptor is at least 100 times that for the A3 receptor sub-type. In one preferred embodiment, the selectivity for the A2a receptor is at least 1000 times that for the A3 receptor sub-type. In a further preferred embodiment, the selectivity for the A2a receptor is at least 4000 times that for the A3 receptor sub-type. In another preferred embodiment, the selectivity for the A2a receptor is at least 5000 times that for the A3 receptor sub-type. In another preferred embodiment, the selectivity for the A2a receptor is at least 10,000 times that for the A3 receptor sub-type.

Preferred compounds of the present invention have good affinity for the A2a receptor (i.e. have a low $IC_{50}$ concentration for the A2a receptor measured using the SPR assay mentioned below). For example, preferably compounds of the invention have an $IC_{50}$ value for the A2a receptor measured using the SPR assay mentioned below, of less than 1 μM, preferably less than 0.5 μM, preferably less than 0.1 μM, more preferably less than 0.05 μM, and most preferably less than 0.02 μM, for example less than 0.01 μM, for example less than 0.008 μM, for example less than 0.005 μM, for example less than 0.004 μM, for example less than 0.003 μM or for example less than 0.002 μM. In one especially preferred embodiment, compounds of the invention have an $IC_{50}$ value for the A2a receptor measured, using the SPR assay mentioned below, of less than 0.01 μM.

Alternatively, or additionally, preferably compounds of the invention have good functional activity for the A2a receptor (i.e. have an $EC_{50}$ value for the A2a receptor measured using the cAMP assay mentioned below). For example, preferably compounds of the invention have an $EC_{50}$ value for the A2a receptor measured using the cAMP assay mentioned below, of less than 10 μM, preferably less than 5 μM, preferably less than 2 μM, more preferably less than 1.5 μM, and more preferably less than 1 μM, for example less than 0.5 μM, for example less than 0.4 μM, for example less than 0.3 μM, for example less than 0.2 μM, for example less than 0.1 μM, for example less than 0.08 μM, for example less than 0.05 μM, less than 0.04 μM, for example less than 0.03 μM, for example less than 0.02 μM, for example less than 0.01 μM, or for example less than 0.005 μM. In one especially preferred embodiment, compounds of the invention have an $EC_{50}$ value for the A2a receptor measured using the cAMP assay mentioned below, of less than 1 μM.

Especially preferred compounds of the invention have an $IC_{50}$ value for the A2a receptor measured using the SPR assay mentioned below of less than 0.1 μM (for example less than 0.05 μM, for example less than 0.01 μM, or for example less than 0.01 μM) and an $EC_{50}$ value for the A2a receptor measured using the cAMP assay mentioned below, of less than 2 μM (for example less than 1 μM, less than 0.5 μM, less than 0.1 μM, less than 0.05 μM, or less than 0.0005 μM).

Especially preferred compounds of the invention are selective for the A2a receptor, and/or have good affinity and/or good functional activity for the A2a receptor; in combination with having good pharmacokinetic properties, for example good metabolic stability. Pharmacokinetic properties of a compound, such as metabolic stability, may be determined by one of ordinary skill in the art using routine methods (for example measuring stability of the compound when exposed to commercially available liver microsomes (e.g. mouse liver microsomes), plasma enzymes, etc.).

Especially preferred compounds of the invention are selective for the A2a receptor and/or have good affinity the A2a receptor; in combination with having an acceptable level of solubility for pharmaceutical use. For example, the preferred compounds of the invention have a solubility of greater than 0.001 mg/mL. More preferred compounds of the invention have a solubility of greater than 0.003 mg/mL, more preferably greater than 0.005 mg/mL, more preferably greater than 0.010 mg/mL, more preferably greater than 0.020 mg/mL, more preferably greater than 0.050 mg/mL, and even more preferably greater than 0.100 mg/mL.

Very preferred compounds of the invention are selective for the A2a receptor, and/or have good affinity and/or good functional activity for the A2a receptor; in combination with having good solubility and good pharmacokinetic properties (for example good solubility and good metabolic stability).

The invention also provides a compound according to the invention, or a composition comprising a compound according to the invention, for use as a medicament, or for use in therapy. For example, the invention provides a compound according to the invention, or a composition comprising a compound according to the invention, together with a pharmaceutically acceptable carrier, for use as a medicament, or for use in therapy.

For the avoidance of doubt, as used herein the terms "therapy", "treatment" and "treating" include both preventative and curative treatment of a condition, disease or disorder. It also includes slowing, interrupting, controlling or stopping the progression of a condition, disease or disorder. It also includes preventing, curing, slowing, interrupting, controlling or stopping the symptoms of a condition, disease or disorder.

A compound of the invention, or a composition comprising a compound of the invention, may be used in the treatment of diseases or disorders associated with A2a receptor activity. In particular, the compounds of the invention may be used in the treatment or prophylaxis of diseases or disorders for which selective antagonists of the A2a receptor are indicated. In particular, compounds of the invention may be used in the treatment or prophylaxis of a disease or disorder associated with the A2a receptor.

The compounds of the invention find particular application in the treatment or prophylaxis of a disease or disorder associated with the A2a receptor, which is a disease or disorder selected from the group consisting of cancer, neurodegenerative diseases, retinal degenerative diseases (for example glaucoma or diabetic retinopathy), insomnia, pain, psychiatric diseases (for example anxiety, depression, schizophrenia, attention or deficit hyperactivity disorder), ischemia (for example ischemic stroke or myocardial ischemia), infarction (for example myocardial infarction, cerebral infarction (stoke), lung infarction, spleen infarction, kidney infarction, bowel infarction, or placental infarction), acute inflammatory diseases (for example trauma, wound healing, or bacterial infections), chronic inflammatory diseases (for example appendicitis, asthma, bursitis, chronic peptic ulcer, colitis, cystitis, dermatitis, encephalitis, gingivitis, meningitis, myelitis, nephritis, neuritis, periodontitis, phlebitis, prostatitis, rhinitis, sinusitis, tendonitis, testiculitis, tonsillitis, ulcerative colitis and Crohn's disease, urethritis, vasculitis, rheumatoid arthritis, ankylosing spondylitis and psoriatic arthritis), spinal cord injury, and epilepsy. In another embodiment, the disease or disorder associated with the A2a receptor is a disease or disorder selected from the group consisting of autoimmune, inflammatory, cancer, infectious, metabolic, developmental, cardiovascular, liver, intestinal, endocrine, or neurological disease.

In certain preferred embodiments, the compounds of the invention find application in the treatment of cancer. As used herein, the term "cancer" refers to all types of cancer, neoplasm or malignant tumours found in mammals, including leukaemias, lymphomas, melanomas, neuroendocrine tumours, carcinomas and sarcomas. The compounds of the invention find application in the treatment of a cancer in which tumour growth and/or survival is dependent upon or assisted by agonism of the A2a receptor.

In particular, the compounds of the invention find application in the treatment of a cancer selected from the group consisting of lymphoma (for example B cell lymphoma), sarcoma (for example osteosarcoma), bladder cancer, bone cancer, brain tumour, cervical cancer, renal cell cancer, colorectal cancer (for example colon cancer or colorectal cancer with microsatellite instability), esophageal cancer, gastric cancer, head and neck cancer, kidney cancer, myeloma, thyroid cancer, leukaemia (for example acute myeloid leukaemia), breast cancer (e.g. triple negative, ER positive, ER negative, chemotherapy resistant, Herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer (for example castration-resistant prostate cancer), glioblastoma, squamous cell carcinoma (e.g. head, neck, or esophagus), multiple myeloma, skin cancer (e.g. Merkel cell carcinoma), testicular cancer, neuroblastoma and metastatic cancer.

More especially, the compounds of the invention find application in the treatment of a cancer selected from the group consisting of lung cancer, ovarian cancer, osteosarcoma, bladder cancer, cervical cancer, liver cancer, kidney cancer, skin cancer (e.g. Merkel cell carcinoma), testicular cancer, leukaemia, lymphoma, head and neck cancer, renal cell cancer, colorectal cancer (e.g. colorectal cancer with microsatellite instability), prostate cancer, pancreatic cancer, melanoma, breast cancer, and neuroblastoma.

The compounds of the invention also find particular application in the treatment of a cancer selected from the group consisting of prostate cancer (in particular castration-resistant prostate cancer), renal cell cancer, metastatic cancer, melanoma, castration-resistant prostate cancer, breast cancer, triple negative breast cancer, glioblastoma, ovarian cancer, lung cancer, squamous cell carcinoma (e.g. head, neck, or esophagus), colorectal cancer (e.g. colorectal cancer with microsatellite instability), leukaemia (for example acute myeloid leukaemia), lymphoma (for example B cell lymphoma), and multiple myeloma.

The compounds of the invention also find particular application in the treatment of non-small cell lung cancer, melanoma, renal cell cancer, triple-negative breast cancer, bladder cancer, head and neck cancer and colorectal cancer (especially colorectal cancer with microsatellite instability).

The compounds of the invention may additionally or alternatively find application in the treatment of a cancer selected from the group consisting of cancer of the thyroid, endocrine system, brain, breast, cervix, colon, head and neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumours, cancer, malignant pancreatic insulanoma, malignant carcinoid, urinary bladder cancer, pre-malignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumours, Lobular Carcinoma, Ductal Carcinoma, cancer of the pancreatic stellate cells, cancer of the hepatic stellate cells, and prostate cancer.

A "leukaemia" is a progressive, malignant disease of the blood-forming organs and is generally characterized by a distorted proliferation and development of leukocytes and their precursors in the blood and bone marrow. Leukaemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or leukemic (sub-leukemic). Examples of leukaemias that may be treated with a compound, or pharmaceutical composition include, for example, acute nonlymphocytic leukaemia, lymphocytic leukaemia (for example chronic lymphocytic leukaemia), acute granulocytic leukaemia, chronic granulocytic leukaemia, acute promyelocytic leukaemia, adult T-cell leukaemia, aleukaemic leukaemia, aleukocythemic leukaemia, basophylic leukaemia, blast cell leukaemia, bovine leukaemia, myelocytic leukaemia (for example chronic myelocytic leukaemia), leukaemia cutis, embryonal leukaemia, eosinophilic leukaemia, Gross' leukaemia, hairy-cell leukaemia, hemoblastic leukaemia, hemocytoblastic leukaemia, histiocytic leukaemia, stem cell leukaemia, monocytic leukaemia (for example acute monocytic leukaemia), leukopenic leukaemia, lymphoblastic leukaemia, lymphosarcoma cell leukaemia, mast cell leukaemia, megakaryocyte leukaemia, micromyeloblastic leukaemia, myeloblastic leukaemia, myeloid granulocytic leukaemia, myelomonocytic leukaemia, Naegeli leukaemia, plasma cell leukaemia, plasmacytic leukaemia, promyelocytic leukaemia, Rieder cell leukaemia, Schilling's leukaemia, stem cell leukaemia, subleukemic leukaemia, and undiffereentiated cell leukaemia.

A "sarcoma" is a tumour which is made up of a substance like the embryonic connective tissue and is generally composed of closely packed cells embedded in a fibrillar or homogeneous substance. Examples of sarcomas that may be treated with a compound, or pharmaceutical composition include, for example, chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

A "melanoma" is a tumor arising from the melanocytic system of the skin and other organs. Examples of melanomas that may be treated with a compound, or pharmaceutical composition include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

A "carcinoma" is a malignant growth made up of epithelial cells tending to infiltrate the surrounding tissues and give rise to metastases. Examples of carcinomas that may be treated with a compound, or pharmaceutical composition include, for example, medullary thyroid carcinoma, familial medullary thyroid carcinoma, acinar carcinoma, acinous carcinoma, adenoid cystic carcinoma, carcinoma adenomatosum, carcinoma of adrenal cortex, alveolar carcinoma, basal cell carcinoma, basaloid carcinoma, basosquamous cell carcinoma, alveolar/bronchiolar carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, gelatinous carcinoma, giant cell carcinoma, carcinoma glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, medullary carcinoma, melanotic carcinoma, mucinous carcinoma, mucoepidermoid carcinoma, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous cell carcinoma, string carcinoma, carcinoma telangiectodes, transitional cell carcinoma, tubular carcinoma, tuberous carcinoma, verrucous carcinoma, and carcinoma villosum.

A "metastasis", "metastases", "metastatic", and "metastatic cancer" can be used interchangeably and refer to the spread of a cancer from one organ or another non-adjacent organ or body part. Cancer occurs at an originating site, e.g. breast, which site is referred to as a primary tumour, e.g. primary breast cancer. Some cancer cells in the primary tumour or originating site acquire the ability to penetrate and infiltrate surrounding normal tissue in the local area and/or the ability to penetrate the walls of the lymphatic system or vascular system circulating through the system to other sites and tissues in the body. A second clinically detectable tumour formed from cancer cells of a primary tumour is referred to as a metastatic or secondary tumour. When cancer cells metastasize, the metastatic tumour and its cells are presumed to be similar to those of the original tumour. Thus, if lung cancer metastasizes to the breast, the secondary tumour at the site of the breast consists of abnormal lung cells and not abnormal breast cells. The secondary tumour in the breast is referred to a metastatic lung cancer. Thus, the phrase metastatic cancer refers to a disease in which a subject has or had a primary tumour and has one or more secondary tumours. The phrases 'non-metastatic cancer' or 'subjects with cancer that is not metastatic' refers to diseases in which subjects have a primary tumour but not one or more secondary tumours. For example, metastatic lung cancer refers to a disease in a subject with a history of a primary lung tumour and with one or more secondary tumours at a second location or multiple locations, e.g. in the breast.

The invention also provides a method for the treatment or prophylaxis of a disease or disorder associated with A2a receptor activity in a mammal, which comprises administering to the mammal a therapeutically effective amount of a compound according to the invention, or a composition comprising a compound according to the invention together with a pharmaceutically acceptable carrier. Clinical conditions mediated by an A2a receptor antagonist or partial antagonist that may be treated by the method of the invention are preferably those described above.

The invention also provides the use of a compound according to the invention, for the manufacture of a medicament for the treatment or prophylaxis of a disease or disorder associated with the A2a receptor. Clinical conditions mediated by an A2a receptor ligand that may be treated by the method of the invention are preferably those described above.

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Advantageously, compounds of the invention may be administered in a single daily dose, or the total daily dosage may be administered in divided doses of two, three or four times daily. Furthermore, preferred compounds for the invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

While it is possible for the active ingredient to be administered alone, it is preferable for it to be present in a pharmaceutical formulation or composition. Accordingly, the invention provides a pharmaceutical formulation or composition comprising a compound according to the invention, and a pharmaceutically acceptable diluent, excipient or carrier (collectively referred to herein as "carrier" materials). Pharmaceutical compositions of the invention may take the form of a pharmaceutical formulation as described below.

The pharmaceutical formulations according to the invention include those suitable for oral, parenteral (including subcutaneous, intradermal, intramuscular, intravenous [bolus or infusion], and intraarticular), inhalation (including fine particle dusts or mists which may be generated by means of various types of metered dose pressurized aerosols), nebulizers or insufflators, rectal, intraperitoneal and topical (including dermal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The compounds of the invention can, for example, be administered in a form suitable for immediate release or extended release. Immediate release or extended release can be achieved by the use of suitable pharmaceutical compositions comprising a compound of the present invention, or, particularly in the case of extended release, by the use of devices such as subcutaneous implants or osmotic pumps.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Disintegrators include without limitation starch, methylcellulose, agar, bentonite, xanthan gum and the like. The compounds of formula (I) can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g. Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

The compounds of the present invention can also be administered in the form of liposome delivery systems, such as small unilamellar vesicles, large unilamellar vesicles and multilamellar vesicles. Liposomes can be formed from a variety of phospholipids, 1,2-dipalmitoylphosphatidylcholine, phosphatidyl ethanolamine (cephaline), or phosphatidylcholine (lecithin).

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

Whilst a compound of the invention may be used as the sole active ingredient in a medicament, it is also possible for the compound to be used in combination with one or more further therapeutic agents. Thus, the invention also provides a compound according to the invention together with a further therapeutic agent, for simultaneous, sequential or separate administration. Such further therapeutic agents may be further compounds according to the invention, or they may be different therapeutic agents, for example another A2a receptor antagonist (and in particular an A2a receptor antagonist selected from the group consisting of ATL-444, istradefylline (KW-6002), MSX-3, preladenant (SCH-420, 814), SCH-58261, SCH-412348, SCH-442416, ST-1535, Caffeine, CPI-444 (VER-6623), VER-6947, VER-7835, vipadenant (BIIB-014), tozadenant, AZD4635 (HTL-1071), PBF-509 and ZM-241,385). The further therapeutic agent may also be a therapeutic agent for use in the prevention or treatment of a disease or disorder associated with the A2a receptor, for example a disease or disorder selected from the group consisting of cancer, neurodegenerative diseases, retinal degenerative diseases, insomnia, pain, psychiatric diseases, ischemia, infarction, acute inflammatory diseases, chronic inflammatory diseases, spinal cord injury, and epilepsy.

The further therapeutic agent may also be different therapeutic agent for use in the treatment of cancer, for example alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, esperamicin, chromoprotein enediyne antibiotic chromophores, aclacinomysins, actinomycin, authramycin, azaserine, bleomycins, cactinomycin, carabicin, carminomycin, carzinophilin, checkpoint inhibitors (e.g. anti-PD antibodies, anti-PD Li antibodies), chromomycinis, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; antimetabolites, erlotinib, vemurafenib, crizotinib, sorafenib, ibrutinib, enzalutamide, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid 2-ethylhydrazide, procarbazine, PSK® polysaccharide complex (JHS Natural Products, Eugene, Oreg.), razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, chloranbucil; gemcitabine; 6-thioguanine; mercaptopurine; methotrexate; platinum analogs, vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (Camptosar, CPT-11), topoisomerase inhibitor RFS 2000; difluorometlhylornithine; retinoids; capecitabine; combretastatin; leucovorin; oxaliplatin; inhibitors of PKC-alpha, Raf, H-Ras, EGFR and VEGF-A that reduce cell proliferation; or pharmaceutically acceptable salts, acids or derivatives thereof; or a combination thereof.

The compounds of the present invention can be used in combination with other agents useful for treating A2a receptor-mediated conditions. The individual components of such combinations can be administered separately at different times during the course of therapy or concurrently in divided or single combination forms. The present invention is therefore to be understood as embracing all such regimes of simultaneous or alternating treatment and the term "administering" is to be interpreted accordingly. It will be understood that the scope of combinations of the compounds of this invention with other agents useful for treating A2a receptor-mediated conditions includes in principle any combination with any pharmaceutical composition useful for treating a disease or disorder related to the A2a receptor.

The above other therapeutic agents, when employed in combination with the compounds of the present invention, may be used, for example, in those amounts indicated in the Physicians' Desk Reference (PDR) or as otherwise determined by one of ordinary skill in the art.

The compounds of the invention as described above also find use, optionally in labelled form, as a diagnostic agent for the diagnosis of conditions associated with a disease or disorder associated with A2a receptor activity. For example, such a compound may be radioactively labelled.

The compounds of the invention as described above, optionally in labelled form, also find use as a reference compound in methods of identifying ligands for the A2a receptor (i.e. discovering other antagonists or partial antagonists, or agonists, or partial agonists, of the A2a receptor). Thus, the invention provides a method of identifying an A2a receptor ligand which comprises use of a compound of the invention or a compound of the invention in labelled form, as a reference compound. For example, such a method may involve a competitive binding experiment in which binding of a compound of the invention to the A2a receptor is reduced by the presence of a further compound which has A2a receptor-binding characteristics, for example stronger A2a receptor-binding characteristics than the compound of the invention in question.

General Synthetic Methodology

The methods used for the synthesis of the compounds of the invention are illustrated by the schemes below. The starting materials and reagents used in preparing these compounds are available from commercial suppliers or can be prepared by methods routine to those skilled in the art.

General Method 1A

The invention also provides a process for the preparation of A2a receptor antagonists where $R^1$ and $R^2$ are defined according to the invention. The process involves reacting an appropriate 3-amino-1-arylmethylpyrazole-4-carbonitrile with an aryl nitrile in the presence of potassium t-butoxide in 1,4-dioxane or THF at a temperature of 60-100° C. (for example 70-100° C., 75-100° C., or 80-100° C.).

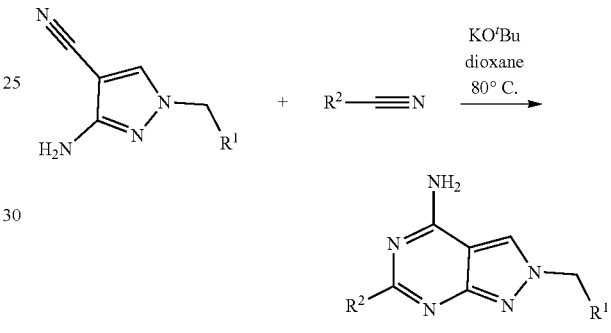

General Method 1B

The invention also provides a process for the preparation of A2a receptor antagonists where $R^1$ and $R^2$ are defined according to the invention. The process involves reacting an appropriate 3-amino-1-arylmethylpyrazole-4-carbonitrile with an aryl nitrile in the presence of potassium t-butoxide in 1,4-dioxane under microwave conditions at 120° C.

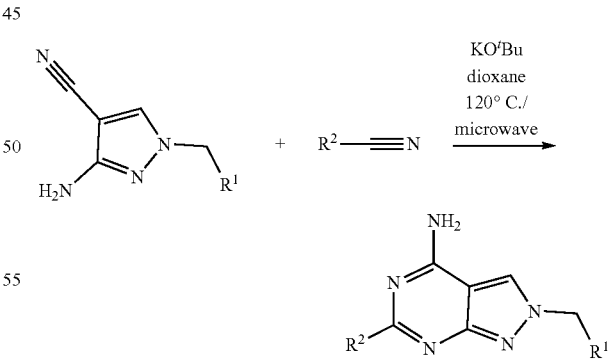

General Method 2

The invention also provides a process for the preparation of A2a receptor antagonists where $R^1$ is a phenyl ring bearing a OH substituent and $R^2$ is defined according to the invention. The process involves reacting an appropriate methoxyphenyl-substituted pyrazolopyrimidine with boron tribromide in DCM at room temperature.

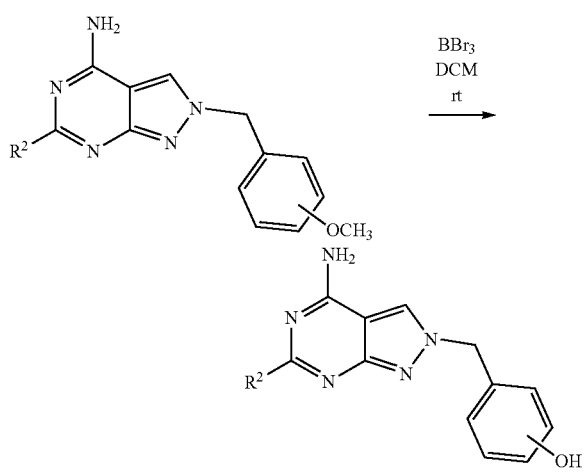

General Method 3

The invention also provides a process for the preparation of A2a receptor antagonists where $R^2$ is defined according to the invention. The process involves reacting an appropriate carboxyphenyl-substituted pyrazolopyrimidine with lithium aluminium hydride in THF at room temperature.

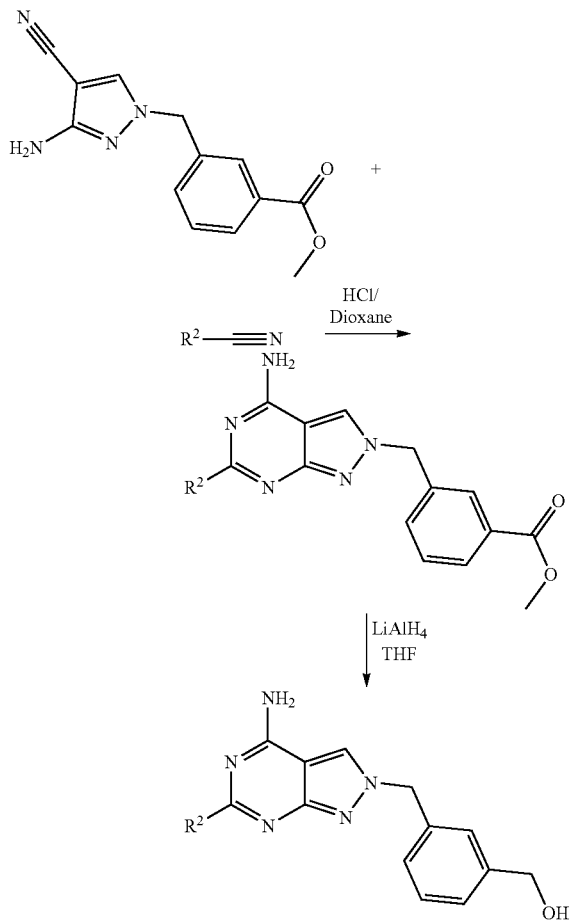

Numerous synthetic routes to the compounds of the present invention can be devised by any person skilled in the art and the possible synthetic routes described below do not limit the invention. A number of possible synthetic routes are shown schematically below.

The following Examples illustrate the invention.

EXAMPLES

General Experimental Details

LC-MS: Target compounds were analysed on an LC-MS system equipped with a Waters CSH C18 5 µm (50×2.1 mm) column at a temperature of 55° C., using a gradient elution of acetonitrile in water containing 0.02% formic acid (2-98% over 4 min then 98% acetonitrile for 0.5 min). MS ionisation mode was positive electrospray. Intermediates were analysed using the same column conditions but utilising 0.05% TFA as the acidic modifier NMR: $^1$H NMR spectra were recorded on 500 MHz instruments at room temperature unless specified otherwise were referenced to residual solvent signals. Data are presented as follows: chemical shift in ppm, integration, multiplicity (br=broad, app=apparent, s=singlet, d=doublet, t=triplet, q=quartet, p=pentet, m=multiplet) and coupling constants in Hz.

PREPARATION OF INTERMEDIATES 1-22

Intermediate 1

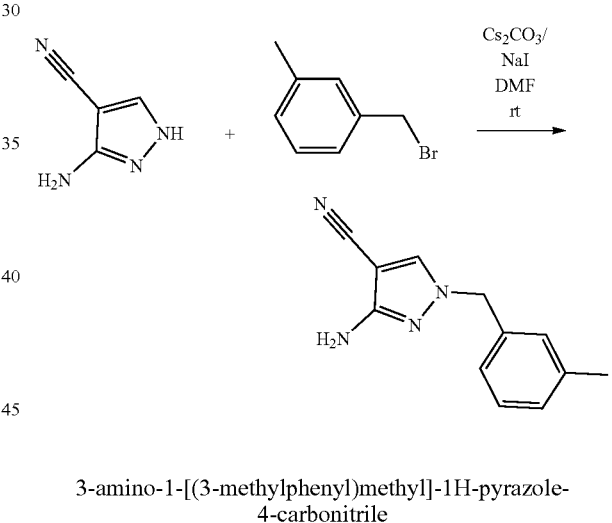

3-amino-1-[(3-methylphenyl)methyl]-1H-pyrazole-4-carbonitrile

In a three necked round-bottom flask, under nitrogen, was added 3-amino-1H-pyrazole-4-carbonitrile (8.0 g, 74.0 mmol) in DMF (300 mL) followed by cesium carbonate (31.3 g, 96.2 mmol) and a quick dropwise addition of 1-(bromomethyl)-3-methylbenzene (13 mL, 96.2 mmol). The reaction mixture was stirred 18 h at room temperature and then filtered under talcum powder and washed several times with EtOAc After addition of water, the layers were separated and the aqueous layer was extracted once with EtOAc. The organics layers were dried (Na$_2$SO$_4$), filtered and concentrated in vacuum to afford a yellow oil. This residue was triturated with EtOH until precipitation occurred. The solid was filtered and washed with EtOH. The filtrate was evaporated, and the residue is crystallized from i-PrOH to afford a second batch of title compound. The two batches of desired product are combined to give 6.05 g of the title compound as a white powder (yield: 39%).

LCMS [M+H]+ 213.2 observed at rt=1.11 min. 1H NMR (500 MHz, DMSO-d6): δ 8.22 (s, 1H), 7.23 (t, J=7.6 Hz, 1H), 7.11 (d, J=7.6 Hz, 1H), 7.06 (s, 1H), 7.03 (d, J=7.7 Hz, 1H), 5.55 (brs, 2H), 5.03 (s, 2H), 2.28 (s, 3H).

Intermediate 9

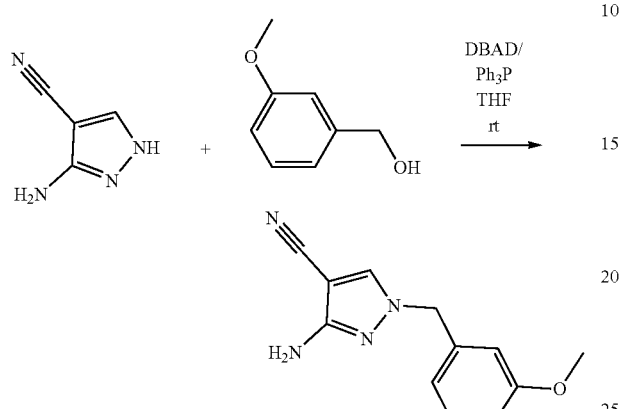

3-amino-1-[(3-methoxyphenyl)methyl]-1H-pyrazole-4-carbonitrile

In a three necked round-bottom flask, under nitrogen, was added 3-amino-1H-pyrazole-4-carbonitrile (0.940 g, 8.69 mmol) in THF (45 mL) followed by triphenylphosphine (2.85 g, 10.86 mmol) and (3-methoxyphenyl)methanol (0.9 mL, 7.24 mmol). The mixture was stirred 5 minutes at room temperature and then di-tert-butyl-azodicarboxylate (2.5 g, 10.86 mmol) was added. The reaction mixture was stirred at room temperature for 2 h15 and then concentrated to dryness. The residue was purified by Flash Chromatography (Redisep column 120 g, eluent: Heptane/EtOAc 90/10 to 60/40) to obtain the title compound (778 mg) as a yellow oil (yield: 47%).

LCMS: [M+H]+ 229.2 observed at rt=1.01 min. 1H NMR (500 MHz, DMSO-d6): δ 8.22 (s, 1H), 7.26 (t, J=7.9 Hz, 1H), 6.87 (dd, J=8.2, 2.5 Hz, 1H), 6.82-6.80 (m, 1H), 6.79 (d, J=7.7 Hz, 1H), 5.56 (s, 2H), 5.04 (s, 2H), 3.73 (s, 3H).

Intermediates 2-8 and 22 were prepared using a similar method to intermediate 1. Intermediates 10-21 were prepared using a similar method to that used for intermediate 9. In some cases e.g. intermediates 4, 5, 8, 11 and 21, separation of the regioisomeric pyrazole intermediates proved challenging and the mixture of regiosomers was used to prepare the Example compounds. The structures of Intermediates 2 to 22 are as follows:

Intermediate 2

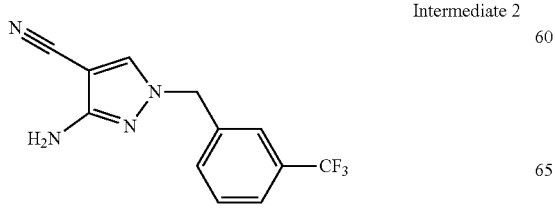

Intermediate 3

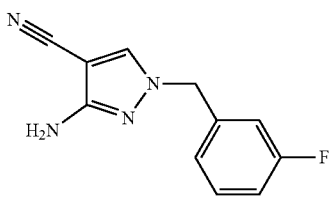

Intermediate 4

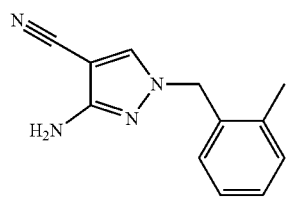

Intermediate 5

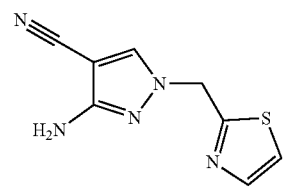

Intermediate 6

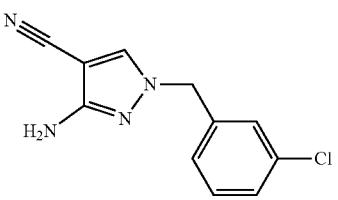

Intermediate 7

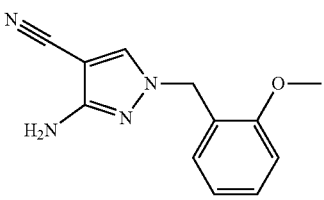

Intermediate 8

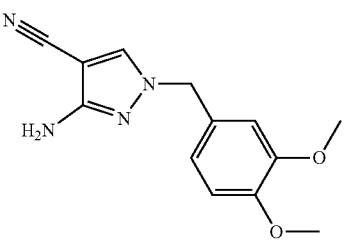

Intermediate 9

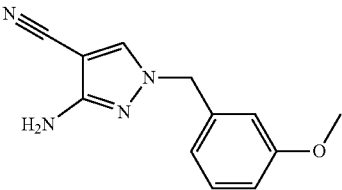

-continued
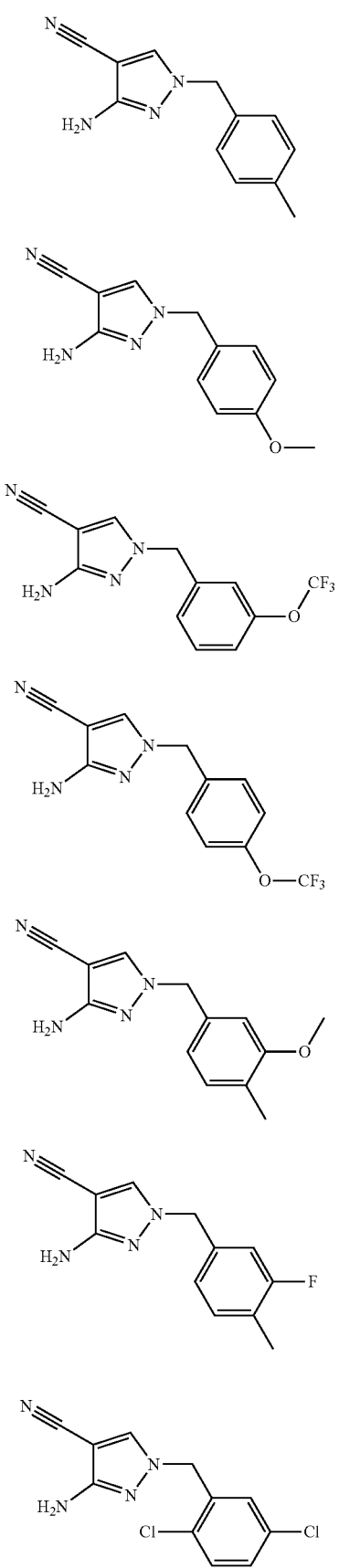
Intermediate 10
Intermediate 11
Intermediate 12
Intermediate 13
Intermediate 14
Intermediate 15
Intermediate 16
-continued
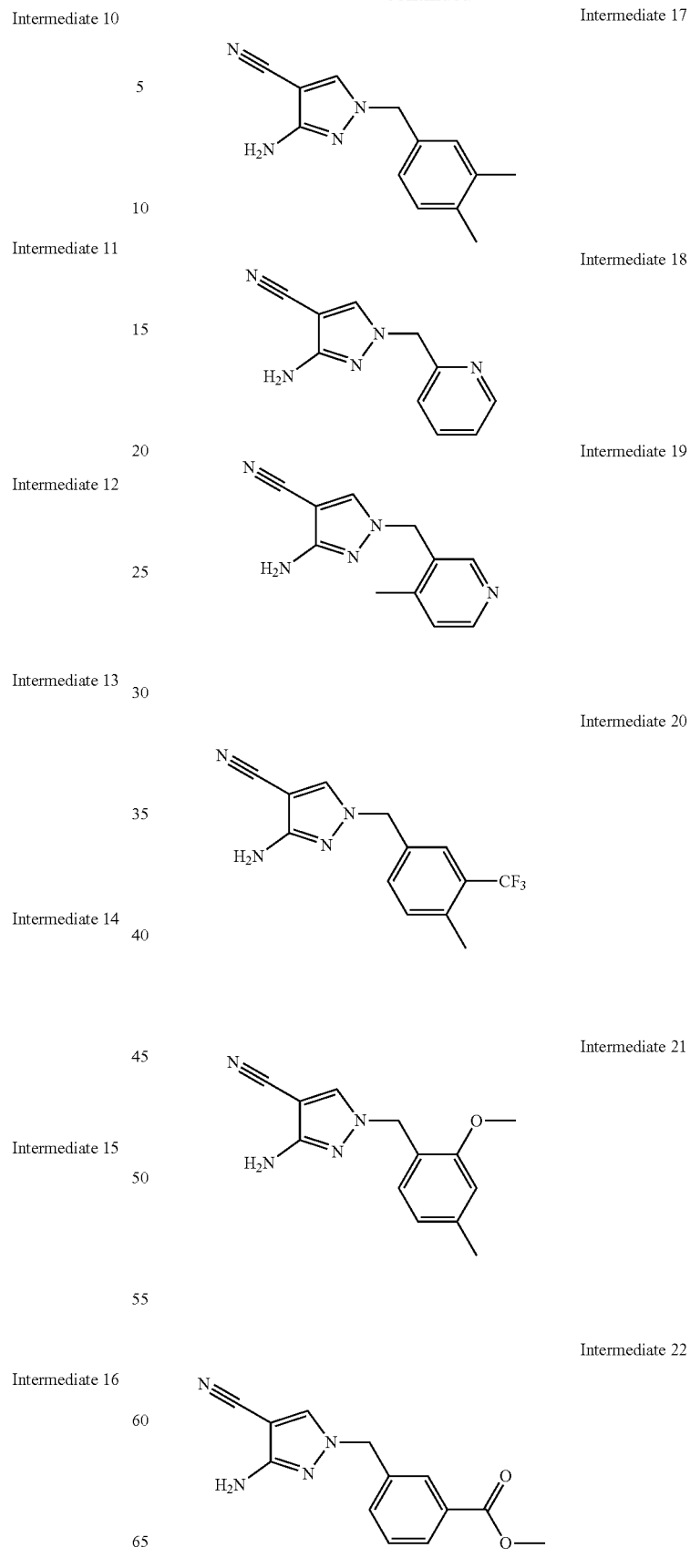
Intermediate 17
Intermediate 18
Intermediate 19
Intermediate 20
Intermediate 21
Intermediate 22

PREPARATION OF EXAMPLES 1-46

Example 1

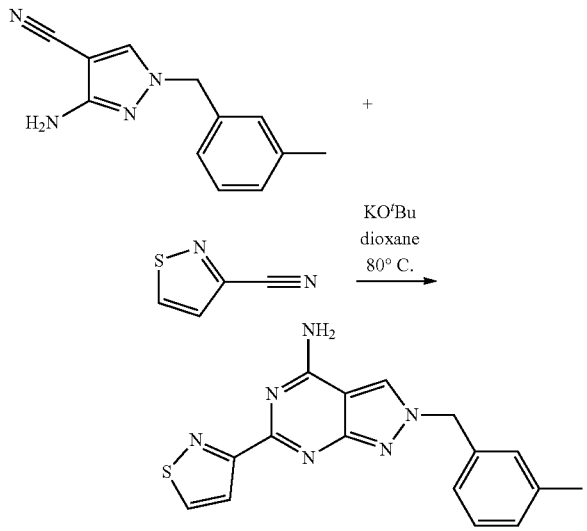

2-[(3-methylphenyl)methyl]-6-(1,2-thiazol-3-yl)-2H-pyrazolo[3,4-d]pyrimidin-4-amine To a reaction vial was added 3-amino-1-(m-tolylmethyl)pyrazole-4-carbonitrile (Intermediate 1, 2.6 g, 12.25 mmol) in 1,4-dioxane (78 mL) at room temperature followed by 1,2-thiazole-3-carbonitrile (1.75 g, 15.92 mmol) and potassium tert-butoxide (1.79 g, 15.92 mmol). The reaction vial was sealed, and the mixture was heated at 80° C. in an aluminum block, stirred at 80° C. for 5 h30 and then at room temperature overnight. The heterogeneous mixture was filtered and the solid was washed several times with EtOAc and water. The residue was dried under vacuum at 50° C. for 48 h and the resulting solid was purified by Flash Chromatography (Redisep column 220 g, Eluent: DCM/MeOH: 97/3) to afford a beige powder which was then triturated with MeOH and diethyl ether, dried under vacuum at 50° C. overnight to afford the title compound (2.01 g) as a beige powder (yield: 51%).

LCMS Method: [M+H]+ 323.1 observed at tr=1.13 min. $^1$H NMR (500 MHz, DMSO-d6): δ 9.07 (d, J=4.7 Hz, 1H), 8.38 (s, 1H), 8.00 (d, J=4.7 Hz, 1H), 7.79 (s, 2H), 7.28 (t, J=7.5 Hz, 1H), 7.20-7.13 (m, 3H), 5.55 (brs, 2H), 2.30 (s, 3H).

Example 2

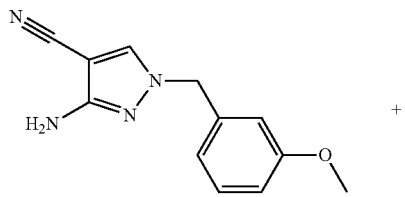

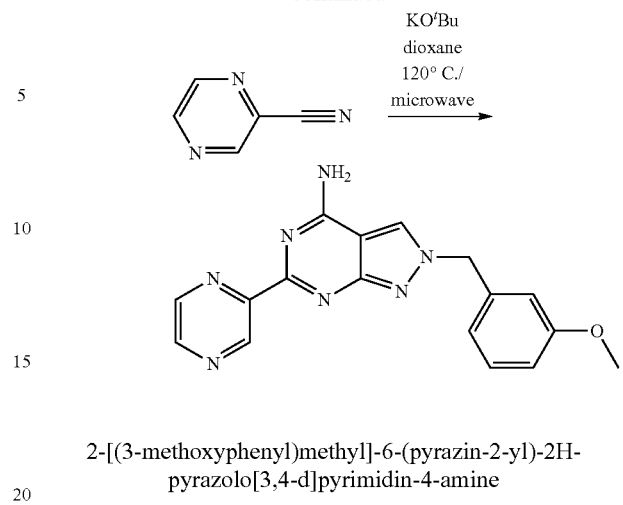

2-[(3-methoxyphenyl)methyl]-6-(pyrazin-2-yl)-2H-pyrazolo[3,4-d]pyrimidin-4-amine To a microwave reaction vial was added 3-amino-1-[(3-methoxyphenyl)methyl]pyrazole-4-carbonitrile (Intermediate 9, 250 mg, 1.09 mmol) in 1,4-dioxane (4.6 mL) at room temperature, followed by pyrazine-2-carbonitrile (0.13 mL, 1.42 mmol) and potassium tert-butoxide (135.2 mg, 1.20 mmol). The reaction vial was sealed, and the mixture was heated and stirred at 120° C. for h under microwave irradiation (CEM, 75 W). The reaction mixture was filtered, and the residue was washed with dioxane, EtOAc, and water. The brown precipitate was purified by Flash Chromatography (REDISEP column 24 g, eluent: DCM/MeOH: 100/0 to 90/10) to afford the title compound (340 mg) as a yellow solid (yield: 93%).

LCMS: [M+H]+ 334.2 observed at rt=0.89 min. $^1$H NMR (500 MHz, DMSO-d$_6$): δ 9.46 (d, J=1.0 Hz, 1H), 8.75-8.71 (m, 1H), 8.68 (d, J=2.5 Hz, 1H), 8.42 (s, 1H), 7.88 (brs, 2H), 7.31 (t, J=7.9 Hz, 1H), 6.97 (brs, 1H), 6.95-6.90 (m, 2H), 5.59 (s, 2H), 3.75 (s, 3H).

Example 3

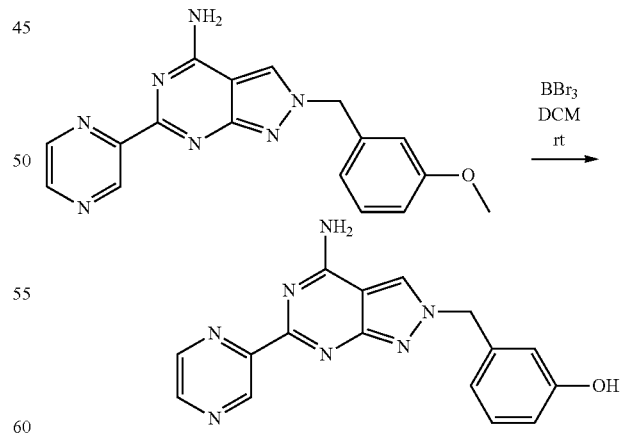

3-{[4-amino-6-(pyrazin-2-yl)-2H-pyrazolo[3,4-d]pyrimidin-2-yl]methyl}phenol

In a three necked round-bottom flask, under nitrogen, was added 2-[(3-methoxyphenyl)methyl]-6-pyrazin-2-yl-pyrazolo[3,4-d]pyrimidin-4-amine (Example 2,318 mg, 0.954 mmol) in DCM (10 mL) followed by the addition of tribromoborane (1M DCM) (2.86 mL, 2.86 mmol) at room temperature. The heterogeneous mixture is stirred at room temperature for 2 h and tribromoborane (1M DCM) (2.86 mL, 2.862 mmol) was added again. The reaction mixture was stirred at room temperature overnight. To the mixture was added saturated NaHCO$_3$ solution, EtOAc and few drops of THF. The layers were separated, and the aqueous layer was extracted with EtOAc three times. The combined organic layers were then washed with water, dried (Na$_2$SO$_4$), filtered and concentrated to dryness under vacuum. The residue was purified by Flash Chromatography (Neutral Alumina column 8 g, eluent: DCM/MeOH 100/0 to 90/10) to give the title compound (84 mg) as yellow powder (yield: 28%).

LCMS: [M+H]+ 320.1 observed at rt=0.66 min. $^1$H NMR (500 MHz, DMSO-d$_6$): δ 9.48 (s, 1H), 9.46 (d, J=1.3 Hz, 1H), 8.73 (t, J=2.2 Hz, 1H), 8.68 (d, J=2.5 Hz, 1H), 8.41 (s, 1H), 7.89 (s, 2H), 7.18 (t, J=7.7 Hz, 1H), 6.79 (d, J=7.6 Hz, 1H), 6.72 (d, J=8.6 Hz, 2H), 5.53 (s, 2H).

Example 46

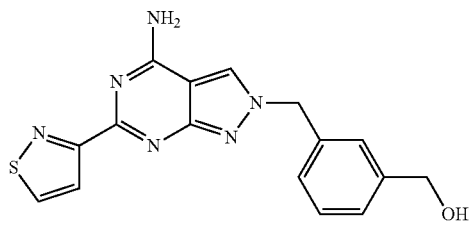 [SMILES: Nc1nc(-c2ccsn2)nc2nn(Cc3cccc(CO)c3)cc12]

[3-[(4-amino-6-(1,2-thiazol-3-yl)-pyrazolo[3,4-d] pyrimidin-2-yl)methyl]phenyl]methanol Step 1

Synthesis of methyl 3-[(4-amino-6-Isothiazol-3-yl-pyrazolo[3,4-d]pyrimidin-2-yl)methyl]benzoate In a sealed tube, under nitrogen, to a stirred solution of methyl 3-[(3-amino-4-cyano-pyrazol-1-yl)methyl]benzoate (Intermediate 22, 6.2 g, 24.19 mmol) in 4N hydrochloric acid solution in dioxane (120 mL) was added isothiazole-3-carbonitrile (0.01 mL, 31.45 mmol). The reaction mixture was stirred at 100° C. for 2 h. The reaction mixture was basified with a solution of 2N NaOH and DCM was then added. The suspension was filtered, washed with DCM (×2) to give the intermediate as a grey powder (7 g). The aqueous layer was extracted with DCM (×2). Combined organic layers were dried over Na$_2$SO$_4$, filtered and concentrated under reduced pressure to give the compound as a yellow powder. The crude was purified by flash chromatography (SiO$_2$, Biotage, Redisep 80 g) using a gradient of DCM/MeOH from 100/0 to 85/15 over 30 CV to give methyl 3-[(4-amino-6-isothiazol-3-yl-pyrazolo[3,4-d]pyrimidin-2-yl)methyl]benzoate as a white powder (860 mg, 10%).

LCMS: [M+H]+ 367.2 observed at rt=0.87 min. $^1$H NMR (400 MHz, DMSO-d$_6$) δ 9.08 (d, J=4.7 Hz, 1H), 8.47 (s, 1H), 8.03-7.95 (m, 2H), 7.94 (d, J=7.8 Hz, 1H), 7.85 (s, 2H), 7.67 (d, J=7.7 Hz, 1H), 7.56 (t, J=7.7 Hz, 1H), 5.71 (s, 2H), 3.85 (s, 3H).

Step 2

Synthesis of [3-[(4-amino-6-(1,2-thiazol-3-yl)-pyrazolo[3,4-d]pyrimidin-2-yl)methyl]phenyl]methanol In a round-bottomed flask, under nitrogen, to a stirred suspension of methyl 3-[(4-amino-6-(1,2-thiazol-3-yl)-pyrazolo[3,4-d]pyrimidin-2-yl)methyl]benzoate (1.36 g, 3.71 mmol) in THF-anhydrous (27 mL) at −5° C. was added 1 M lithium aluminum hydride in THF (5.56 mL, 5.56 mmol). The reaction mixture was stirred at −5° C. for 1 h. Then, 10 mL of EtOAc were added dropwise at −5° C. The mixture was diluted with in Et$_2$O (10 mL). The reaction mixture was quenched at −5° C. by addition of 0.078 mL of H$_2$O, 0.078 mL of of 15% NaOH and then 0.23 mL of H$_2$O. The suspension was filtered, washed with Et$_2$O (×2) and dried under vacuum at 50° C. overnight. The crude was purified by flash chromatography (SiO$_2$, Biotage, Redisep 24 g) using a gradient of DCM/MeOH from 97/3 to 80/20 over 20 CV to give the title compound as a yellow powder. The powder was triturated in Et$_2$O, filtered, washed with Et$_2$O, with DCM/THF and dried 48 h under vacuum at 50° C. to give [3-[(4-amino-6-(1,2-thiazol-3-yl)-pyrazolo[3,4-d]pyrimidin-2-yl)methyl]phenyl]methanol as a light orange powder (458 mg, 36%).

LCMS: [M+H]+ 339.2 observed at rt=0.69 min. $^1$H NMR (500 MHz, DMSO-d$_6$) δ 9.07 (d, J=4.7 Hz, 1H), 8.41 (s, 1H), 8.00 (d, J=4.7 Hz, 1H), 7.80 (s, 2H), 7.35 (d, J=7.6 Hz, 1H), 7.33 (s, 1H), 7.26 (dd, J=17.4, 7.6 Hz, 2H), 5.59 (s, 2H), 5.21 (t, J=5.7 Hz, 1H), 4.49 (d, J=5.7 Hz, 2H).

Examples 4-41 were prepared using similar general conditions to either Example 1 or 2 from the corresponding intermediates 1-21, as indicated in Table 1 below. Examples 42-45 were prepared using the same general method as Example 3 from the Example compounds indicated in Table 1 below.

TABLE 1

| Ex. No | Structure | General method | Starting material Intermediate or Ex. No | Yield | Characterisation |
|---|---|---|---|---|---|
| 4 | 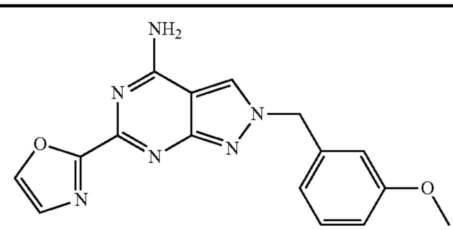 | 1B | Int. 9 | 22 mg (8%) | LCMS [M + H]+ 323.1 observed at rt = 1.13 min |

TABLE 1-continued

| Ex. No | Structure | General method | Starting material Intermediate or Ex. No | Yield | Characterisation |
|---|---|---|---|---|---|
| 5 | 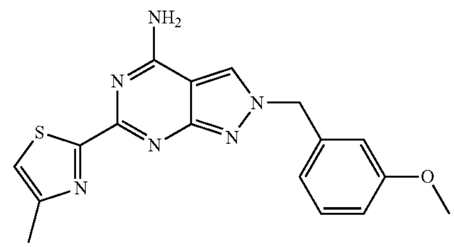 [SMILES: COc1cccc(Cn2cc3c(N)nc(-c4nc(C)cs4)nc3n2)c1] | 1B | Int. 9 | 99 mg (32%) | LCMS [M + H]+ 353.1 observed at rt = 1.29 min |
| 6 | 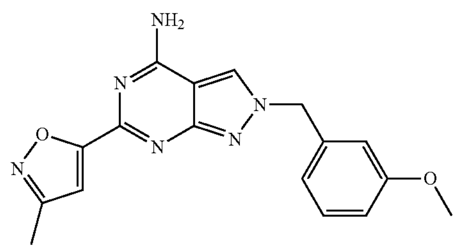 [SMILES: COc1cccc(Cn2cc3c(N)nc(-c4cc(C)no4)nc3n2)c1] | 1B | Int. 9 | 190 mg 64%) | LCMS [M + H]+ 337.1 observed at rt = 1.30 min |
| 7 | 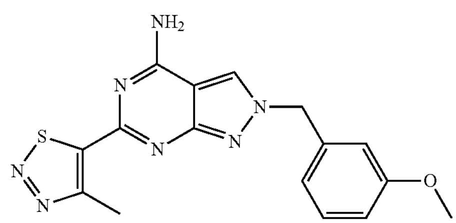 [SMILES: COc1cccc(Cn2cc3c(N)nc(-c4snnc4C)nc3n2)c1] | 1A | Int. 9 | 20 mg (20%) | LCMS [M + H]+ 354.1 observed at rt = 1,58 min |
| 8 | 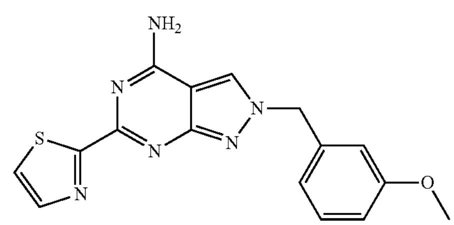 | 1B | Int. 9 | 133 mg (45%) | LCMS [M + H]+ 339.1 observed at rt = 1.16 min |
| 9 | 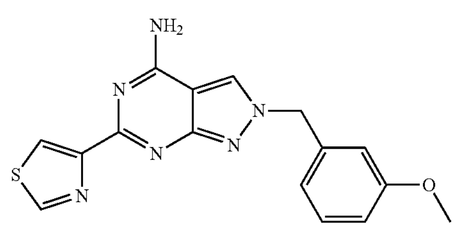 [SMILES: COc1cccc(Cn2cc3c(N)nc(-c4cscn4)nc3n2)c1] | 1B | Int. 9 | 17 mg (6%) | LCMS [M + H]+ 339.1 observed at rt = 0.86 min, |
| 10 | 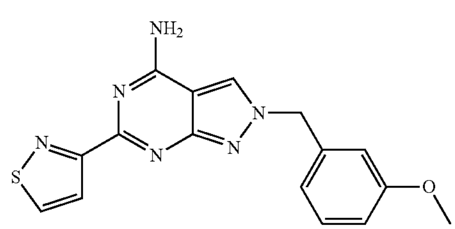 [SMILES: COc1cccc(Cn2cc3c(N)nc(-c4ccsn4)nc3n2)c1] | 1B | Int. 9 | 70 mg (19%) | LCMS [M + H]+ 339.1 observed at rt = 0.96 min |

TABLE 1-continued

| Ex. No | Structure | General method | Starting material Intermediate or Ex. No | Yield | Characterisation |
|---|---|---|---|---|---|
| 11 | 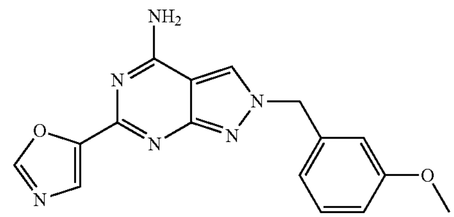 [SMILES: COc1cccc(Cn2cc3c(N)nc(-c4cnco4)nc3n2)c1] | 1B | Int. 9 | 14 mg (4%) | LCMS [M + H]+ 323.1 observed at rt = 1.05 min |
| 12 | 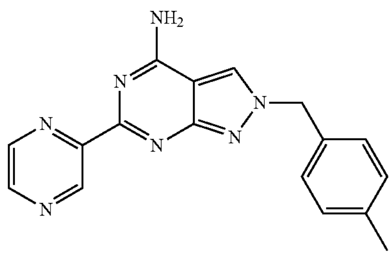 [SMILES: Cc1ccc(Cn2cc3c(N)nc(-c4cnccn4)nc3n2)cc1] | 1B | Int. 10 | 166 mg (37%) | LCMS [M + H]+ 318.1 observed at rt = 1.00 min |
| 13 | 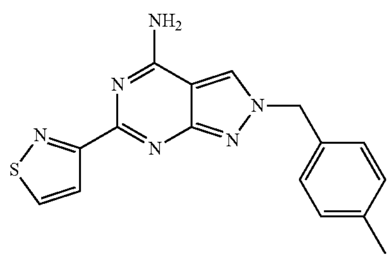 [SMILES: Cc1ccc(Cn2cc3c(N)nc(-c4ccsn4)nc3n2)cc1] | 1B | Int. 10 | 340 mg (75%) | LCMS [M + H]+ 323.1 observed at rt = 1.08 min |
| 14 | 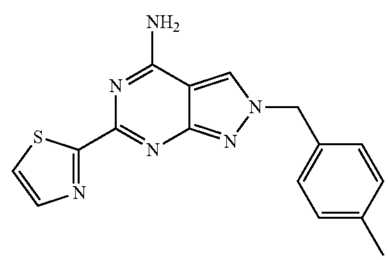 [SMILES: Cc1ccc(Cn2cc3c(N)nc(-c4nccs4)nc3n2)cc1] | 1A | Int. 10 | 31 mg (22%) | LCMS [M + H]+ 323.1 observed at rt = 1.30 min |
| 15 | 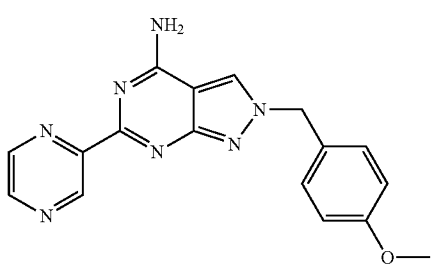 [SMILES: COc1ccc(Cn2cc3c(N)nc(-c4cnccn4)nc3n2)cc1] | 1B | Int. 11 | 55 mg (15%) | LCMS [M + H]+ 334.2 observed at rt = 0.87 min |
| 16 | 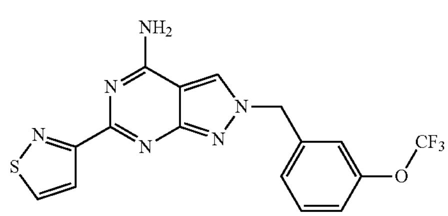 [SMILES: Nc1nc(-c2ccsn2)nc2nn(Cc3cccc(OC(F)(F)F)c3)cc12] | 1B | Int. 12 | 105 mg (34%) | LCMS [M + H]+ 393.0 observed at rt = 1.33 min, |

TABLE 1-continued

| Ex. No | Structure | General method | Starting material Intermediate or Ex. No | Yield | Characterisation |
|---|---|---|---|---|---|
| 17 | 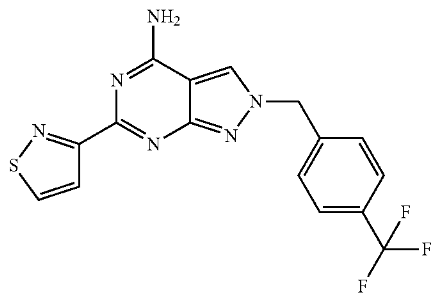 [SMILES: Nc1nc(-c2ccsn2)nc2nn(Cc3ccc(C(F)(F)F)cc3)cc12] | 1B | Int. 13 | 75 mg (27%) | LCMS [M + H]+ 377.1 observed at rt = 1.29 min |
| 18 | 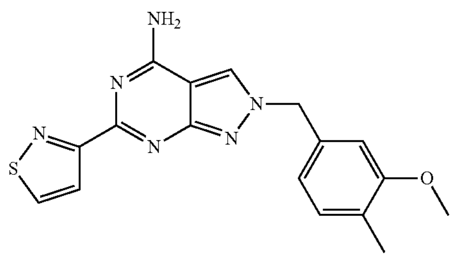 [SMILES: COc1cc(Cn2cc3c(N)nc(-c4ccsn4)nc3n2)ccc1C] | 1B | Int. 14 | 90 mg (15%) | LCMS [M + H]+ 353.1 observed at rt = 1.18 min |
| 19 | 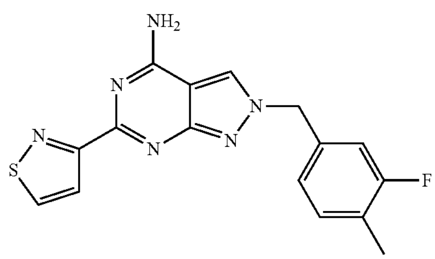 [SMILES: Cc1ccc(Cn2cc3c(N)nc(-c4ccsn4)nc3n2)cc1F] | 1B | Int. 15 | 50 mg (14%) | LCMS [M + H]+ 341.1 observed at rt = 1.15 min |
| 20 | 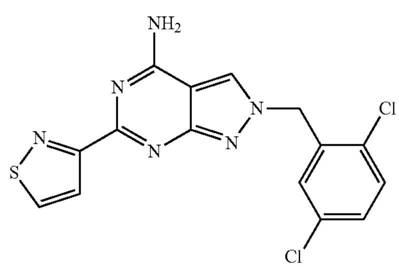 [SMILES: Nc1nc(-c2ccsn2)nc2nn(Cc3cc(Cl)ccc3Cl)cc12] | 1B | Int. 16 | 67 mg (19%) | LCMS [M + H]+ 377.0 observed at rt = 1.57 min, |
| 21 | 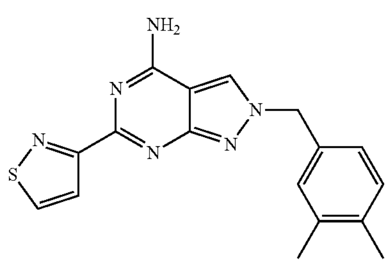 [SMILES: Cc1ccc(Cn2cc3c(N)nc(-c4ccsn4)nc3n2)cc1C] | 1B | Int. 17 | 105 mg (24%) | LCMS [M + H]+ 337.2 observed at rt = 1.52 min |
| 22 | 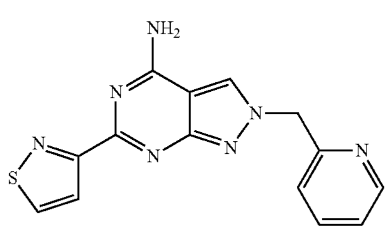 [SMILES: Nc1nc(-c2ccsn2)nc2nn(Cc3ccccn3)cc12] | 1B | Int. 18 | 17 mg (4%) | LCMS [M + H]+ 310.1 observed at rt = 0.88 min |

TABLE 1-continued

| Ex. No | Structure | General method | Starting material Intermediate or Ex. No | Yield | Characterisation |
|---|---|---|---|---|---|
| 23 | 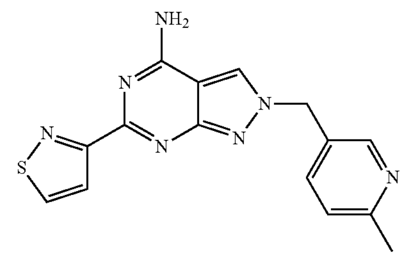 [SMILES: Cc1ccc(Cn2cc3c(N)nc(-c4ccsn4)nc3n2)cn1] | 1B | Int. 19 | 103 mg (27%) | LCMS [M + H]+ 324.1 observed at rt = 0.43 min |
| 24 | 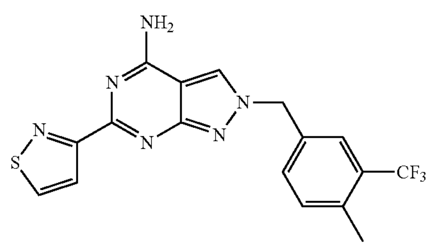 [SMILES: Cc1ccc(Cn2cc3c(N)nc(-c4ccsn4)nc3n2)cc1C(F)(F)F] | 1B | Int. 20 | 160 mg (46%) | LCMS [M + H]+ 391.2 observed at rt = 1.72 min |
| 25 | 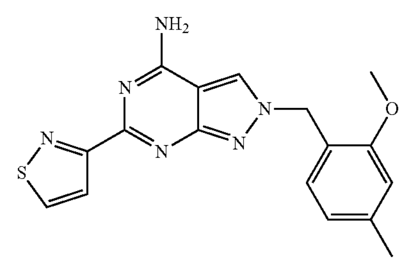 [SMILES: COc1cc(C)ccc1Cn1cc2c(N)nc(-c3ccsn3)nc2n1] | 1B | Int. 21 | 75 mg (13%) | LCMS [M + H]+ 353.3 observed at rt = 1.45 min |
| 26 | 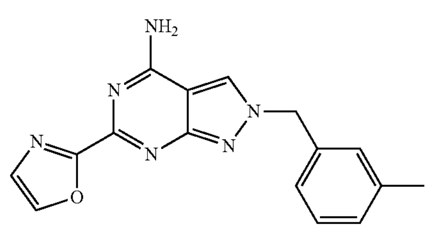 [SMILES: Cc1cccc(Cn2cc3c(N)nc(-c4ncco4)nc3n2)c1] | 1A | Int. 1 | 60 mg (23%) | LCMS [M + H]+ 307.0 observed at rt = 1.17 min |
| 27 | 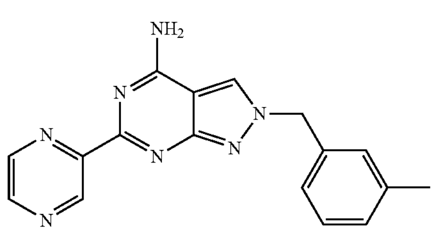 [SMILES: Cc1cccc(Cn2cc3c(N)nc(-c4cnccn4)nc3n2)c1] | 1B | Int. 1 | 117 mg (15%) | LCMS [M + H]+ 318.2 observed at rt = 1.29 min |
| 28 | 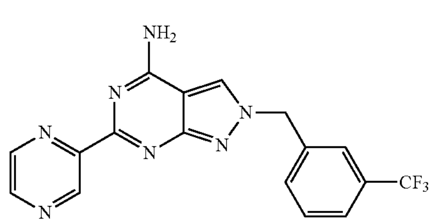 [SMILES: Nc1nc(-c2cnccn2)nc2nn(Cc3cccc(C(F)(F)F)c3)cc12] | 1A | Int. 2 | 173 mg (49%) | LCMS [M + H]+ 372.0 observed at rt = 1.17 min |

TABLE 1-continued

| Ex. No | Structure | General method | Starting material Intermediate or Ex. No | Yield | Characterisation |
|---|---|---|---|---|---|
| 29 | 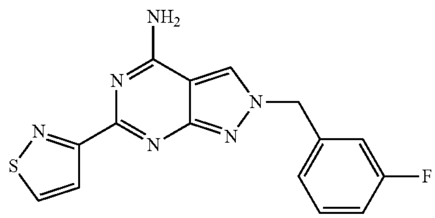 [SMILES: Nc1nc(-c2ccsn2)nc2nn(Cc3cccc(F)c3)cc12] | 1B | Int. 3 | 192 mg (51%) | LCMS [M + H]+ 327.2 observed at rt = 1.26 min |
| 30 | 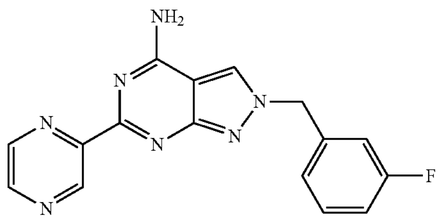 [SMILES: Nc1nc(-c2cnccn2)nc2nn(Cc3cccc(F)c3)cc12] | 1A | Int. 3 | 12 mg (3%) | LCMS [M + H]+ 322.0 observed at rt = 0.88 min |
| 31 | 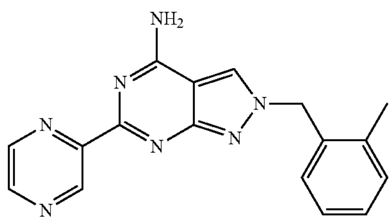 [SMILES: Cc1ccccc1Cn1cc2c(N)nc(-c3cnccn3)nc2n1] | 1A | Int. 4 | 46 mg (6%) | LCMS [M + H]+ 318.1 observed at rt = 0.96 min |
| 32 | 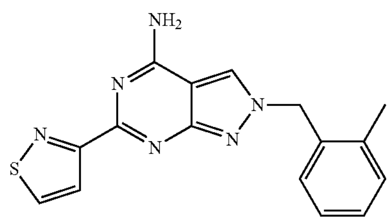 [SMILES: Cc1ccccc1Cn1cc2c(N)nc(-c3ccsn3)nc2n1] | 1A | Int. 4 | 78 mg (10%) | LCMS [M + H]+ 323.0 observed at rt = 1.04 min |
| 33 | 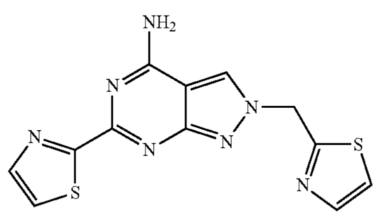 [SMILES: Nc1nc(-c2nccs2)nc2nn(Cc3nccs3)cc12] | 1B | Int. 5 | 5 mg (2%) | LCMS [M + H]+ 316.0 observed at rt = 0.79 min |
| 34 | 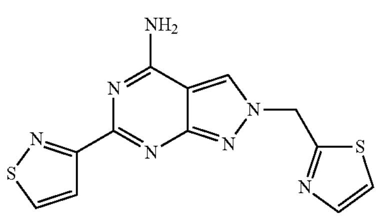 [SMILES: Nc1nc(-c2ccsn2)nc2nn(Cc3nccs3)cc12] | 1A | Int. 5 | 57 mg (15%) | LCMS [M + H]+ 315.9 observed at rt = 0.61 min |
| 35 | 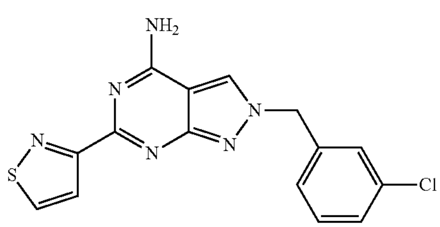 [SMILES: Nc1nc(-c2ccsn2)nc2nn(Cc3cccc(Cl)c3)cc12] | 1A | Int. 6 | 100 mg (45%) | LCMS [M + H]+ 343.0 observed at rt = 1.13 min |

TABLE 1-continued

| Ex. No | Structure | General method | Starting material Intermediate or Ex. No | Yield | Characterisation |
|---|---|---|---|---|---|
| 36 | 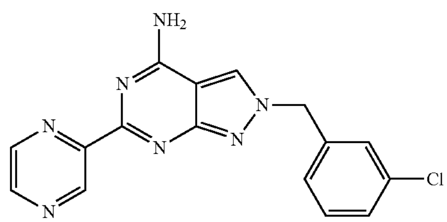 [SMILES: Nc1nc(-c2cnccn2)nc2nn(Cc3cccc(Cl)c3)cc12] | 1A | Int. 6 | 214 mg (54%) | LCMS [M + H]+ 338.0 observed at rt = 1.04 min |
| 37 | 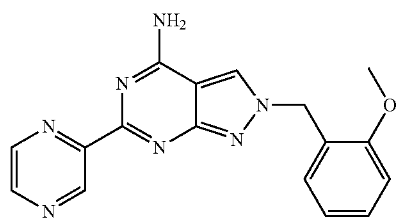 [SMILES: COc1ccccc1Cn1cc2c(N)nc(-c3cnccn3)nc2n1] | 1A | Int. 7 | 65 mg (20%) | LCMS [M + H]+ 334.1 observed at rt = 0.90 min |
| 38 | 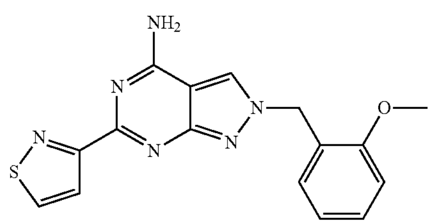 [SMILES: COc1ccccc1Cn1cc2c(N)nc(-c3ccsn3)nc2n1] | 1B | Int. 7 | 104 mg (28%) | LCMS [M + H]+ 339.1 observed at rt = 0.99 min |
| 39 | 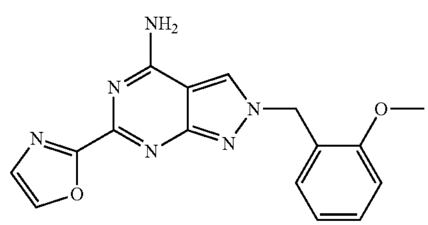 [SMILES: COc1ccccc1Cn1cc2c(N)nc(-c3ncco3)nc2n1] | 1A | Int. 7 | 16 mg (5%) | LCMS [M + H]+ 323.1 observed at rt = 1.09 min |
| 40 | 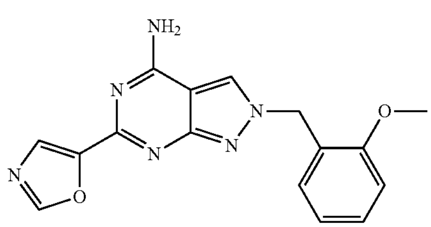 [SMILES: COc1ccccc1Cn1cc2c(N)nc(-c3cnco3)nc2n1] | 1A | Int. 7 | 15 mg (5%) | LCMS [M + H]+ 323.0 observed at rt = 1.10 min |
| 41 | 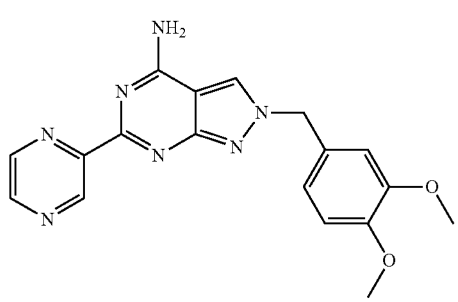 [SMILES: COc1ccc(Cn2cc3c(N)nc(-c4cnccn4)nc3n2)cc1OC] | 1B | Int. 8 | 360 mg (43%) | LCMS [M + H]+ 364.2 observed at rt = 0.79 min |

TABLE 1-continued

| Ex. No | Structure | General method | Starting material Intermediate or Ex. No | Yield | Characterisation |
|---|---|---|---|---|---|
| 42 | (structure: 4-amino-6-(isothiazol-3-yl)-2-(3-hydroxybenzyl)-2H-pyrazolo[3,4-d]pyrimidine) | 2 | Example 12 | 15 mg (16%) | LCMS [M + H]+ 325.1 observed at rt = 0.71 min |
| 43 | (structure: 4-amino-6-(isothiazol-3-yl)-2-(2-hydroxy-5-methylbenzyl)-2H-pyrazolo[3,4-d]pyrimidine) | 2 | Example 23 | 7 mg (11%) | LCMS [M + H]+ 339.1 observed at rt = 0.95 min |
| 44 | (structure: 4-amino-6-(isothiazol-3-yl)-2-(2-hydroxybenzyl)-2H-pyrazolo[3,4-d]pyrimidine) | 2 | Example 37 | 17 mg (18%) | LCMS [M + H]+ 325.1 observed at rt = 1.09 min |
| 45 | (structure: 4-amino-6-(isothiazol-3-yl)-2-(2-methyl-5-hydroxybenzyl)-2H-pyrazolo[3,4-d]pyrimidine) | 2 | Example 16 | 17 mg (24%) | LCMS [M + H]+ 339.2 observed at rt = 1.19 min |

Large Scale Preparation of Example 1

Step 1

Synthesis of 3-amino-1-(3-methylphenylmethyl) pyrazole-4-carbonitrile

In a 20 L jacketed laboratory reactor under nitrogen, 3-amino-1H-pyrazole-4-carbonitrile (0.825 kg, 1.28 eq) was dissolved in acetone (5.5 L, 5 vol) and $K_3PO_4$ (1.595 kg, 1.26 eq) was added. The suspension was stirred and temperature jack set to −10° C. 1-(bromomethyl)-3-methylbenzene (1.1 kg, 1 eq) dissolved in acetone (2.75 L, 2.5 vol) was added dropwise in 1 h. The temperature jack was set to 0° C. and reaction mixture stirred for 14 h.

The temperature jack was reset to 50° C. and mixture concentrated under vacuum to final 2 vol. The temperature jack was set to 20° C., EtOAc (4.5 vol) and water (2.5 vol) were added and after stirring for 20 min the layers were allowed to settle and aqueous layer was discarded). Water (1.5 vol) was added and after stirring for 20 min layers were separated.

The temperature jack was set to 55° C. and the organic layer was reduced by distillation under vacuum until 2 vol. EtOH (4 vol) was added and the mixture was concentrated to 2 vol under vacuum. The addition of EtOH and concentration was repeated three times. On the final repeat, the reaction mixture was refluxed for 1 hour to obtain complete dissolution. The mixture was cooled to 0° C. over 240 min. The step 1 intermediate precipitation started when the internal temperature was 50° C. Slurry was left stirring at 0° C. for 8 h.

The slurry was filtered on a P3 synthered funnel. Reaction vessel and cake were washed with 3 vol of heptane. The solid was dried under vacuum at 50° C. for 24 h to give 0.76 kg (60%) of white solid 3-amino-1-(3-methylphenylmethyl) pyrazole-4-carbonitrile.

Step 2

Synthesis of 2-[(3-methylphenyl)methyl]-6-(1,2-thiazol-3-yl)-2H-pyrazoo[3,4-d]pyrimidin-4-amine (Example 1)

In a 0.5 L jacketed lab reactor under nitrogen atmosphere, KO$^t$Bu 1M in THF (1.2 eq, 5.7 vol) was charged and diluted with dry THF (6 vol). The temperature jack was set to 65° C. and the solution stirred. A solution of 3-amino-1-(3-methylphenylmethyl)pyrazole-4-carbonitrile (Step 1, 15 g, 1 eq) and 1,2-thiazole-3-carbonitrile (7.8 g, 1.06 eq) was prepared by dissolving the materials in dry THF (8 vol), and was added dropwise to KO$^t$Bu over 1 h, keeping the solution at 60° C. The solution turned into a light brown slurry.

At the end of addition, the temperature jack was set to 75° C., and reaction mixture allowed to reflux. The reaction mixture was stirred for 3 h at reflux. The temperature jack was set to 50° C. and water (5 vol) was added. The slurry became a biphasic solution which was stirred for 20 min and then allowed to separate for 20 min without stirring. Neat separation was obtained. Water phase (bottom layer) was discarded (around 2-2.5 vol).

The temperature jack was set to 80° C. and the reaction volumes were concentrated to 7 vol. The temperature jack was set to 60° C. and water (3 vol) was added. The solid was filtered on a P3 sintered funnel with vacuum and cake washed 1 time with 2 vol of THF/water solution 30/70, then washed 3 times with 3 vol of water. The solid was dried under vacuum at 50° C. for 24 h to give 15.2 g (67%) of beige solid 2-[(3-methylphenyl)methyl]-6-(1,2-thiazol-3-yl)-2H-pyrazolo[3,4-d]pyrimidin-4-amine (Example 1).

HPLC: Purity was assessed at 99.3% by hplc using a system equipped with a Xbridge RP 3.5 μm (10×3 cm) column at a temperature of 40° C., using a gradient elution of methanol in water containing 10 mM ammonium formate (5-95% over 30 min). $^1$H NMR (600 MHz, DMSO-d6): δ 9.07 (d, J=4.8 Hz, 1H), 8.39 (s, 1H), 8.00 (d, J=4.8 Hz, 1H), 7.81 (br. s, 2H), 7.27 (m, 1H), 7.18 (s, 1H), 7.16 (d, J=7.4 Hz, 2H), 5.55 (brs, 2H), 2.30 (s, 3H).

In Vitro Testing

Affinity for the human adenosine receptor sub-types (A2a, A2b, A1 and A3) was determined by surface plasmon resonance (SPR) using published methodologies (see below for further details). The results are shown in Table 2, below.

Functional activity was measured by inhibition of cAMP release in HEK cells (see below for further details). The results are also shown in Table 2, below.

Functional activity of a literature compound, Comparative Example 1, was also measured. Comparative Example 1 is compound 25 of Squarcialupi, L et al, Bioorganic and Medicinal Chemistry 24 2016 24 2794-2808). The results are also shown in Table 2 below. Comparative Example 1 has the following structure:

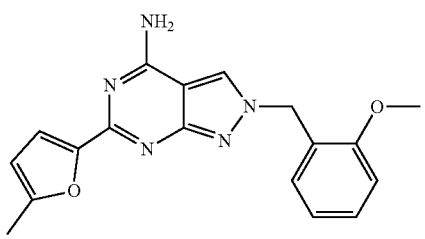

SPR Protocol

Affinity for the human adenosine receptor sub-types (A2a, A2b, A1 and A3) was determined by SPR as described in Aristotelous, T., et al, Methods in Enzymology (2015), Volume 556, Chapter 23, pages 499-525 and Congreve, M., et al, J Med Chem (2012), Vol. 55, pages 1898-1903. The method used was analogous to the method used in Congreve, M., et al (see supplementary page S10) for the A2a receptor, but the wild type receptor was used rather than the proprietary StaR form.

cAMP Protocol

To screen A2a receptor inhibitors by HTRF technology, about 500 HEK-A2aR cells (HEK 293 transfected with human A2a receptors) were treated with inhibitors in presence of stimulation buffer (1×HBSS, 5 mM HEPES, 0.1% BSA stabilizer, pH 7.4) supplemented with 30 μM phosphodiesterase inhibitor Rolipram (to prevent cAMP degradation). This stimulation was immediately followed by treatment with 3 nM standard A2aR agonist (NECA) for 10 min under gentle shaking at room temperature. After that, inhibition of cAMP release was determined directly using LANCE Ultra cAMP assay (Perkin Elmer TRF0263). The results are shown in Table 2, below.

All analysis was performed using GraphPad Prism 7.0 (GraphPad Software, San Diego, USA). Results are given, as $EC_{50}$ (M).

Results

TABLE 2

| Example Number | A2a SPR $IC_{50}$ (μM) | A2a cAMP $EC_{50}$ (μM) | A2b SPR $IC_{50}$ (μM) | A1 SPR $IC_{50}$ (μM) | A3 SPR $IC_{50}$ (μM) |
|---|---|---|---|---|---|
| Comparative Example 1 | 0.0022 | 0.018 | 4.91 | 0.114 | 1.97 |
| 1 | 0.0035 | 0.004 | 1.5 | 3.1 | 35.8 |
| 2 | 0.0067 | 1.53 | | | |
| 3 | 0.041 | | | | |
| 4 | 0.0049 | 0.40 | | | |
| 5 | 0.047 | | | | |
| 6 | 0.162 | | | | |
| 7 | 0.024 | | | | |
| 8 | 0.011 | 0.023 | | | |
| 9 | 0.041 | 0.875 | | | |
| 10 | 0.0051 | 0.235 | 0.69 | 0.68 | 60 |
| 11 | 0.0049 | 0.070 | 0.58 | 0.35 | 21.0 |
| 12 | 0.0079 | 0.199 | 9.0 | 7.3 | 38.8 |
| 13 | 0.015 | 0.128 | | | |
| 14 | 0.014 | 0.054 | | | |
| 15 | 0.253 | | | | |
| 16 | 0.0083 | 0.009 | | | |
| 17 | 0.054 | 0.226 | | | |
| 18 | 0.018 | 0.218 | | | |
| 19 | 0.0056 | 0.084 | 1.45 | 1.18 | Non-binder |
| 20 | 0.013 | 0.145 | | | |
| 21 | 0.0050 | 0.004 | | | |
| 22 | 0.027 | | | | |
| 23 | 0.029 | | | | |
| 24 | 0.0079 | 0.011 | 25.56 | 1.42 | 49.9 |
| 25 | 0.018 | 0.407 | | | |
| 26 | 0.0028 | 0.123 | | | |
| 27 | 0.0032 | 0.007 | | | |
| 28 | 0.0032 | 0.013 | | | |
| 29 | 0.015 | 0.118 | | | |
| 30 | 0.0080 | 0.232 | | | |
| 31 | 0.0057 | 0.056 | | | |
| 32 | 0.010 | 0.014 | | | |
| 33 | 0.027 | 2.16 | | | |
| 34 | 0.067 | | | | |
| 35 | 0.0042 | 0.060 | 0.53 | 0.29 | 4.7 |
| 36 | 0.0015 | 0.030 | | | |
| 37 | 0.0027 | 0.082 | | | |
| 38 | 0.0043 | 0.013 | 11.7 | 3.4 | 44.3 |
| 39 | 0.0043 | 0.213 | | | |
| 40 | 0.0020 | 0.013 | 1.46 | 0.99 | 46.2 |
| 41 | 0.589 | | | | |
| 42 | 0.061 | | | | |
| 43 | 0.013 | | | | |
| 44 | 0.015 | 0.127 | | | |
| 45 | 0.031 | | | | |
| 46 | 0.037 | | >100 | >100 | >100 |

Preferred compounds of the invention are those with SPR $IC_{50}$ values below 1 μM for the A2a receptor. Even more preferred compounds are those with SPR $IC_{50}$ values below 0.1 μM for the A2a receptor. Even more preferred compounds are those with SPR $IC_{50}$ values below 0.1 μM for the A2a receptor.

Preferred compounds of the invention are those with cAMP $EC_{50}$ values below 3 μM for the A2a receptor. More preferred compounds are those with cAMP $EC_{50}$ values below 1 lM for the A2a receptor. Even more preferred compounds are those with cAMP $EC_{50}$ values below 0.1 µM for the A2a receptor.

For compounds of the invention in which the SPR $IC_{50}$ values were measured for A2b, A1 and/or A3 receptors, and for Comparative Example 1, relative selectivity was calculated for the A2a receptor compared to the A2b, A1 and/or A3 receptors. The results are shown in Table 3, below (values have been rounded to 2 significant figures).

TABLE 3

| Example Number | Relative selectivity for A2a v. A2b | Relative selectivity for A2a v. A1 | Relative selectivity for A2a v. A3 |
|---|---|---|---|
| Comparative Example 1 | 2200 | 51 | 900 |
| 1 | 430 | 890 | 10000 |
| 10 | 140 | 130 | 12000 |
| 11 | 120 | 71 | 4300 |
| 12 | 1100 | 920 | 4900 |
| 19 | 260 | 210 | >10000 |
| 24 | 3200 | 180 | 6300 |
| 35 | 130 | 69 | 1100 |
| 38 | 2700 | 790 | 10000 |
| 40 | 730 | 500 | 23000 |
| 46 | >2700 | >2700 | >2700 |

Solubility
Solubility Protocol

The test compound in solid form was suspended in water (or specific buffer). After overnight stirring at ambient temperature protected from light, suspensions were filtered. An aliquot of the resulting supernatant was quantified using LC-UV method against a reference solution in DMSO obtained by preparation from powder.

Solubility Results

The solubility of Comparative Example 1 was measured as 0.001 mg/mL. The solubility of certain compounds of the invention were measured. Example compounds 1 to 4, 8 to 15, 17, 19, 22, 23, 25 to 27, 29 to 31, 34 to 37, and 39 to 48 were at least 5 times more soluble than Comparative Example 1 (i.e. those compounds had a solubility of greater than 0.005 mg/mL). Compounds 2, 3, 8, 11, 12, 13, 17, 22, 23, 25 to 27, 29 to 31, 34, 35, 37, and 39 to 44 were at least 10 times more soluble than Comparative Example 1 (i.e. those compounds had a solubility of greater than 0.010 mg/mL). Compounds 2, 3, 8, 11, 12, 13, 17, 22, 23, 25 to 27, 29, 30, 34, and 39 to 44 were at least 20 times more soluble than Comparative Example 1 (i.e. those compounds had a solubility of greater than 0.020 mg/mL). Compounds 2, 3, 12, 13, 17, 22, 23, 27, 29, 30, 34, 41 and 44 were at least 50 times more soluble than Comparative Example 1 (i.e. those compounds had a solubility of greater than 0.050 mg/mL). Compounds 13, 22, 23 and 34 were at least 100 times more soluble than Comparative Example 1 (i.e. those compounds had a solubility of greater than 0.100 mg/mL).

Compound Induced Recovery of 2-Chloroadenosine (CADO) Mediated Inhibition of IL-2 Production on Human Primary CD3+ T-Cells Protocol $CD3^+$ cells were isolated from Buffy Coat of two human healthy donors (Donor 1: D1 and Donor 2: D2) with the RosetteSep technology (RosetteSep Human T cell enrichment cocktail from Stem Cell) according to provider's instructions. T-cells were then stimulated with anti-CD3 mAb, anti-CD28 mAb coated beads (Dynabeads® Human T-Activator CD3/CD28 (Thermo Fisher Scientific) in a complete medium containing 10% fetal bovine serum in the presence or not of Example 1. After one hour incubation time, CADO (2-chloroadenosine, Abcam Biochemical) at 10 µM was added to the culture. After 48 hours of stimulation at 37° C., 5% $CO_2$ and a short centrifugation, culture supernatant were harvested and stored at −80° C. for further evaluation by ELISA. In the meantime, a staining with a living dye was performed to access compound-induced toxicity. Il-2 measurement was performed by using the Human IL-2 Uncoated ELISA (Invitrogen) following data sheet instructions. To access the percentage of IL-2 inhibition induced by 10 µM CADO, the calculation used control condition (cells stimulated in basal condition). Then to access compound-induced recovery of IL-2 production, each dose was normalized following this formula: ([sample]−[mean of CADO])/([mean of basal condition]−[mean of CADO])*100. Compounds normalization was performed per plate. To access T-cell viability and compound cytotoxicity, cells were centrifuged, washed and then stained with the Fixable Viability Dye. Data acquisition was performed by flow cytometry on a FACS Fortessa X20 and data analysis using DIVA Software. To access compounds cytotoxicity on different donors, data were normalized according to cell viability of cells stimulated in the presence of CADO without compound.

Results

The results of this experiment are shown in FIG. 1. As can be seen from FIG. 1, Example 1 induced a recovery of CADO mediated inhibition of IL-2 production on human primary CD3+ T-cells with an $EC_{50}$ of 560 nM+/−120.

In Vivo Testing
Compound Induced Inhibition of the Growth of MCA-205 Tumor

Protocol

C57/BI6JRjJL female mice (9-10 weeks old from Janvier Laboratories) were engrafted in subcutaneous location with $0.25.10^6$ MCA-205 cells (suspended in 100% PBS buffer, fibrosarcoma cell line kindly provided by Dr. J. Stagg, Universite de Montréal, Canada). Mice were then kept in a post-operative cabinet at 28° C. until complete recovery.

Randomization of mice was performed on day 9 post-cell inoculation, after measurement of tumour volumes using a digital caliper. Assuming an ovoid form of the tumour, the following formula was applied: Volume=0.52×(width)²× length. Width and length were expressed in mm, volume in $mm^3$. Twenty-six female mice were allocated in two groups: vehicle and Example 1 (n=13 mice/group). Oral gavage with vehicle (control group, PEG200/Soluplus 10% in Citrate Buffer pH3 at 50 mM (50%/50% w/v)) or Example 1 solubilized in the vehicle at 30 mg/kg in BID (twice daily administrations by oral gavage with a volume of administration of 5 ml/kg) was initiated 10 days after cell inoculation and continued for 11 consecutive days.

Results

Figure 2:
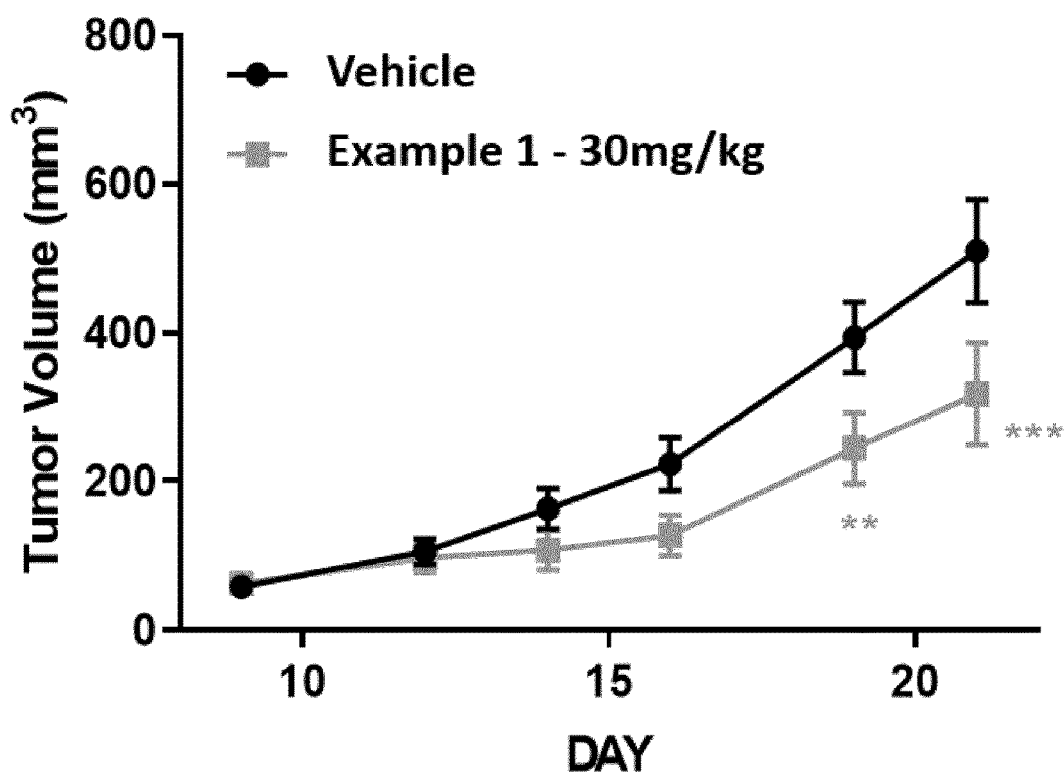
FIG. 2 shows the average tumor volume (mm$^3$±SEM) in syngeneic C57Bl6J mice engrafted with MCA-205 mouse cancer cells on day 0 and treated with vehicle (control group, n=13) or Example 1 at 30 mg/kg in BID (twice daily administrations) on day 10 and for 11 consecutive days (n=13).  indicates p<0.005 and * indicates p<0.001.

The results of this experiment are shown in FIG. 2. As can be seen from FIG. 2, a significant inhibition of the mean tumor volume (mean $mm^3$±SEM) was observed from day 19 to study termination in response to Example 1 (p<0.005 and *p<0.001, 2-way Anova with repeated measures statistical analysis, Dunnett's multiple comparison test).

The following clauses define various aspects of the present:

§ 1. A compound of formula (I), or pharmaceutically acceptable ester, amide, carbamate, solvate or salt thereof, including a salt of such an ester, amide or carbamate,

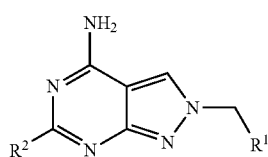

wherein $R^1$ is an optionally substituted phenyl, or an optionally substituted 5- or 6-membered aromatic heterocycle comprising 1, 2 or 3 heteroatoms independently selected from the group consisting of N, S and O, wherein said phenyl is optionally substituted with 1, 2 or 3 substituents, each substituent being independently selected from the group consisting of halogen, OH, $C_{1-8}$alkyl, $C_{1-8}$alkyl substituted with 1, 2 or 3 halogens or OH groups, $OC_{1-8}$alkyl, and $OC_{1-4}$alkyl substituted with 1, 2 or 3 halogens or OH groups, and wherein said 5- or 6-membered aromatic heterocycle is optionally substituted with 1, 2 or 3 substituents, each substituent being independently selected from the group consisting of halogen, OH, $C_{1-8}$alkyl, $C_{1-8}$alkyl substituted with 1, 2 or 3 halogens or OH groups, $OC_{1-8}$-alkyl, and $OC_{1-8}$-alkyl substituted with 1, 2 or 3 halogens or OH groups; and $R^2$ is an optionally substituted 5- or 6-membered aromatic heterocycle comprising 2 or 3 heteroatoms independently selected from the group consisting of N, S and O, wherein said 5- or 6-membered aromatic heterocycle is optionally substituted with 1, 2 or 3 substituents, each substituent being independently selected from the group consisting of $C_3$alkyl and $C_{1-3}$ alkyl substituted with 1, 2 or 3 halogens.

§ 2. A compound as defined in § 1, with the proviso that the compounds is not selected from the group consisting of

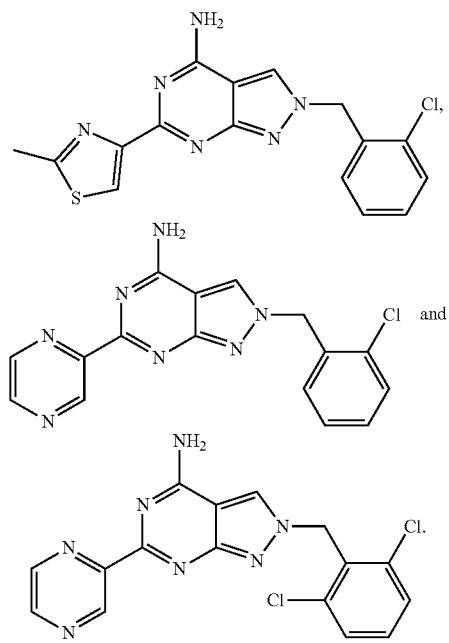

§ 3. A compound as defined in § 1 or § 2, wherein $R^1$ is an optionally substituted phenyl, or an optionally substituted 5- or 6-membered aromatic heterocycle comprising 1, 2 or 3 heteroatoms independently selected from the group consisting of N, S and O, wherein said phenyl is optionally substituted with 1, 2 or 3 substituents, each substituent being independently selected from the group consisting of fluorine, meta-chlorine, para-chorine, OH, $C_{1-8}$alkyl, $C_{1-4}$alkyl substituted with 1, 2 or 3 halogens or OH groups, $OC_{1-8}$alkyl, and $OC_{1-8}$ alkyl substituted with 1, 2 or 3 halogens or OH groups, and wherein said 5- or 6-membered aromatic heterocycle is optionally substituted with 1, 2 or 3 substituents, each substituent being independently selected from the group consisting of halogen, OH, $C_{1-8}$alkyl, $C_{1-8}$alkyl substituted with 1, 2 or 3 halogens or OH groups, $OC_{1-8}$-alkyl, and $OC_{1-8}$alkyl substituted with 1, 2 or 3 halogens or OH groups; or wherein $R^1$ is an optionally substituted phenyl, or an optionally substituted 5- or 6-membered aromatic heterocycle comprising 1, 2 or 3 heteroatoms independently selected from the group consisting of N, S and O, wherein said phenyl is optionally substituted with 1, 2 or 3 substituents, each substituent being independently selected from the group consisting of fluorine, OH, $C_{1-8}$alkyl, $C_{1-8}$alkyl substituted with 1, 2 or 3 halogens or OH groups, $OC_{1-8}$alkyl, and $OC_{1-8}$alkyl substituted with 1, 2 or 3 halogens or OH groups, and wherein said 5- or 6-membered aromatic heterocycle is optionally substituted with 1, 2 or 3 substituents, each substituent being independently selected from the group consisting of halogen, OH, $C_{1-8}$alkyl, $C_{1-8}$alkyl substituted with 1, 2 or 3 halogens or OH groups, $OC_{1-8}$alkyl, and $OC_{1-8}$alkyl substituted with 1, 2 or 3 halogens or OH groups.

§ 4. A compound as defined in any one of § 1 or § 3, wherein $R^1$ is an optionally substituted phenyl, or an optionally substituted 5- or 6-membered aromatic heterocycle comprising 1 or 2 heteroatoms independently selected from the group consisting of N and S.

§ 5. A compound as defined in any one of § 1, § 2 or § 4, wherein when $R^1$ is a substituted phenyl, said phenyl is substituted with 1, 2 or 3 substituents, each substituent being independently selected from the group consisting of halogen (preferably F or Cl, and more preferably F or meta or para C), $C_{1-8}$alkyl, $C_{1-8}$alkyl substituted with 1, 2 or 3 halogens (preferably F) or OH groups (preferably 1 OH group, e.g. $CH_2H$), $OC_{1-8}$alkyl, and $OC_{1-8}$alkyl substituted with 1, 2 or 3 halogens (preferably F) or OH groups (preferably 1 OH group).

§ 6. A compound as defined in any one of § 1 to § 5, wherein when $R^1$ is a substituted phenyl, said phenyl is substituted with 1 or 2 substituents, each substituent being independently selected from the group consisting of $C_{1-4}$alkyl, $C_1$-4alkyl substituted with 1, 2 or 3 halogens (preferably F), $OC_{1-8}$alkyl, and $OC_{1-4}$alkyl substituted with 1, 2 or 3 halogens (preferably F).

§ 7. A compound as defined in any one of § 1, § 2 or § 4 to § 5, wherein when $R^1$ is a substituted phenyl, said phenyl is substituted with 1 or 2 substituents, each substituent being independently selected from the group consisting of halogen (e.g. F or C, preferably F or meta or para C), $C_{1-4}$alkyl, $C_{1-8}$alkyl substituted with 1, 2 or 3 halogens (preferably F) or OH groups (preferably 1 OH group), and $OC_{1-8}$-alkyl; and more preferably each substituent being independently selected from the group consisting of halogen (e.g. F or C), $C_{2-4}$alkyl, $C_{1-4}$ alkyl substituted with 1 OH groups, and $OC_{1-4}$alkyl.

§ 8. A compound as defined in any one of § 1, § 2 or § 4, wherein $R^1$ is an optionally substituted phenyl, or an optionally substituted 5- or 6-membered aromatic heterocycle comprising 1, 2 or 3 heteroatoms independently selected from the group consisting of N, S and O, wherein said phenyl is optionally substituted with 1, 2 or 3 substituents, each substituent being independently selected from the group consisting of halogen, OH, $C_{1-8}$alkyl, $C_{1-4}$alkyl substituted with 1, 2 or 3 halogens, $OC_{1-8}$alkyl, and $OC_{1-8}$alkyl substituted with 1, 2 or 3 halogens, and wherein said 5- or 6-membered aromatic heterocycle is optionally substituted with 1, 2 or 3 substituents, each substituent being independently selected from the group consisting of halogen, OH, $C_{1-8}$-alkyl, $C_{1-8}$-alkyl substituted with 1, 2 or 3 halogens, $OC_{1-8}$alkyl, and $OC_{1-8}$alkyl substituted with 1, 2 or 3 halogens.

§ 9. A compound as defined in § 8, wherein when $R^1$ is a substituted phenyl, said phenyl is substituted with 1, 2 or 3 substituents, each substituent being independently selected from the group consisting of halogen (preferably F or C, and more preferably F or meta or para Cl), $C_{1-8}$-alkyl, $C_{1-8}$-alkyl substituted with 1, 2 or 3 halogens (preferably F), $OC_{1-8}$-alkyl, and $OC_{1-8}$ alkyl substituted with 1, 2 or 3 halogens (preferably F).

§ 10. A compound as defined in § 8 or § 9, wherein when $R^1$ is a substituted phenyl, said phenyl is substituted with 1 or 2 substituents, each substituent being independently selected from the group consisting of $C_{1-4}$alkyl, $C_{1-4}$alkyl substituted with 1, 2 or 3 halogens (preferably F), $OC_{1-8}$-alkyl, and $OC_{1-4}$alkyl substituted with 1, 2 or 3 halogens (preferably F).

§ 11. A compound as defined in any one of § 8 to § 10, wherein when $R^1$ is a substituted phenyl, said phenyl is substituted with 1 or 2 substituents, each substituent being independently selected from the group consisting of halogen (e.g. F or Cl, preferably F or meta or para C), $C_{2-4}$alkyl, $C_{2-4}$alkyl substituted with 1, 2 or 3 halogens (preferably F), and $OC_{1-4}$alkyl; and more preferably each substituent being independently selected from the group consisting of halogen (e.g. F or C), $C_{2-4}$alkyl, and $OC_{1-4}$alkyl.

§ 12. A compound as defined in any one of § 1 to § 11, wherein $R^1$ is a substituted phenyl.

§ 13. A compound as defined in any one of § 1 to § 11, wherein $R^2$ is an optionally substituted 5- or 6-membered aromatic heterocycle comprising 2 or 3 heteroatoms independently selected from the group consisting of N, S and O, wherein at least one of the heteroatoms is N.

§ 14. A compound as defined in any one of § 1 to § 13, wherein $R^2$ is an optionally substituted 5- or 6-membered aromatic heterocycle selected from the group consisting of imidazolyl (1,3-diazolyl), pyrazolyl (1,2-diazolyl), 1,3-oxazolyl, isoxazolyl (1,2-oxazolyl), thiazolyl (1,3-thiazolyl), isothiazolyl (1,2-thiazolyl), 1H-1,2,3-triazolyl, 2H-1,2,3-triazolyl, 1H-1,2,4-triazolyl, 4H-1,2,4-triazolyl, furazanyl (1,2,5-oxadiazolyl), 1,2,3-oxadiazolyl, 1,2,4-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), pyrazinyl (1,4-diazinyl), 1,2,3-triazinyl, 1,2,4-triazinyl, and 1,3,5-triazinyl; and preferably wherein $R^2$ is an optionally substituted 5- or 6-membered aromatic heterocycle selected from the group consisting of imidazolyl (1,3-diazolyl), pyrazolyl (1,2-diazolyl), 1,3-oxazolyl, isoxazolyl (1,2-oxazolyl), thiazol-2-yl (1,3-thiazol-2-yl), isothiazolyl (1,2-thiazolyl), 1H-1,2,3-triazolyl, 2H-1,2,3-triazolyl, 1H-1,2,4-triazolyl, 4H-1,2,4-triazolyl, furazanyl (1,2,5-oxadiazolyl), 1,2,3-oxadiazolyl, 1,2,4-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), pyrazinyl (1,4-diazinyl), 1,2,3-triazinyl, 1,2,4-triazinyl, and 1,3,5-triazinyl.

§ 15. A compound as defined in any one of § 1 to § 14, wherein $R^2$ is an optionally substituted 5- or 6-membered aromatic heterocycle selected from the group consisting of 1,3-oxazolyl, isoxazolyl (1,2-oxazolyl), thiazolyl (1,3-thiazolyl), isothiazolyl (1,2-thiazolyl), 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), and pyrazinyl (1,4-diazinyl); and preferably wherein $R^2$ is an optionally substituted 5- or 6-membered aromatic heterocycle selected from the group consisting of 1,3-oxazolyl, isoxazolyl (1,2-oxazolyl), thiazol-2-yl (1,3-thiazol-2-yl), isothiazolyl (1,2-thiazolyl), 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), and pyrazinyl (1,4-diazinyl).

§ 16. A compound as defined in any one of § 1 to § 15, wherein $R^2$ is an optionally substituted 5- or 6-membered aromatic heterocycle comprising 2 or 3 heteroatoms independently selected from the group consisting of N and S, and preferably wherein at least one of the heteroatoms is N.

§ 17. A compound as defined in any one of § 1 to § 15, wherein $R^2$ is an unsubstituted 5- or 6-membered aromatic heterocycle selected from the group consisting of 1,3-oxazolyl, isoxazolyl (1,2-oxazolyl), thiazolyl (1,3-thiazolyl), isothiazolyl (1,2-thiazolyl), and pyrazinyl (1,4-diazinyl) (preferably selected from the group consisting of pyrazinyl (1,4-diazinyl, e.g. pyrazin-2-yl), isothiazolyl (1,2-thiazolyl, e.g. 1,2-thiazol-3-yl) and 1,3-oxazolyl (e.g. 1,3-oxazol-5-yl)).

§ 18. A compound as defined in any one of § 1 to § 15, wherein $R^2$ is an unsubstituted 5- or 6-membered aromatic heterocycle selected from the group consisting of isothiazolyl (1,2-thiazolyl) and pyrazinyl (1,4-diazinyl) (preferably isothiazol-3-yl (1,2-thiazol-3-yl) and pyrazin-2-yl (1,4-diazin-2-yl)).

§ 19. A compound as defined in any one of § 1 to § 15, wherein $R^2$ is an optionally substituted 5- or 6-membered aromatic heterocycle selected from the group consisting of pyrazinyl, 1,2-thiazolyl, 1,3-oxazolyl, 1,2,3-thiadiazolyl, 1,3-thiazolyl, and 1,2-oxazolyl (preferably pyrazin-2-yl, 1,2-thiazol-3-yl, 1,3-oxazol-5-yl, 1,3-oxazol-2-yl, 1,2,3-thiadiazol-5-yl, 1,3-thiazol-2-yl, and 1,2-oxazol-5-yl); and preferably wherein $R^2$ is an optionally substituted 5- or 6-membered aromatic heterocycle selected from the group consisting of pyrazinyl, 1,2-thiazolyl, 1,3-oxazolyl, 1,2,3-thiadiazolyl, 1,3-thiazol-2-yl, and 1,2-oxazolyl (preferably pyrazin-2-yl, 1,2-thiazol-3-yl, 1,3-oxazol-5-yl, 1,3-oxazol-2-yl, 1,2,3-thiadiazol-5-yl, 1,3-thiazol-2-yl, and 1,2-oxazol-5-yl).

§ 20. A compound as defined in any one of § 1 to § 11, wherein $R^2$ is a 5- or 6-membered aromatic heterocycle selected from the group consisting of unsubstituted pyrazinyl, unsubstituted 1,2-thiazolyl, unsubstituted 1,3-oxazolyl, and 1,2,3-thiadiazolyl substituted with one $C_{1-4}$alkyl group (preferably unsubstituted pyrazin-2-yl, unsubstituted 1,2-thiazol-3-yl, unsubstituted 1,3-oxazol-5-yl, unsubstituted 1,3-oxazol-2-yl, 4-methyl-1,2,3-thiadiazol-5-yl).

§ 21. A compound as defined in any one of § 1 to § 15, § 19 or § 20, wherein $R^2$ is an optionally substituted 5- or 6-membered aromatic heterocycle, and wherein said 5- or 6-membered aromatic heterocycle is optionally substituted with 1 or 2 substituents (preferably 1 substituent), each substituent being independently selected from the group consisting of $C_{1-3}$ alkyl and $C_{1-3}$alkyl substituted with 1, 2 or 3 fluorines; or wherein $R^2$ is an unsubstituted 5- or 6-membered aromatic heterocycle.

§ 22. A compound as defined in any one of § 1 to § 15 or § 19 to § 20, wherein $R^2$ is an optionally substituted 5- or 6-membered aromatic heterocycle, and wherein when the 5- or 6-membered aromatic heterocycle is substituted, each substituent is methyl.

§ 23. A compound as defined in § 1, wherein the compound is selected from the group consisting of 2-[(3-methylphenyl)methyl]-6-(1,2-thiazol-3-yl)-2H-pyrazolo[3,4-d]pyrimidin-4-amine;
2-[(3-methoxyphenyl)methyl]-6-(pyrazin-2-yl)-2H-pyrazolo[3,4-d]pyrimidin-4-amine;
3-{[4-amino-6-(pyrazin-2-yl)-2H-pyrazolo[3,4-d]pyrimidin-2-yl]methyl}phenol;
2-[(3-methoxyphenyl)methyl]-6-(1,3-oxazol-2-yl)-2H-pyrazolo[3,4-d]pyrimidin-4-amine;
2-[(3-methoxyphenyl)methyl]-6-(4-methyl-1,3-thiazol-2-yl)-2H-pyrazolo[3,4-d]pyrimidin-4-amine;
2-[(3-methoxyphenyl)methyl]-6-(3-methyl-1,2-oxazol-5-yl)-2H-pyrazolo[3,4-d]pyrimidin-4-amine;
2-[(3-methoxyphenyl)methyl]-6-(4-methyl-1,2,3-thiadiazol-5-yl)-2H-pyrazolo[3,4-d]pyrimidin-4-amine;
2-[(3-methoxyphenyl)methyl]-6-(1,3-thiazol-2-yl)-2H-pyrazolo[3,4-d]pyrimidin-4-amine;
2-[(3-methoxyphenyl)methyl]-6-(1,3-thiazol-4-yl)-2H-pyrazolo[3,4-d]pyrimidin-4-amine;
2-[(3-methoxyphenyl)methyl]-6-(1,2-thiazol-3-yl)-2H-pyrazolo[3,4-d]pyrimidin-4-amine;
2-[(3-methoxyphenyl)methyl]-6-(1,3-oxazol-5-yl)-2H-pyrazolo[3,4-d]pyrimidin-4-amine;
2-[(4-methylphenyl)methyl]-6-(pyrazin-2-yl)-2H-pyrazolo[3,4-d]pyrimidin-4-amine;
2-[(4-methylphenyl)methyl]-6-(1,2-thiazol-3-yl)-2H-pyrazolo[3,4-d]pyrimidin-4-amine;
2-[(4-methylphenyl)methyl]-6-(1,3-thiazol-2-yl)-2H-pyrazolo[3,4-d]pyrimidin-4-amine;
2-[(4-methoxyphenyl)methyl]-6-(pyrazin-2-yl)-2H-pyrazolo[3,4-d]pyrimidin-4-amine;
6-(1,2-thiazol-3-yl)-2-{[3-(trifluoromethoxy)phenyl]methyl}-2H-pyrazolo[3,4-d]pyrimidin-4-amine;
6-(1,2-thiazol-3-yl)-2-{[4-(trifluoromethyl)phenyl]methyl}-2H-pyrazolo[3,4-d]pyrimidin-4-amine;
2-[(3-methoxy-4-methylphenyl)methyl]-6-(1,2-thiazol-3-yl)-2H-pyrazolo[3,4-d]pyrimidin-4-amine;
2-[(3-fluoro-4-methylphenyl)methyl]-6-(1,2-thiazol-3-yl)-2H-pyrazolo[3,4-d]pyrimidin-4-amine;
2-[(2,5-dichlorophenyl)methyl]-6-(1,2-thiazol-3-yl)-2H-pyrazolo[3,4-d]pyrimidin-4-amine;
2-[(3,4-dimethylphenyl)methyl]-6-(1,2-thiazol-3-yl)-2H-pyrazolo[3,4-d]pyrimidin-4-amine;
2-[(pyridin-2-yl)methyl]-6-(1,2-thiazol-3-yl)-2H-pyrazolo[3,4-d]pyrimidin-4-amine;
2-[(6-methylpyridin-3-yl)methyl]-6-(1,2-thiazol-3-yl)-2H-pyrazolo[3,4-d]pyrimidin-4-amine;
2-{[4-methyl-3-(trifluoromethyl)phenyl]methyl}-6-(1,2-thiazol-3-yl)-2H-pyrazolo[3,4-d]pyrimidin-4-amine;
2-[(2-methoxy-4-methylphenyl)methyl]-6-(1,2-thiazol-3-yl)-2H-pyrazolo[3,4-d]pyrimidin-4-amine;
2-[(3-methylphenyl)methyl]-6-(1,3-oxazol-2-yl)-2H-pyrazolo[3,4-d]pyrimidin-4-amine;
2-[(3-methylphenyl)methyl]-6-(pyrazin-2-yl)-2H-pyrazolo[3,4-d]pyrimidin-4-amine;
6-(pyrazin-2-yl)-2-{[3-(trifluoromethyl)phenyl]methyl}-2H-pyrazolo[3,4-d]pyrimidin-4-amine;
2-[(3-fluorophenyl)methyl]-6-(1,2-thiazol-3-yl)-2H-pyrazolo[3,4-d]pyrimidin-4-amine;
2-[(3-fluorophenyl)methyl]-6-(pyrazin-2-yl)-2H-pyrazolo[3,4-d]pyrimidin-4-amine;
2-[(2-methylphenyl)methyl]-6-(pyrazin-2-yl)-2H-pyrazolo[3,4-d]pyrimidin-4-amine;
2-[(2-methylphenyl)methyl]-6-(1,2-thiazol-3-yl)-2H-pyrazolo[3,4-d]pyrimidin-4-amine;
6-(1,3-thiazol-2-yl)-2-[(1,3-thiazol-2-yl)methyl]-2H-pyrazolo[3,4-d]pyrimidin-4-amine;
2-[(1,3-thiazol-2-yl)methyl]-6-(1,2-thiazol-3-yl)-2H-pyrazolo[3,4-d]pyrimidin-4-amine;
2-[(3-chlorophenyl)methyl]-6-(1,2-thiazol-3-yl)-2H-pyrazolo[3,4-d]pyrimidin-4-amine;
2-[(3-chlorophenyl)methyl]-6-(pyrazin-2-yl)-2H-pyrazolo[3,4-d]pyrimidin-4-amine;
2-[(2-methoxyphenyl)methyl]-6-(pyrazin-2-yl)-2H-pyrazolo[3,4-d]pyrimidin-4-amine;
2-[(2-methoxyphenyl)methyl]-6-(1,2-thiazol-3-yl)-2H-pyrazolo[3,4-d]pyrimidin-4-amine;
2-[(2-methoxyphenyl)methyl]-6-(1,3-oxazol-2-yl)-2H-pyrazolo[3,4-d]pyrimidin-4-amine;
2-[(2-methoxyphenyl)methyl]-6-(1,3-oxazol-5-yl)-2H-pyrazolo[3,4-d]pyrimidin-4-amine;
2-[(3,4-dimethoxyphenyl)methyl]-6-(pyrazin-2-yl)-2H-pyrazolo[3,4-d]pyrimidin-4-amine;
3-{[4-amino-6-(1,2-thiazol-3-yl)-2H-pyrazolo[3,4-d]pyrimidin-2-yl]methyl}phenol;
2-{[4-amino-6-(1,2-thiazol-3-yl)-2H-pyrazolo[3,4-d]pyrimidin-2-yl]methyl}-5-methylphenol;
2-{[4-amino-6-(1,2-thiazol-3-yl)-2H-pyrazolo[3,4-d]pyrimidin-2-yl]methyl}phenol;
5-{[4-amino-6-(1,2-thiazol-3-yl)-2H-pyrazolo[3,4-d]pyrimidin-2-yl]methyl}-2-methylphenol; and
[3-[(4-amino-6-(1,2-thiazol-3-yl)-pyrazolo[3,4-d]pyrimidin-2-yl)methyl]phenyl]methanol;
or pharmaceutically acceptable ester, amide, carbamate, solvate or salt thereof, including a salt of such an ester, amide or carbamate.

§ 24. A pharmaceutical composition which comprises a compound as defined in any one of § 1 to § 23, together with a pharmaceutically suitable carrier.

§ 25. A composition as defined in § 24, which also contains a further therapeutic agent.

§ 26. A compound as defined in any one of § 1 to § 23, or a composition as defined in § 24 or § 25, for use as a medicament.

§ 27. A compound as defined in any one of § 1 to § 23, or a composition as defined in § 24 or § 25, for use in the treatment or prophylaxis of a disease or disorder associated with the adenosine 2a receptor.

§ 28. Use of a compound as defined in any one of § 1 to § 23, for the manufacture of a medicament for the treatment or prophylaxis of a disease or disorder associated with the adenosine 2a receptor.

§ 29. A method for the treatment or prophylaxis of a disease or disorder associated with the adenosine 2a receptor in a mammal, which comprises administering to the mammal a therapeutically effective amount of a compound as defined in any one of § 1 to § 23, or a composition as defined in § 24 or § 25.

§ 30. Use of a compound as defined in any one of § 1 to § 23 in labelled form as a diagnostic agent for the diagnosis of a disease or disorder associated with the adenosine 2a receptor.

§ 31. Use of a compound as defined in any one of § 1 to § 23 or a labelled form of such a compound as a reference compound in a method of identifying ligands for the adenosine 2a receptor.

§ 32. A compound or a composition as defined in § 27, or a use as defined in § 28, or a method as defined in § 29, wherein the disease or disorder associated with the adenosine 2a receptor is a disease or disorder selected from the group consisting of cancer, neurodegenerative diseases, retinal degenerative diseases, insomnia, pain, psychiatric diseases, ischemia, infarction, acute inflammatory diseases, chronic inflammatory diseases, spinal cord injury, and epilepsy.

§ 33. A compound or a composition as defined in § 27, or a use as defined in § 28, or a method as defined in § 29, wherein the disease or disorder associated with the adenosine 2a receptor is cancer, and wherein the cancer is selected from the group consisting of lymphoma (for example B cell lymphoma), sarcoma (for example osteosarcoma), bladder cancer, bone cancer, brain tumor, cervical cancer, renal cell cancer, colorectal cancer (for example colon cancer or colorectal cancer with microsatellite instability), esophageal cancer, gastric cancer, head and neck cancer, kidney cancer, myeloma, thyroid cancer, leukaemia (for example acute myeloid leukaemia), breast cancer (e.g. triple negative, ER positive, ER negative, chemotherapy resistant, Herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer (for example castration-resistant prostate cancer), glioblastoma, squamous cell carcinoma (e.g. head, neck, or esophagus), multiple myeloma, skin cancer (e.g. Merkel cell carcinoma), testicular cancer, neuroblastoma and metastatic cancer.

The invention claimed is:

1. A compound of formula (I), or pharmaceutically acceptable ester, amide, carbamate, solvate or salt thereof, including a salt of such an ester, amide or carbamate,

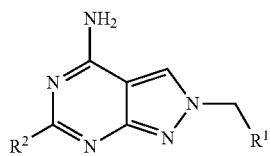

(I)

wherein $R^1$ is an optionally substituted phenyl, or an optionally substituted 5- or 6-membered aromatic heterocycle comprising 1, 2 or 3 heteroatoms independently selected from the group consisting of N, S and O, wherein said phenyl is optionally substituted with 1, 2 or 3 substituents, each substituent being independently selected from the group consisting of halogen, OH, $C_{1-8}$alkyl, $C_{1-8}$aklyl substituted with 1, 2 or 3 halogens or OH groups, $OC_{1-8}$alkyl, and $OC_{1-8}$alkyl substituted with 1, 2 or 3 halogens or OH groups, and wherein said 5- or 6-membered aromatic heterocycle is optionally substituted with 1, 2 or 3 substituents, each substituent being independently selected from the group consisting of halogen, OH, $C_{1-8}$alkyl, $C_{1-8}$alkyl substituted with 1, 2 or 3 halogens or OH groups, $OC_{1-8}$alkyl, and $OC_{1-8}$alkyl substituted with 1, 2 or 3 halogens or OH groups; and $R^2$ is an optionally substituted 5- or 6-membered aromatic heterocycle comprising 2 or 3 heteroatoms independently selected from the group consisting of N, S and O, wherein said 5- or 6-membered aromatic heterocycle is optionally substituted with 1, 2 or 3 substituents, each substituent being independently selected from the group consisting of $C_{1-3}$alkyl and $C_{1-3}$alkyl substituted with 1, 2 or 3 halogens;

with the proviso that the compound is not selected from the group consisting of

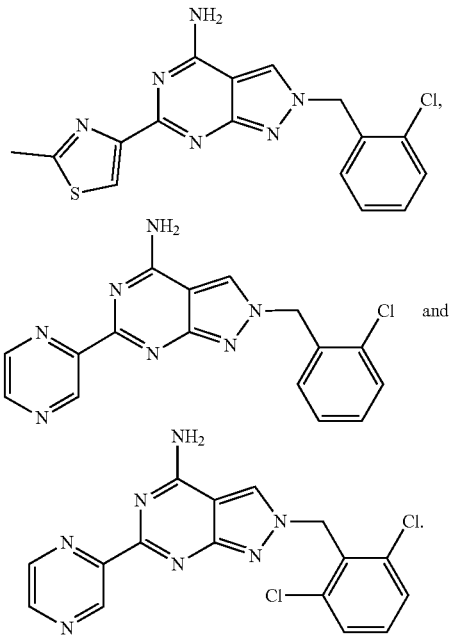

2. A compound as claimed in claim 1, wherein $R^1$ is an optionally substituted phenyl, or an optionally substituted 5- or 6-membered aromatic heterocycle comprising 1, 2 or 3 heteroatoms independently selected from the group consisting of N, S and O, wherein said phenyl is optionally substituted with 1, 2 or 3 substituents, each substituent being independently selected from the group consisting of fluorine, meta-chlorine, para-chorine, OH, $C_{1-8}$alkyl, $C_{1-8}$alkyl substituted with 1, 2 or 3 halogens or OH groups, $OC_{1-8}$alkyl, and $OC_{1-8}$alkyl substituted with 1, 2 or 3 halogens or OH groups, and wherein said 5- or 6-membered aromatic heterocycle is optionally substituted with 1, 2 or 3 substituents, each substituent being independently selected from the group consisting of halogen, OH, $C_{1-8}$alkyl, $C_{1-8}$alkyl substituted with 1, 2 or 3 halogens or OH groups, $OC_{1-8}$alkyl, and $OC_{1-8}$alkyl substituted with 1, 2 or 3 halogens or OH groups.

3. A compound as claimed in claim 1, wherein $R^1$ is an optionally substituted phenyl, or an optionally substituted 5- or 6-membered aromatic heterocycle comprising 1 or 2 heteroatoms independently selected from the group consisting of N and S.

4. A compound as claimed in claim 1, wherein when $R^1$ is a substituted phenyl, said phenyl is substituted with 1, 2 or 3 substituents, each substituent being independently selected from the group consisting of halogen, $C_{1-8}$alkyl, $C_{1-8}$alkyl substituted with 1, 2 or 3 halogens or OH groups, $OC_{1-8}$alkyl, and $OC_{1-8}$alkyl substituted with 1, 2 or 3 halogens.

5. A compound as claimed in claim 1, wherein when $R^1$ is a substituted phenyl, said phenyl is substituted with 1 or 2 substituents, each substituent being independently selected from the group consisting of $C_{1-4}$alkyl, $C_{1-4}$alkyl substituted with 1, 2 or 3 halogens or OH groups, $OC_{1-4}$alkyl, and $OC_{1-4}$alkyl substituted with 1, 2 or 3 halogens or OH groups.

6. A compound as claimed in claim 1, wherein when $R^1$ is a substituted phenyl, said phenyl is substituted with 1 or 2 substituents, each substituent being independently selected from the group consisting of halogen, $C_{1-4}$alkyl, $C_{1-4}$alkyl substituted with 1, 2 or 3 halogens or OH groups, and $OCC_{1-8}$alkyl.

7. A compound as claimed in claim 1, wherein $R^1$ is a substituted phenyl.

8. A compound as claimed claim 1, wherein $R^2$ is an optionally substituted 5- or 6-membered aromatic heterocycle comprising 2 or 3 heteroatoms independently selected from the group consisting of N, S and O, wherein at least one of the heteroatoms is N.

9. A compound as claimed in claim 1, wherein $R^2$ is an optionally substituted 5- or 6-membered aromatic heterocycle selected from the group consisting of imidazolyl (1,3-diazolyl), pyrazolyl (1,2-diazolyl), 1,3-oxazolyl, isoxazolyl (1,2-oxazolyl), thiazolyl (1,3-thiazolyl), thiazol-2-yl (1,3-thiazol-2-yl), isothiazolyl (1,2-thiazolyl), 2H-1,2,3-triazolyl, 1H-1,2,4-triazolyl, 4H-1,2,4-triazolyl, furazanyl (1,2,5-oxadiazolyl), 1,2,3-oxadiazolyl, 1,2,4-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, pyridazinyl (1,2-diazinyl), pyrimidinyl (1,3-diazinyl), pyrazinyl (1,4-diazinyl), 1,2,3-triazinyl, 1,2,4-triazinyl, and 1,3,5-triazinyl.

10. A compound as claimed in claim 1, wherein $R^2$ is an optionally substituted 5- or 6-membered aromatic heterocycle, and wherein said 5- or 6-membered aromatic heterocycle is optionally substituted with 1 or 2 substituents, each substituent being independently selected from the group consisting of $C_{1-3}$alkyl and $C_{1-3}$alkyl substituted with 1, 2 or 3 fluorines.

11. A compound as claimed in claim 1, wherein the compound is selected from the group consisting of
  2-[(3-methylphenyl)methyl]-6-(1,2-thiazol-3-yl)-2H-pyrazolo[3,4-d]pyrimidin-4-amine;
  2-[(3-methoxyphenyl)methyl]-6-(pyrazin-2-yl)-2H-pyrazolo[3,4-d]pyrimidin-4-amine;
  3-{[4-amino-6-(pyrazin-2-yl)-2H-pyrazolo[3,4-d]pyrimidin-2-yl]methyl}phenol;
  2-[(3-methoxyphenyl)methyl]-6-(1,3-oxazol-2-yl)-2H-pyrazolo[3,4-d]pyrimidin-4-amine;
  2-[(3-methoxyphenyl)methyl]-6-(4-methyl-1,3-thiazol-2-yl)-2H-pyrazolo[3,4-d]pyrimidin-4-amine;
  2-[(3-methoxyphenyl)methyl]-6-(3-methyl-1,2-oxazol-5-yl)-2H-pyrazolo[3,4-d]pyrimidin-4-amine;
  2-[(3-methoxyphenyl)methyl]-6-(4-methyl-1,2,3-thiadiazol-5-yl)-2H-pyrazolo[3,4-d]pyrimidin-4-amine;
  2-[(3-methoxyphenyl)methyl]-6-(1,3-thiazol-1-yl)-2H-pyrazolo[3,4-d]pyrimidin-4-amine;
  2-[(3-methoxyphenyl)methyl]-6-(1,3-thiazol-4-yl)-2H-pyrazolo[3,4-d]pyrimidin-4-amine;
  2-[(3-methoxyphenyl)methyl]-6-(1,2-thiazol-3-yl)-2H-pyrazolo[3,4-d]pyrimidin-4-amine;
  2-[(3-methoxyphenyl)methyl]-6-(1,3-oxazol-5-yl)-2H-pyrazolo[3,4-d]pyrimidin-4-amine;
  2-[(4-methyl phenyl)methyl]-6-(pyrazin-2-yl)-2H-pyrazolo[3,4-d]pyrimidin-4-amine;
  2-[(4-methylphenyl)methyl]-6-(1,2-thiazol-3-yl)-2H-pyrazolo[3,4-d]pyrimidin-4-amine;
  2-[(4-methylphenyl)methyl]-6-(1,3-thiazol-2-yl)-2H-pyrazolo[3,4-d]pyrimidin-4-amine;
  2-[(4-methoxyphenyl)methyl]-(4pyrazin-2-yl)-2H-pyrazolo[3,4-d]pyrimidin-4-amine;
  6-(1,2-thiazol-3-yl)-2-{[3-(trifluoromethoxy)phenyl]methyl}-2H-pyrazolo[3,4-d]pyrimidin-4-amine;
  6-(1,2-thiazol-3-yl)-2-{[4-(trifluoromethyl)phenyl]methyl}-2H-pyrazolo[3,4-d]pyrimidin-4-amine;
  2-[(3-methoxy-4-methylphenyl)methyl]-6-(1,2-thiazol-3-yl)-2H-pyrazolo[3,4-d]pyrimidin-4-amine;
  2-[(3-fluoro-4-methylphenyl)methyl]-6-(1,2-thiazol-3-yl)-2H-pyrazolo[3,4-d]pyrimidin-4-amine;
  2-[(2,5-dichlorophenyl)methyl]-6-(1,2-thiazol-3-yl)-2H-pyrazolo[3,4-d]pyrimidin-4-amine;
  2-[(3,4-dimethylphenyl)methyl]-6-(1,2-thiazol-3-yl)-2H-pyrazolo[3,4-d]pyrimidin-4-amine;
  2-[(pyridin-2-yl)methyl]-6-(1,2-thiazol-3-yl)-2H-pyrazolo[3,4-d]pyrimidin-4-amine;
  2-[(6-methylpyridin-3-yl)methyl]-6-(1,2-thiazol-3-yl)-2H-pyrazolo[3,4-d]pyrimidin-4-amine;
  2-{[4-methyl-3-(trifluoromethyl)phenyl]methyl}-6-(1,2-thiazol-3-yl)-2H-pyrazolo[3,4-d]pyrimidin-4-amine;
  2-[(2-methoxy-4-methylphenyl)methyl]-6-(1,2-thiazol-3-yl)-2H-pyrazolo[3,4-d]pyrimidin-4-amine;
  2-[(3-methylphenyl)methyl]-6-(1,3-oxazol-2-yl)-2H-pyrazolo[3,4-d]pyrimidin-4-amine;
  2-[(3-methylphenyl)methyl]-64pyrazin-2-yl)-2H-pyrazolo[3,4-d]pyrimidin-4-amine;
  64pyrazin-2-yl)-2-{[3-(trifluoromethyl)phenyl]methyl}-2H-pyrazolo[3,4-d]pyrimidin-4-amine;
  2-[(3-fluorophenyl)methyl]-6-(1,2-thiazol-3-yl)-2H-pyrazolo[3,4-d]pyrimidin-4-amine;
  2-[(3-fluorophenylmethyl]-64pyrazin-2-yl)-2H-pyrazolo[3,4-d]pyrimidin-4-amine;
  2-[(2-methylphenyl)methyl]-64pyrazin-2-yl)-2H-pyrazolo[3,4-d]pyrimidin-4-amine;
  2-[(2-methylphenyl)methyl]-6-(1,2-thiazol-3-yl)-2H-pyrazolo[3,4-d]pyrimidin-4-amine;
  6-(1,3-thiazol-2-yl)-2-[(1,3-thiazol-2-yl)methyl]-2H-pyrazolo[3,4-d]pyrimidin-4-amine;
  2-[(1,3-thiazol-2-yl)methyl]-6-(1,2-thiazol-3-yl)-2H-pyrazolo[3,4-d]pyrimidin-4-amine;
  2-[(3-chlorophenyl)methyl]-6-(1,2-thiazol-3-yl)-2H-pyrazolo[3,4-d]pyrimidin-4-amine;
  2-[(3-chlorophenyl)methyl]-6-(pyrazin-2-yl)-2H-pyrazolo[3,4-d]pyrimidin-4-amine;
  2-[(2-methoxyphenyl)methyl]-6-(pyrazin-2-yl)-2H-pyrazolo[3,4-d]pyrimidin-4-amine;
  2-[(2-methoxyphenyl)methyl]-6-(1,2-thiazol-3-yl)-2H-pyrazolo[3,4-d]pyrimidin-4-amine;
  2-[(2-methoxyphenyl)methyl]-6-(1,3-oxazol-2-yl)-2H-pyrazolo[3,4-d]pyrimidin-4-amine;
  2-[(2-methoxyphenyl)methyl]-6-(1,3-oxazol-5-yl)-2H-pyrazolo[3,4-d]pyrimidin-4-amine;
  2-[(3,4-dimethoxyphenyl)methyl]-6-(pyrazin-2-yl)-2H-pyrazolo[3,4-d]pyrimidin-4-amine;
  3-{[4-amino-6-(1,2-thiazol-3-yl)-2H-pyrazolo[3,4-d]pyrimidin-2-yl]methyl}phenol;
  2-{[4-amino-6-(1,2-thiazol-3-yl)-2H-pyrazolo[3,4-d]pyrimidin-2-yl]methyl}-5-meth phenol;
  2-{[4-amino-6-(1,2-thiazol-3-yl)-2H-pyrazolo[3,4-d]pyrimidin-2-yl]methyl}phenol;
  5-{[4-amino-6-(1,2-thiazol-3-yl)-2H-pyrazolo[3,4-d]pyrimidin-2-yl]methyl}-2-methyl phenol; and
  [3-[(4-amino-6-(1,2-thiazol-3-yl)-pyrazolo[3,4-d]pyrimidin-2-yl)methyl]phenyl]methanol;
  or pharmaceutically acceptable ester, amide, carbamate, solvate or salt thereof, including a salt of such an ester, amide or carbamate.

12. A pharmaceutical composition which comprises a compound claimed in claim 1, together with a pharmaceutically suitable carrier, and optionally also comprises a further therapeutic agent.

13. A diagnostic agent for the diagnosis of a disease or disorder associated with the adenosine 2a receptor, comprising the compound of claim 1 in labelled form.

14. A method for the treatment of a disease or disorder associated with the adenosine 2a receptor in a mammal, which comprises administering to the mammal a therapeutically effective amount of a compound as claimed in claim 1.

15. The method as claimed in claim 14, wherein the disease or disorder associated with the adenosine 2a receptor is a disease or disorder selected from the group consisting of cancer, neurodegenerative diseases, retinal degenerative diseases, insomnia, pain, psychiatric diseases, ischemia, infarction, acute inflammatory diseases, chronic inflammatory diseases, spinal cord injury, and epilepsy.

16. The method as claimed in claim 14, wherein the disease or disorder associated with the adenosine 2a receptor is cancer, and wherein the cancer is selected from the group consisting of lymphoma, sarcoma, bladder cancer, bone cancer, brain tumor, cervical cancer, renal cell cancer, colorectal cancer, esophageal cancer, gastric cancer, head and neck cancer, kidney cancer, myeloma, thyroid cancer, leukaemia, breast cancer, ovarian cancer, pancreatic cancer, liver cancer, lung cancer, glioblastoma multiforme, glioma, melanoma, prostate cancer, glioblastoma, squamous cell carcinoma, multiple myeloma, skin cancer, testicular cancer, neuroblastoma and metastatic cancer.

17. A method for identifying ligands for the adenosine 2a receptor, wherein a compound of claim 1 in labelled form is the reference compound.

18. A method for the treatment or prophylaxis of a disease or disorder associated with the adenosine 2a receptor in a mammal, which comprises administering to the mammal a therapeutically effective amount of the pharmaceutical composition of claim 12.

19. The method of claim 18, wherein the disease or disorder associated with the adenosine 2a receptor is a disease or disorder selected from the group consisting of cancer, neurodegenerative diseases, retinal degenerative diseases, insomnia, pain, psychiatric diseases, ischemia, infarction, acute inflammatory diseases, chronic inflammatory diseases, spinal cord injury, and epilepsy.

20. The method of claim 18, wherein the disease or disorder associated with the adenosine 2a receptor is cancer, and wherein the cancer is selected from the group consisting of lymphoma, sarcoma, bladder cancer, bone cancer, brain tumor, cervical cancer, renal cell cancer, colorectal cancer, esophageal cancer, gastric cancer, head and neck cancer, kidney cancer, myeloma, thyroid cancer, leukaemia, breast cancer, ovarian cancer, pancreatic cancer, liver cancer, lung cancer, glioblastoma multiforme, glioma, melanoma, prostate cancer, glioblastoma, squamous cell carcinoma, multiple myeloma, skin cancer, testicular cancer, neuroblastoma and metastatic cancer.

21. The method as claimed in claim 16, wherein the cancer is renal cell cancer or lung cancer.

22. The method as claimed in claim 16, wherein the therapeutically effective amount of the compound is administered as an oral dosage.

23. The method as claimed in claim 16, wherein the compound is administered simultaneously, sequentially, or separately with one or more further therapeutic agent(s).

24. The method as claimed in claim 23, wherein the further therapeutic agent is a checkpoint inhibitor.

25. The method of claim 18, wherein the cancer is renal cell cancer or lung cancer.

26. The method as claimed in claim 18, wherein the therapeutically effective amount of the pharmaceutical composition is administered as an oral dosage.

27. The method as claimed in claim 18, wherein the pharmaceutical composition is administered simultaneously, sequentially or separately with one or more further therapeutic agent(s).

28. The method as claimed in claim 27, wherein the further therapeutic agent is a checkpoint inhibitor.

* * * * *